US009805123B2

(12) United States Patent
Nair et al.

(10) Patent No.: US 9,805,123 B2
(45) Date of Patent: Oct. 31, 2017

(54) SYSTEM AND METHOD FOR DATA PRIVACY IN URL BASED CONTEXT QUERIES

(75) Inventors: Rahul Nair, Sunnyvale, CA (US); Marc Eliot Davis, San Francisco, CA (US); Christopher William Higgins, Portland, OR (US); Simon P King, Berkeley, CA (US)

(73) Assignee: EXCALIBUR IP, LLC, New York, NY (US)

(*) Notice: Subject to any disclaimer, the term of this patent is extended or adjusted under 35 U.S.C. 154(b) by 1185 days.

(21) Appl. No.: 12/273,345

(22) Filed: Nov. 18, 2008

(65) Prior Publication Data

US 2010/0125605 A1 May 20, 2010

(51) Int. Cl.
*G06F 17/30* (2006.01)
*H04L 29/06* (2006.01)
(Continued)

(52) U.S. Cl.
CPC ........ *G06F 17/30867* (2013.01); *A61K 31/19* (2013.01); *C07C 69/704* (2013.01); *C12Q 1/25* (2013.01); *H04L 63/102* (2013.01); *H04W 12/08* (2013.01); *A61K 31/194* (2013.01); *H04W 80/08* (2013.01)

(58) Field of Classification Search
CPC ................................................. G06F 17/30867
See application file for complete search history.

(56) References Cited

U.S. PATENT DOCUMENTS 5,446,891 A 8/1995 Kaplan et al.
5,493,692 A 2/1996 Theimer et al.
(Continued)

FOREIGN PATENT DOCUMENTS

EP 1362302 11/2003
JP 2002312559 10/2002
(Continued)

OTHER PUBLICATIONS

"A Context Framework for Ambient Intelligence", Asuman DOGAC, et al., 2003, 1-8 pages,citeseerx.ist.psu.edu/viewdoc/download?doi=10.1.1.108.6656 . . . .*
(Continued)

*Primary Examiner* — Alexey Shmatov
(74) *Attorney, Agent, or Firm* — James J. DeCarlo; Greenberg Traurig, LLP

(57) ABSTRACT

A system and method for data privacy in URL based context queries. A reference to a data object is received from a user. At least one entity that controls the data object is identified via the network. At least one permission for the data object is retrieved via the network, wherein the permission is associated with the entity that controls the data object. It is then determined, via the network, if the user is permitted to access to the data object using the permission for the data object and spatial data, temporal data social data and logical data available to the network that relates to the user and to the permission for the data object. If the user is permitted access to the data object, access is granted to the data object, and if the user is nor permitted access to the data object, access is denied to the data object.

21 Claims, 20 Drawing Sheets

(51) Int. Cl.

| | |
|---|---|
| ***H04W 12/08*** | (2009.01) |
| ***A61K 31/19*** | (2006.01) |
| ***C07C 69/704*** | (2006.01) |
| ***C12Q 1/25*** | (2006.01) |
| *H04W 80/08* | (2009.01) |
| *A61K 31/194* | (2006.01) |

(56) References Cited

U.S. PATENT DOCUMENTS 5,583,763 A 12/1996 Atcheson et al.
5,651,068 A 7/1997 Klemba et al.
5,761,662 A 6/1998 Dasan
5,764,906 A 6/1998 Edelstein et al.
5,781,879 A 7/1998 Arnold et al.
5,784,365 A 7/1998 Ikeda
5,787,428 A * 7/1998 Hart
5,794,210 A 8/1998 Goldhaber et al.
5,802,510 A 9/1998 Jones
5,835,087 A 11/1998 Herz
5,903,848 A 5/1999 Takahashi
5,920,854 A 7/1999 Kirsch et al.
6,014,638 A 1/2000 Burge et al.
6,021,403 A 2/2000 Horvitz et al.
6,047,234 A 4/2000 Cherveny et al.
6,098,065 A 8/2000 Skillen et al.
6,112,181 A 8/2000 Shear et al.
6,157,924 A 12/2000 Austin
6,169,992 B1 1/2001 Beall et al.
6,212,552 B1 4/2001 Biliris et al.
6,266,667 B1 7/2001 Olsson
6,314,365 B1 11/2001 Smith
6,314,399 B1 11/2001 Deligne et al.
6,324,519 B1 11/2001 Eldering
6,327,590 B1 12/2001 Chidlovskii et al.
6,446,065 B1 9/2002 Nishioka et al.
6,490,698 B1 12/2002 Horvitz et al.
6,502,033 B1 12/2002 Phuyal
6,523,172 B1 2/2003 Martinez-Guerra et al.
6,571,279 B1 5/2003 Herz et al.
6,601,012 B1 7/2003 Horvitz et al.
6,662,195 B1 12/2003 Langseth et al.
6,665,640 B1 12/2003 Bennett et al.
6,694,316 B1 2/2004 Langseth et al.
6,701,311 B2 3/2004 Biebesheimer et al.
6,701,315 B1 3/2004 Austin
6,708,203 B1 3/2004 Maker et al.
6,731,940 B1 5/2004 Nagendran
6,741,980 B1 5/2004 Langseth et al.
6,757,661 B1 6/2004 Blaser et al.
6,773,344 B1 8/2004 Gabai et al.
6,781,920 B2 8/2004 Bates et al.
6,785,670 B1 8/2004 Chiang et al.
6,789,073 B1 9/2004 Lunenfeld
6,813,501 B2 11/2004 Kinnunen et al.
6,816,850 B2 11/2004 Culliss
6,829,333 B1 12/2004 Frazier
6,834,195 B2 12/2004 Brandenberg et al.
6,842,761 B2 1/2005 Diamond et al.
6,845,370 B2 1/2005 Burkey et al.
6,850,252 B1 2/2005 Hoffberg
6,853,913 B2 2/2005 Cherveny et al.
6,853,982 B2 2/2005 Smith et al.
6,882,977 B1 4/2005 Miller
6,904,160 B2 6/2005 Burgess
6,931,254 B1 8/2005 Egner et al.
6,961,660 B2 11/2005 Underbrink et al.
6,961,731 B2 11/2005 Holbrook
6,985,839 B1 1/2006 Motamedi et al.
7,010,492 B1 3/2006 Bassett et al.
7,027,801 B1 4/2006 Hall et al.
7,058,508 B2 6/2006 Combs et al.
7,058,626 B1 6/2006 Pan et al.
7,062,510 B1 6/2006 Eldering
7,065,345 B2 6/2006 Carlton et al.
7,065,483 B2 6/2006 Decary et al.
7,069,308 B2 6/2006 Abrams
7,073,129 B1 7/2006 Robarts et al.
7,110,776 B2 9/2006 Sambin
7,143,091 B2 11/2006 Charnock et al.
7,149,696 B2 12/2006 Shimizu et al.
7,181,438 B1 2/2007 Szabo
7,185,286 B2 2/2007 Zondervan
7,194,512 B1 3/2007 Creemer et al.
7,203,597 B2 4/2007 Sato et al.
7,209,915 B1 4/2007 Taboada et al.
7,219,013 B1 5/2007 Young et al.
7,236,969 B1 6/2007 Skillen et al.
7,254,581 B2 8/2007 Johnson et al.
7,257,570 B2 8/2007 Riise et al.
7,305,445 B2 12/2007 Singh et al.
7,320,025 B1 1/2008 Steinberg et al.
7,340,438 B2 * 3/2008 Nordman et al. .............. 705/64
7,343,364 B2 3/2008 Bram et al.
7,395,507 B2 7/2008 Robarts et al.
7,404,084 B2 7/2008 Fransdonk
7,437,312 B2 10/2008 Bhatia et al.
7,451,102 B2 11/2008 Nowak
7,461,168 B1 12/2008 Wan
7,496,548 B1 2/2009 Ershov
7,522,995 B2 4/2009 Nortrup
7,529,811 B2 5/2009 Thompson
7,562,122 B2 7/2009 Oliver et al.
7,577,665 B2 8/2009 Rameer et al.
7,584,215 B2 9/2009 Saari et al.
7,624,104 B2 11/2009 Berkhin et al.
7,624,146 B1 11/2009 Brogne et al.
7,634,465 B2 12/2009 Sareen et al.
7,657,907 B2 2/2010 Fennan et al.
7,681,147 B2 3/2010 Richardson-Bunbury et al.
7,721,259 B2 * 5/2010 Heinke et al. ................ 717/121
7,725,492 B2 5/2010 Sittig et al.
7,729,901 B2 6/2010 Richardson-Bunbury et al.
7,769,740 B2 * 8/2010 Martinez et al. ............. 707/706
7,769,745 B2 8/2010 Naaman
7,783,622 B1 8/2010 Vandermolen et al.
7,792,040 B2 9/2010 Nair
7,802,724 B1 9/2010 Nohr
7,822,871 B2 10/2010 Stolorz et al.
7,831,586 B2 11/2010 Reitter et al.
7,860,852 B2 * 12/2010 Brunner et al. .............. 707/706
7,865,308 B2 1/2011 Athsani
7,925,708 B2 4/2011 Davis
7,949,755 B2 * 5/2011 Katoh et al. .................. 709/226
8,302,015 B2 * 10/2012 Krishnan et al. ............. 715/747
8,832,132 B1 * 9/2014 Spertus et al. ................ 707/765
2001/0013009 A1 8/2001 Greening et al.
2001/0035880 A1 11/2001 Musatov et al.
2001/0047384 A1 11/2001 Croy
2001/0052058 A1 12/2001 Ohran
2002/0014742 A1 2/2002 Conte et al.
2002/0019849 A1 2/2002 Tuvey et al.
2002/0019857 A1 2/2002 Harjanto
2002/0023091 A1 2/2002 Silberberg et al.
2002/0023230 A1 2/2002 Bolnick et al.
2002/0035605 A1 3/2002 McDowell et al.
2002/0049968 A1 4/2002 Wilson et al.
2002/0052786 A1 5/2002 Kim et al.
2002/0052875 A1 5/2002 Smith et al.
2002/0054089 A1 * 5/2002 Nicholas et al. ............. 345/745
2002/0065844 A1 5/2002 Robinson et al.
2002/0069218 A1 6/2002 Sull et al.
2002/0099695 A1 7/2002 Abajian et al.
2002/0103870 A1 8/2002 Shouji
2002/0111956 A1 8/2002 Yeo et al.
2002/0112035 A1 8/2002 Carey
2002/0133400 A1 9/2002 Terry et al.
2002/0138331 A1 9/2002 Hosea et al.
2002/0152267 A1 10/2002 Lennon
2002/0169840 A1 11/2002 Sheldon et al.
2002/0173971 A1 11/2002 Stirpe et al.
2002/0178161 A1 11/2002 Brezin et al.
2002/0198786 A1 12/2002 Tripp et al.
2003/0008661 A1 1/2003 Joyce et al.
2003/0009367 A1 1/2003 Morrison

(56) References Cited

U.S. PATENT DOCUMENTS

2003/0009495 A1 1/2003 Adjaoute
2003/0009675 A1* 1/2003 Rygaard ........................ 713/182
2003/0027558 A1 2/2003 Eisinger
2003/0032409 A1 2/2003 Hutcheson et al.
2003/0033331 A1 2/2003 Sena et al.
2003/0033394 A1 2/2003 Stine et al.
2003/0061211 A1* 3/2003 Shultz et al. ..................... 707/3
2003/0065762 A1 4/2003 Stolorz et al.
2003/0069877 A1 4/2003 Grefenstette et al.
2003/0069880 A1 4/2003 Harrison et al.
2003/0078978 A1 4/2003 Lardin et al.
2003/0080992 A1 5/2003 Haines
2003/0126250 A1 7/2003 Jhanji
2003/0149574 A1 8/2003 Rudman
2003/0154293 A1 8/2003 Zmolek
2003/0165241 A1 9/2003 Fransdonk
2003/0182310 A1* 9/2003 Charnock et al. ......... 707/104.1
2003/0191816 A1 10/2003 Landress et al.
2003/0200192 A1* 10/2003 Bell et al. ......................... 707/1
2004/0010492 A1 1/2004 Zhao et al.
2004/0015588 A1 1/2004 Cotte
2004/0030798 A1 2/2004 Andersson et al.
2004/0034752 A1 2/2004 Ohran
2004/0043758 A1 3/2004 Sorvari et al.
2004/0044736 A1 3/2004 Austin-Lane et al.
2004/0070602 A1 4/2004 Kobuya et al.
2004/0139025 A1 7/2004 Coleman
2004/0139047 A1 7/2004 Rechsteiner
2004/0148341 A1 7/2004 Cotte
2004/0152477 A1 8/2004 Wu et al.
2004/0183829 A1 9/2004 Kontny et al.
2004/0201683 A1 10/2004 Murashita et al.
2004/0203851 A1 10/2004 Vetro et al.
2004/0203909 A1 10/2004 Koster
2004/0209602 A1 10/2004 Joyce et al.
2004/0243623 A1 12/2004 Ozer et al.
2004/0260804 A1 12/2004 Grabarnik et al.
2004/0267880 A1 12/2004 Patiejunas
2005/0005242 A1 1/2005 Hoyle
2005/0015451 A1 1/2005 Sheldon et al.
2005/0015599 A1 1/2005 Wang et al.
2005/0050027 A1 3/2005 Yeh
2005/0050043 A1 3/2005 Pyhalammi et al.
2005/0055321 A1 3/2005 Fratkina
2005/0060381 A1 3/2005 Huynh et al.
2005/0065950 A1 3/2005 Chaganti et al.
2005/0065980 A1 3/2005 Hyatt et al.
2005/0076060 A1 4/2005 Finn et al.
2005/0086187 A1 4/2005 Grosser et al.
2005/0105552 A1 5/2005 Osterling
2005/0108213 A1 5/2005 Riise et al.
2005/0120006 A1 6/2005 Nye
2005/0131727 A1 6/2005 Sezan et al.
2005/0149397 A1 7/2005 Morgenstern et al.
2005/0151849 A1 7/2005 Fitzhugh et al.
2005/0159220 A1 7/2005 Wilson et al.
2005/0159970 A1 7/2005 Buyukkokten et al.
2005/0160080 A1 7/2005 Dawson
2005/0165699 A1 7/2005 Hahn-Carlson
2005/0166240 A1 7/2005 Kim
2005/0171955 A1 8/2005 Hull et al.
2005/0177385 A1 8/2005 Hull et al.
2005/0182824 A1 8/2005 Cotte
2005/0183110 A1 8/2005 Anderson
2005/0187786 A1 8/2005 Tsai
2005/0192025 A1 9/2005 Kaplan
2005/0203801 A1 9/2005 Morgenstern et al.
2005/0216295 A1 9/2005 Abrahamsohn
2005/0216300 A1 9/2005 Appelman et al.
2005/0219375 A1 10/2005 Hasegawa et al.
2005/0234781 A1 10/2005 Morgenstern
2005/0262132 A1* 11/2005 Morita et al. ................. 707/102
2005/0273510 A1 12/2005 Schuh
2006/0020631 A1 1/2006 Cheong Wan et al.
2006/0026013 A1 2/2006 Kraft
2006/0026067 A1 2/2006 Nicholas et al.
2006/0031108 A1 2/2006 Oran
2006/0040719 A1 2/2006 Plimi
2006/0047563 A1 3/2006 Wardell
2006/0047615 A1 3/2006 Ravin
2006/0047657 A1* 3/2006 Frieder et al. .................... 707/9
2006/0053058 A1 3/2006 Hotchkiss et al.
2006/0069612 A1 3/2006 Hurt et al.
2006/0069616 A1 3/2006 Bau
2006/0069749 A1 3/2006 Herz et al.
2006/0074853 A1 4/2006 Liu et al.
2006/0085392 A1 4/2006 Wang et al.
2006/0085419 A1 4/2006 Rosen
2006/0089876 A1 4/2006 Boys
2006/0116924 A1 6/2006 Angeles et al.
2006/0123053 A1 6/2006 Scannell, Jr.
2006/0129313 A1 6/2006 Becker
2006/0129605 A1 6/2006 Doshi
2006/0161894 A1 7/2006 Oustiougov et al.
2006/0168591 A1 7/2006 Hunsinger et al.
2006/0173838 A1 8/2006 Garg et al.
2006/0173985 A1 8/2006 Moore
2006/0178822 A1 8/2006 Lee
2006/0184508 A1 8/2006 Fuselier et al.
2006/0184579 A1 8/2006 Mills
2006/0212330 A1 9/2006 Savilampi
2006/0212401 A1 9/2006 Amerally et al.
2006/0227945 A1 10/2006 Runge et al.
2006/0235816 A1 10/2006 Yang et al.
2006/0236257 A1 10/2006 Othmer et al.
2006/0242139 A1 10/2006 Butterfield et al.
2006/0242178 A1 10/2006 Butterfield et al.
2006/0242259 A1 10/2006 Vallath et al.
2006/0258368 A1 11/2006 Granito et al.
2006/0282455 A1 12/2006 Lee
2007/0013560 A1 1/2007 Casey
2007/0015519 A1 1/2007 Casey
2007/0043766 A1 2/2007 Nicholas et al.
2007/0067104 A1 3/2007 Mays
2007/0067267 A1 3/2007 Ives
2007/0072591 A1 3/2007 McGary et al.
2007/0073583 A1 3/2007 Grouf et al.
2007/0073641 A1 3/2007 Perry et al.
2007/0086061 A1 4/2007 Robbins
2007/0087756 A1 4/2007 Hoffberg
2007/0088852 A1 4/2007 Levkovitz
2007/0100956 A1 5/2007 Kumar
2007/0112762 A1 5/2007 Brubaker
2007/0121843 A1 5/2007 Atazky et al.
2007/0130137 A1 6/2007 Oliver et al.
2007/0136048 A1 6/2007 Richardson-Bunbury et al.
2007/0136235 A1 6/2007 Hess
2007/0136256 A1 6/2007 Kapur et al.
2007/0136689 A1 6/2007 Richardson-Bunbury et al.
2007/0143345 A1 6/2007 Jones et al.
2007/0150168 A1 6/2007 Balcom et al.
2007/0150359 A1 6/2007 Lim et al.
2007/0155411 A1 7/2007 Morrison
2007/0161382 A1 7/2007 Melinger et al.
2007/0162850 A1 7/2007 Adler
2007/0168430 A1 7/2007 Brun et al.
2007/0173266 A1 7/2007 Barnes
2007/0179792 A1 8/2007 Kramer
2007/0185599 A1 8/2007 Robinson et al.
2007/0192299 A1 8/2007 Zuckerberg et al.
2007/0198506 A1 8/2007 Attaran Rezaei et al.
2007/0198563 A1 8/2007 Apparao et al.
2007/0203591 A1 8/2007 Bowerman
2007/0219708 A1 9/2007 Brasche et al.
2007/0233585 A1 10/2007 Ben Simon et al.
2007/0239348 A1 10/2007 Cheung
2007/0239517 A1 10/2007 Chung et al.
2007/0239716 A1* 10/2007 Weininger et al. ............... 707/6
2007/0259653 A1 11/2007 Tang et al.
2007/0260508 A1 11/2007 Barry et al.
2007/0260604 A1 11/2007 Haeuser et al.
2007/0271297 A1 11/2007 Jaffe et al.
2007/0271340 A1 11/2007 Goodman et al.
2007/0273758 A1 11/2007 Mendoza et al.

(56) References Cited

U.S. PATENT DOCUMENTS

| | | | | |
|---|---|---|---|---|
| 2007/0276940 | A1 | 11/2007 | Abraham et al. | |
| 2007/0282621 | A1 | 12/2007 | Altman et al. | |
| 2007/0282675 | A1 | 12/2007 | Varghese | |
| 2007/0288278 | A1 | 12/2007 | Alexander et al. | |
| 2008/0005072 | A1* | 1/2008 | Meek et al. | 707/3 |
| 2008/0005313 | A1 | 1/2008 | Flake et al. | |
| 2008/0005651 | A1 | 1/2008 | Grefenstette et al. | |
| 2008/0010206 | A1 | 1/2008 | Coleman | |
| 2008/0021957 | A1 | 1/2008 | Medved et al. | |
| 2008/0026804 | A1 | 1/2008 | Baray et al. | |
| 2008/0028031 | A1 | 1/2008 | Bailey et al. | |
| 2008/0040283 | A1 | 2/2008 | Morris | |
| 2008/0046298 | A1 | 2/2008 | Ben-Yehuda et al. | |
| 2008/0070588 | A1 | 3/2008 | Morin | |
| 2008/0072290 | A1* | 3/2008 | Metzer et al. | 726/3 |
| 2008/0086356 | A1 | 4/2008 | Glassman et al. | |
| 2008/0086431 | A1 | 4/2008 | Robinson et al. | |
| 2008/0091796 | A1 | 4/2008 | Story et al. | |
| 2008/0096664 | A1 | 4/2008 | Baray et al. | |
| 2008/0102911 | A1 | 5/2008 | Campbell et al. | |
| 2008/0104061 | A1 | 5/2008 | Rezaei | |
| 2008/0104227 | A1 | 5/2008 | Birnie et al. | |
| 2008/0109761 | A1 | 5/2008 | Stambaugh | |
| 2008/0109843 | A1 | 5/2008 | Ullah | |
| 2008/0114751 | A1 | 5/2008 | Cramer et al. | |
| 2008/0120183 | A1 | 5/2008 | Park | |
| 2008/0120308 | A1 | 5/2008 | Martinez et al. | |
| 2008/0120690 | A1 | 5/2008 | Norlander et al. | |
| 2008/0133750 | A1 | 6/2008 | Grabarnik et al. | |
| 2008/0140650 | A1* | 6/2008 | Stackpole | 707/5 |
| 2008/0147655 | A1 | 6/2008 | Sinha et al. | |
| 2008/0147743 | A1 | 6/2008 | Taylor et al. | |
| 2008/0148175 | A1 | 6/2008 | Naaman et al. | |
| 2008/0154720 | A1 | 6/2008 | Gounares | |
| 2008/0163284 | A1 | 7/2008 | Martinez et al. | |
| 2008/0172632 | A1 | 7/2008 | Stambaugh | |
| 2008/0177706 | A1 | 7/2008 | Yuen | |
| 2008/0201299 | A1* | 8/2008 | Lehikoinen et al. | 707/3 |
| 2008/0243770 | A1* | 10/2008 | Aasman | 707/2 |
| 2008/0270579 | A1 | 10/2008 | Herz et al. | |
| 2008/0285886 | A1 | 11/2008 | Allen | |
| 2008/0301250 | A1 | 12/2008 | Hardy et al. | |
| 2008/0320001 | A1 | 12/2008 | Gaddam | |
| 2009/0005987 | A1 | 1/2009 | Vengroff et al. | |
| 2009/0006336 | A1 | 1/2009 | Forstall et al. | |
| 2009/0012934 | A1 | 1/2009 | Yerigan | |
| 2009/0012965 | A1 | 1/2009 | Franken | |
| 2009/0043844 | A1 | 2/2009 | Zimmet et al. | |
| 2009/0044132 | A1 | 2/2009 | Combel et al. | |
| 2009/0063254 | A1 | 3/2009 | Paul et al. | |
| 2009/0070186 | A1 | 3/2009 | Buiten et al. | |
| 2009/0073191 | A1 | 3/2009 | Smith et al. | |
| 2009/0076889 | A1 | 3/2009 | Jhanji | |
| 2009/0100052 | A1 | 4/2009 | Stern et al. | |
| 2009/0106356 | A1 | 4/2009 | Brase et al. | |
| 2009/0125517 | A1 | 5/2009 | Krishnaswamy et al. | |
| 2009/0132941 | A1 | 5/2009 | Pilskalns et al. | |
| 2009/0144141 | A1 | 6/2009 | Dominowska et al. | |
| 2009/0150501 | A1 | 6/2009 | Davis et al. | |
| 2009/0150507 | A1 | 6/2009 | Davis et al. | |
| 2009/0165051 | A1 | 6/2009 | Armaly | |
| 2009/0171939 | A1 | 7/2009 | Athsani et al. | |
| 2009/0177603 | A1 | 7/2009 | Honisch | |
| 2009/0187637 | A1 | 7/2009 | Wu et al. | |
| 2009/0204484 | A1 | 8/2009 | Johnson | |
| 2009/0204672 | A1 | 8/2009 | Jetha et al. | |
| 2009/0204676 | A1 | 8/2009 | Parkinson et al. | |
| 2009/0216606 | A1 | 8/2009 | Coffman et al. | |
| 2009/0222302 | A1 | 9/2009 | Higgins | |
| 2009/0222303 | A1 | 9/2009 | Higgins | |
| 2009/0234814 | A1 | 9/2009 | Boerries et al. | |
| 2009/0234909 | A1 | 9/2009 | Strandeil et al. | |
| 2009/0249482 | A1 | 10/2009 | Sarathy | |
| 2009/0265431 | A1 | 10/2009 | Janie et al. | |
| 2009/0281997 | A1 | 11/2009 | Jain | |
| 2009/0299837 | A1 | 12/2009 | Steelberg et al. | |
| 2009/0313546 | A1 | 12/2009 | Katpelly et al. | |
| 2009/0320047 | A1 | 12/2009 | Khan et al. | |
| 2009/0323519 | A1 | 12/2009 | Pun | |
| 2009/0328087 | A1 | 12/2009 | Higgins et al. | |
| 2010/0002635 | A1 | 1/2010 | Eklund | |
| 2010/0014444 | A1 | 1/2010 | Ghanadan et al. | |
| 2010/0063993 | A1 | 3/2010 | Higgins et al. | |
| 2010/0070368 | A1 | 3/2010 | Choi et al. | |
| 2010/0118025 | A1 | 5/2010 | Smith et al. | |
| 2010/0125563 | A1 | 5/2010 | Nair et al. | |
| 2010/0125569 | A1 | 5/2010 | Nair et al. | |
| 2010/0125604 | A1 | 5/2010 | Martinez et al. | |
| 2010/0125605 | A1 | 5/2010 | Nair et al. | |
| 2010/0185642 | A1 | 7/2010 | Higgins et al. | |
| 2013/0283359 | A1* | 10/2013 | Lu et al. | 726/5 |

FOREIGN PATENT DOCUMENTS

| | | |
|---|---|---|
| KR | 1020000036897 | 7/2000 |
| KR | 1020000054319 | 9/2000 |
| KR | 10-2000-0064105 | 11/2000 |
| KR | 1020030049173 | 6/2003 |
| KR | 10-0801662 | 2/2005 |
| KR | 1020060043333 | 5/2006 |
| KR | 102007034094 | 3/2007 |
| KR | 1020070073180 | 7/2007 |
| KR | 1020080048802 | 6/2008 |
| WO | WO2006/116196 | 11/2006 |
| WO | WO 2007/022137 | 2/2007 |
| WO | WO 2007/027453 | 3/2007 |
| WO | WO 2007070358 | 6/2007 |
| WO | WO2007113546 | 10/2007 |

OTHER PUBLICATIONS

"Matching User's Semantics with Data Semantics in Location-Based Services", Shijun Yu et al. , 2005, 1-6 pages, citeseerx.ist.psu.edu/viewdoc/summary?doi=10.1.1.90.1259.*

"The role of shared context in supporting cooperation between city visitors", Keith Cheverst et al., 2001, http://www.sciencedirect.com/science/article/pii/S0097849301000838.*

Axup, Jeff et al., "Conceptualizing New Mobile Devices by Observing Gossip and Social Network Formation Amongst the Extremely Mobile", ITEE Technical Report #459, Dec. 19, 2005, pp. 1-71.

Conhaim, Wallys W., "Social networks: the Internet continues to evolve: where is the money in all this? That is what venture capitalists are asking. (Perspectives)", Information Today, 22, 9, 35(2), Oct. 2005, (pp. 1-5 of attached).

Davis, Marc et al., "From Context to Content: Leveraging Context to Infer Media Metadata", ACM Press, Oct. 10, 2004, pp. 1-8.

Kaasinen, E., "Behaviour & Information Technology", Taylor & Francis, vol. 24, No. 1, Jan./Feb. 2005, pp. 37-49, (Abstract only attached).

Konomi, Shin'ichi et al., "Supporting Colocated Interactions Using RFID and Social Network Displays", Pervasive Computing, Jul.-Sep. 2006 , vol. 5, No. 3, pp. 48-56 (pp. 1-4 of attached).

Lin, F. et al., "A unified framework for managing Web-based services.", Information Systems and e-Business Management, vol. 3, Oct. 2005, p. 299, (pp. 1-15 of attached).

Metz, Cade, "MySpace Nation", PC Magazine, Jun. 21, 2006, pp. 1-10 attached.

Perkowitz, Mike et al., "Utilizing Online Communities to Facilitate Physical World Interactions", The International Conference on Communities and Technologies, Sep. 19, 2003, Amsterdam, pp. 1 6.

Roush, Wade, "Social Machines", Continuous Computing Blog, Jul. 5, 2005, pp. 1-21.

Roush, Wade, "Social Machines", Technology Review, Aug. 2005, pp. 45-51.

Sheppard, Brett, "The Rights Stuff: The Integration of Enterprise Digital Rights Management Into an Enterprise Architecture", ECantent, vol. 29, No. 9, Nov. 2006, p. 38, 40-44, (pp. 1-7 of attached).

(56) References Cited

OTHER PUBLICATIONS

Voight, Joan et al., "Lessons for Today's Digital Market", Adweekcom, Oct. 2, 2006, pp. 1-6.
"Companies add new communication features to photo sharing.", Digital Imaging Digest, Feb. 2006, pp. 1-2.
"Dave.TV and Eye Music Network Empower Users to Create Their Own Music TV Channel on Their Sites With New IPTV Channel", www.davenw.com/2006, Sep. 13, 2006, pp. 1-2.
"Digital rights management: a primer: developing a user-friendly means of protecting content.(Profile)", Screen Digest, No. 420, p. 305, Sep. 2006, (pp. 1-9 of attached)
"Emerging Markets: What media 2.0 can offer advertisers.", Campaign, Oct. 27, 2006, p. 26, (pp. 1-5 of attached)
"Reality Digital Debuts Opus", www.lightreading.com. Sep. 25, 2006, pp. 1.
"Reality Digital—Making Media Move", www.realitydigital.com, Nov. 28, 2006, pp. 1-2.
Nedos, A; Singh K., Clarke S, Proximity Based Group Communications for Mobile Ad Hoc Networks; Proximity-Based Group Communication; Global Smart Spaces; D.14; Oct. 3, 2003; 31 pages.
Brunato, M; Battiti R. "PILGRIM: A Location Broker and Mobility-Aware Recommendation System"; Technical report DIT-02-0092, Universita di Trento, Oct. 2002; 8 pages.
Backstrom et al., Spatial Variation in Search Engine Queries, WWW•2008, Beijing, China (Apr. 21-25, 2008).
Gan et al., Analysis of Geographic Queries in a Search Engine Log, LocWeb 2008, Beijing, China (Apr. 22, 2008).
Jones et al., Geographic Intention and Modification in Web Search, International Journal of Geographical Information Science, vol. 22, No. 3, pp. 1-20 (Jul. 2008).
Sanderson et al., Analyzing Geographic Queries; Department of Information Studies; University of Sheffield, UK; 2 pages.
Go With the Flow, The Economist Technology Quarterly, vol. 382, Issue 8519, 4 pages, (Mar. 10, 2007).
International Search Report and Written Opinion (PCT/US2009/060476) dated May 4, 2010; 12 pages.
International Search Report and Written Opinion (PCT/US2009/060374) dated Apr. 30, 2010; 12 pages.
International Search Report (PCT/US2009/060379) dated Apr. 30, 2010; 3 pages.
International Search Report and Written Opinion (PCT/US2008/085135) dated May 25, 2009; 7 pages.
International Search Report (PCT/US2009/055503) dated Apr. 8, 2010; 3 pages.
Written Opinion (PCT/US2008/085915) dated Jun. 29, 2009; 4 pages.
Written Opinion (PCT/US2008/086948) dated May 21, 2009; 5 pages.
International Search Report and Written Opinion (PCT/US2009/051247) dated Jan. 25, 2010; 9 pages.
International Search Report and Written Opinion (PCT/US2009/046258) dated Dec. 23, 2009; 7 pages.
Almieda, R.B. et al. "A Community-Aware Search Engine," WWW2004, New York., NY, May 17-22, 2004, pp. 413-421.
Anonymous. (Jul. 16, 2006). MyFantasyLeague Fantasy Football League Management—Features, located at <http://web.archive.org/web/20060716072900/www.myfantasyleague.com/features.htm >, last visited on Feb. 10, 2009, four pages.
Anonymous. (Jul. 17, 2006). "Fantasy Football Lineup Analyzer—Tips for Who to Start & Who to Bench each Week," located at http://web.archive.org/web/200607171633529/www.fantasyfootballstarters.com/lineupAnalyzer.jsp>, last visited on Feb. 10, 2009, one page.
Bharat, K. (Date Unknown). "SearchPad: Explicit Capture of Search Context to Support Web Search," located at <http://www9.org/w9cdrom/173/173.html >, last visited Aug. 1, 2007, 13 pages.
Budzik, J. et al. (2000). "User Interactions with Everyday Applications as Context for Just-in-Time Information Access," Proceeding of the 2000 Conference on Intelligent User Interfaces, eight pages.
Finkelstein, L. et al. (2001). "Placing Search in Context: The Concept Revisited," WWW/O, Hong Kong, May 2-5, 2001, pp. 406-414.
Freyne, J. et al. (2004). "Further Experiments on Collaborative Ranking in Community-Based Web Search," Artificial Intelligence Review, pp. 1-23.
Lieberman, H. (1995) "Letizia: An Agent that Assists Web Browsing," Proceedings of the Fourteenth International Joint Conference on Artificial Intelligence, Aug. 20-25, 1995, six pages.
Mitra, M. et al. (1998). "Improving Automatic Query Expansion," Proceedings of the AMC SIGIR, nine pages.
Rhodes, B.J. et al. (1996). "Remembrance Agent: A Continuously Running Automated Information Retrieval System," Proceedings of the First International Conference on the Practical Application of Intelligent Agents and Multi Agent Technology (PAAM), pp. 487-495, located at <http://www.cc.gatech.edu/fac/Thad.Starner/p/032_40_agents&ubicomp/remembrance-agent . . . >, last visited Aug. 1, 2007, six pages.
Sansbury, C. (Sep. 13, 2005). "Yahoo! Widget for BBC Sports News—Scotland," 32. located at <http://widgets.yahoo.com/gallery/view.php?widget=37220 >, last visited on Feb. 7, 2007, one page.
Yahoo! Inc. (Dec. 7, 2005). "Yahoo! Widget Engine 3.0 Reference Manual Version 3.0," 300 pages.
U.S. Appl. No. 12/407,690, filed Mar. 19, 2009; 50 pages.
U.S. Appl. No. 12/407,681, filed Mar. 19, 2009; 56 pages.
International Search Report PCT/US2008/088228 dated Sep. 30, 2009—2 pages.
Written Opinion PCT/US2008/088228 dated Sep. 30, 2009—5 pages.
U.S. Appl. No. 11/617,451, filed Dec. 28, 2006, Kalaboukis.
U.S. Appl. No. 11/562,973, filed Nov. 22, 2006, Martinez.
U.S. Appl. No. 11/562,974, filed Nov. 22, 2006, Martinez.
U.S. Appl. No. 11/562,976, filed Nov. 22, 2006, Martinez.
U.S. Appl. No. 11/562,979, filed Nov. 22, 2006, Martinez.
U.S. Appl. No. 12/237,709, filed Sep. 25, 2008, Martinez.
U.S. Appl. No. 12/399,669, filed Mar. 6, 2009, King.
U.S. Appl. No. 11/353,657, filed Feb. 13, 2006, Mor Naaman.
U.S. Appl. No. 11/437,344, filed May 19, 2006, Jaffe.
U.S. Appl. No. 11/593,869, filed Nov. 6, 2006, Mor Naaman.
U.S. Appl. No. 11/593,668, filed Nov. 6, 2006, Mor Naaman.
Allen James F., "Maintaining Knowledge About Temporal Intervals", Communications of the ACM, Nov. 1983, vol. 26, No. 11 pp. 832-843; 12 pages.
Press Release, "QUALCOMM Conducts First Live Demonstration of FL Technology on a Wireless Handset", Qualcomm Inc., San Diego, Sep. 27, 2005; 3 pages.
MediaFlo, FLO Technology Overview, Qualcomm Inc. Copyright 2007; 24 pages.
Axup, Jeff et al., "Conceptualizing New Mobile Devices by Observing Gossip and Social Network Formation Amongst the Extremely Mobile", ITEE Technical Report #459, Dec. 19, 2005, pp. 1-71
"Digital rights management: a primer: developing a user-friendly means of protecting content.(Profile)", Screen Digest, No. 420, p. 305, Sep. 2006, (pp. 1-9 of attached).
"Emerging Markets: What media 2.0 can offer advertisers.", Campaign, Oct. 27, 2006, p. 26, (pp. 1-5 of attached).
Notification of Transmittal of The International Search Report and The Written Opinion of The International Search Authority, or Declaration (PCT/US2007/084797) dated Mar. 21, 2008; 11 pages.
International Search Report (PCT/US2007/084807) dated May 27, 2008; 3 pages.
International Preliminary Report on Patentability (PCT/US2007/084807) dated May 26, 2009; 5 pages.
International Search Report (PCT/US2010/026063) dated May 27, 2008; 3 pages.

(56) References Cited

OTHER PUBLICATIONS

Rekimoto, et al., "CyberCode: designing augmented reality environments with visual tags." Proceedings of DARE 2000 on Designing augmented reality environments, Elsinore, Denmark, pp. 1-11 Apr. 12-14, 2000.
"Semacode—URL Barcodes—practical ubiquitous computing", located at http://semacode.org visited on Apr. 13, 2007; 3 pages.
"Technical White Paper: Choosing the best 2D barcode format for mobile apps," Semacode, Jul. 15, 2006; pp. 1-7 located at http://semacode.org/about/technical/whitepaper/best2_d_code.pdf.
Carbonell, J. et al. (Aug. 24-28, 1998). "The Use of MMR, Diversity-Based Reranking for Reordering Documents and Producing Summaries," SIGIR '98: Proceedings of the 21 S Annual International ACM SIGIR Conference on Research and Development in Information Retrieval: Melbourne, Australia W.B. Croft et al. eds., pp. 335-336.
Cooper, M. et al. (Nov. 2-8, 2003). "Temporal Event Clustering for Digital Photo Collections," MM'03 Berkeley, California, pp. 364-373.
Davis, M. et al. (Oct. 10-16, 2004). "From Context to Content: Leveraging Context to Infer Media Metadata," MM'04 New York, New York. 9 pages.
Davis, M. et al. "From Context to Content: Leveraging Context for Mobile Media Metadata." 9 pages.
Davis, M. et al. (Apr. 2-7, 2005). "MMM2: Mobile Media Metadata for Media Sharing," CHI 2005 Portland, Oregon. 4 pages.
Davis, M. et al. "Mobile Media Metadata for Mobile Imaging." Jun. 27-30, 2004; 4 pages.
Davis, M. et al. "Using Context and Similarity for Face and Location Identification." 10 pages.
Flickr. "Welcome to Flickr—Photo Sharing," located at <http://www.flickr.com > visited on Feb. 26, 2007, one page.
Gargi, U. (Aug. 7, 2003). "Consumer Media Capture: Time-Based Analysis and Event Clustering," Technical Report HPL-2003-165 HP Laboratories Palo Alto, pp. 1-15.
Goldberger, J. et al. The Hungarian Clustering Method, located at <http://scholar.googles.com/scholar?num=20&h1=en&lr=&9=cache:vbwsIsm1CisJ:www.openu .acil/Personal_sites/tarnirtassa/Publications/hcm.pdf+goldberger+clustering+method+hungarian> visited on Mar. 1, 2007, twelve pages.
Graham, A. et al. (Jul. 13-17, 2002). Time as Essence for Photo Browsing Through Personal Digital Libraries, JCDL '02 Portland, Oregon. 11 pages.
Jaffe, A. et al. (May 23-26, 2006). "Generating Summaries for Large Collections of Geo-Referenced Photographs," WWW 2006 Edinburgh, Scotland. 2 pages.
Jaffe, A. et al. (Oct. 26-27, 2006). "Generating Summaries and Visualization for Large Collections of Geo-Referenced Photographs," MIR '06 Santa Barbara, California. 11 pages.
Joshi, D. et al. (Oct. 15-16, 2004). "The Story Picturing Engine: Finding Elite Images to Illustrate a Story Using Miitual Reinforcement," MIR '04 New York, New York. 9 pages.
Naaman, M. et al. (Nov. 2003). "From Where to What: Metadata Sharing for Digital Photographs with Geographic Coordinates," In on the Move to Meaningful Internet Systems 2003: Coop/S, DOA, and Odbase R. Meersman et al. eds., pp. 196-217.
Naaman, M. et al. (Jun. 7-11, 2004). "Automatic Organization for Digital Photographs with Geographic Coordinates" Proceedings of the Fourth ACM/IEEE Joint Conference on Digital Libraries Global Reach and Diverse Impact: Tucson, Arizona, pp. 53-62.
Nair, R. et al. (Nov. 6-11, 2005). "Photo L01: Browsing Multi-User Photo Collections," MM'05 Singapore, pp. 223-224.
0' Hare, N. et al. "Combination of Content Analysis and Context Features for Digital Photograph Retrieval." 7 pages.
Pigeau, A. et al. (Jun. 17, 2005). "Organizing a Personal Image Collection with Statistical Model-Based ICL Clustering on Spatio-Temporal Camera Phone Meta-Data." 25 pages.
Sarvas, R. et al. (Jun. 6-9, 2004). "Metadata Creation System for Mobile Images," MobiSys'04 Boiton, Massachusetts, pp. 36-48.
Toyama, K. et al. (Nov. 2-8, 2003). "Geographic Location Tags on Digital Images," MM '03'Berkeley: California. 12 pages.
U.S. Appl. No. 11/593,668, filed Nov. 6, 2006 for Naaman, et al.
U.S. Appl. No. 11/593,869, filed Nov. 6, 2006 for Naaman, et al.
"Gutenkarte" Book Catalog, 2006 MetaCarta, Inc., www.gutenkarte.org 11pgs.
Baron, N.S. et al. (Aug. 30, 2005). "Tethered or Mobile? Use of Away Messages in Instant Messaging by American College Students," Chapter 20.1 in Mobile Communication, Springer: London, England, 31:293-297.
Jones, C. et al. (2004). "Ad-Hoc Meeting System," Final Presentation from Project Group #7, SIMS 202, Fall 2004 Class, UC Berkley School of Information Management & Systems, located at <http://www2.sims.berkeley.edu/academics/courses/is202/f04/phone_project/Group7/ >, last visited on Feb. 2, 2010, thirteen pages.
Manguy, L. et al. (2006). "iTour—Packing the World Into Your Mobile Device," Final Presentation from Project Group #6, SIMS 202, Fall 2004 Class, UC Berkley School of Information Management & Systems, located at <http://www2.sims.berkeley.edu/academics/courses/is202/f04/phone_project/Group6/index.h > . . . , last visited on Feb. 2, 2010, ten pages.
Mitnick, S. et al. (2004). "Pillbox," Final Presentation from Project Group #8, SIMS: 02: Fall 2004 Class, UC Berkley School of Information Management & Systems, located at <http://www2.sims.berkeley.edu/academics/courses/is202/f04/phone_project/Group8/about.p . . . ,> last visited on Feb. 2, 2010, seventeen pages.
Wooldridge, M. et al. (2005). "STALK. The Camera-phone Scavenger Hunt!" located at <http://www.stalk.com >, last visited on Dec. 28, 2009, two pages.
www.stalk.com (retrieved on Dec. 29, 2009) pp. 1-2.
Anonymous. (Date Unknown). "CommunityWalk—About," located at <http://www.communitywalk.com/about >, last visited on Mar. 3, 2008, one page.
Anonymous. (Date Unknown). "CommunityWalk Mapping Made Easy," located at <http://www.communitywalk.com/>, last visited on Mar. 3, 2008, one page.
Anonymous. (Date Unknown). "Google Earth User Guide" located at <http://earth.google.com/userguide/v4/>, last visited on Feb. 27, 2008, twelve pages.
Anonymous. (Date Unknown). "Google Earth—Wikipedia, the Free Encyclopedia," located at <http://en.wikipedia.org/wiki/Google_earth >, last visited on Mar. 3, 2008, fourteen pages.
Anonymous. (Date Unknown). "Google Earth User Guide—Using Image Overlays and 3D Models," located at <http://earth.google.com/userguide/v4/ug_imageoverlays.html >, nine pages.
Anonymous. (Date Unknown). "Google Maps," located at <http://en.wikipedia.org/wiki/Google_maps >, last visited on Feb. 27, 2008, eleven pages.
Anonymous. (Date Unknown). "Live Search Maps," located at <http://en.wikipedia.org/wiki/Windows_live_maps >, last visited on Mar. 3, 2008, six pages.
Anonymous. (Date Unknown). "WikiMapia," located at <http://en.wikipedia.org/wiki/WikiMapia >, last visited on Mar. 3, 2008, three pages.
Anonymous. (2007). "Ask.com Maps & Directions," located at <http://maps.ask.com/maps >, last visited on Mar. 3, 2008, one page.
Anonymous. (2007). "Wayfaring Follow You, Follow Me," located at <http://www.wayfaring.com/>, last visited on Mar. 3, 2008, three pages.
Anonymous. (2008). "Platial the People's Atlas," located at <www.platial.com >, last visited on Mar. 3, 2008, one page.
Anonymous. (2008). "Wikimpaia.org ," located at <http://wikimpaia.org/>, last visited on Mar. 3, 2008, one page.
U.S. Appl. No. 12/409,867, filed Mar. 24, 2009, King.
U.S. Appl. No. 12/540,098, filed Aug. 12, 2009, Martinez.
U.S. Appl. No. 12/536,892, filed Aug. 6, 2009, King.
U.S. Appl. No. 12/540,588, filed Aug. 13, 2009, Tendjoukian.
U.S. Appl. No. 12/015,115, filed Jan. 16, 2006, Higgins.
U.S. Appl. No. 12/180,486, filed Jul. 25, 2008, Higgins.
U.S. Appl. No. 12/180,499, filed Jul. 25, 2008, Higgins.
U.S. Appl. No. 12/015,146, filed Jan. 16, 2008, Higgins.

(56) References Cited

OTHER PUBLICATIONS

U.S. Appl. No. 12/041,088, filed Mar. 3, 2008, Higgins.
U.S. Appl. No. 12/041,062, filed Mar. 3, 2008, Higgins.
U.S. Appl. No. 12/041,054, filed Mar. 3, 2008, Higgins.
U.S. Appl. No. 12/540,269, filed Aug. 12, 2009, Kalaboukis.
U.S. Appl. No. 11/969,815, filed Jan. 4, 2004, Davis.
U.S. Appl. No. 12/182,111, filed Jul. 29, 2008, Davis.
U.S. Appl. No. 12/434,575, filed May 1, 2009, O'Sullivan.
U.S. Appl. No. 12/434,580, filed May 1, 2009, O'Sullivan.
U.S. Appl. No. 12/407,690, filed Mar. 19, 2009, Davis.
U.S. Appl. No. 12/407,681, filed Mar. 19, 2009, Athsani.
International Search Report (PCT/US2009/030405) dated Sep. 23, 2009; 2 pages.
U.S. Appl. No. 12/041,054 file history dated Mar. 3, 2008; 64 pgs.
U.S. Appl. No. 12/041,062 file history dated Mar. 3, 2008; 66 pgs.
U.S. Appl. No. 12/041,088 file history dated Mar. 3, 2008; 66 pgs.
U.S. Appl. No. 12/169,931 file history dated Jul. 9, 2008; 66 pgs.
U.S. Appl. No. 12/170,025 file history dated Jul. 9, 2008; 67 pgs.
U.S. Appl. No. 12/180,499 file history dated Jul. 25, 2008; 67 pgs.
U.S. Appl. No. 12/180,486 file history dated Jul. 25, 2008; 65 pgs.
International Search Report PCT/US2009/030406 dated Sep. 29, 2009; 5 pages.
International Search Report and Written Opinion PCT/US2009/034445 dated Oct. 12, 2009; 7 pages.
Office Action U.S. Appl. No. 12/041,054 dated Oct. 27, 2010; 15 pages.
Office Action U.S. Appl. No. 12/041,062 dated Oct. 28, 2010; 12 pages.
International Search Report PCT/US2009/034444 dated Sep. 18, 2009; 2 pages.
Office Action U.S. Appl. No. 12/041,088 dated Oct. 4, 2010; 18 pages.
U.S. Appl. No. 11/952,007, filed Dec. 6, 2007, Davis.
U.S. Appl. No. 11/958,157, filed Dec. 17, 2007, Hayashi.
U.S. Appl. No. 11/952,875, filed Dec. 7, 2007, Davis.
U.S. Appl. No. 11/960,368, filed Dec. 19, 2007, Madsen.
U.S. Appl. No. 11/953,454, filed Dec. 10, 2007, Davis.
U.S. Appl. No. 11/953,494, filed Dec. 10, 2007, Davis.
U.S. Appl. No. 12/236,668, filed Sep. 24, 2008, Davis.
U.S. Appl. No. 12/059,594, filed Mar. 31, 2008, Martinez.
U.S. Appl. No. 12/057,878, filed Mar. 28, 2008, Martinez.
U.S. Appl. No. 12/057,943, filed Mar. 28, 2008, Martinez.
U.S. Appl. No. 11/969,751, filed Jan. 4, 2008, Martinez.
U.S. Appl. No. 12/145,145, filed Jun. 24, 2008, Davis.
U.S. Appl. No. 12/163,249, filed Jun. 27, 2008, Kalaboukis.
U.S. Appl. No. 12/182,969, filed Jul. 30, 2008, Higgins.
U.S. Appl. No. 12/182,813, filed Jul. 30, 2008, Higgins.
U.S. Appl. No. 12/163,314, filed Jun. 27, 2008, Higgins.
U.S. Appl. No. 12/163,396, filed Jun. 27, 2008, Higgins.
U.S. Appl. No. 12/195,969, filed Aug. 21, 2008, Martinez.
U.S. Appl. No. 12/234,000, filed Sep. 19, 2008, Martinez.
U.S. Appl. No. 12/241,590, filed Sep. 30, 2008, Athsani.
U.S. Appl. No. 12/241,687, filed Sep. 30, 2008, Davis.
U.S. Appl. No. 12/206,172, filed Sep. 8, 2008, Higgins.
U.S. Appl. No. 12/273,291, filed Nov. 18, 2008, Nair.
U.S. Appl. No. 12/273,317, filed Nov. 18, 2008, Nair.
U.S. Appl. No. 12/241,198, filed Sep. 30, 2008, Higgins.
U.S. Appl. No. 12/273,259, filed Nov. 18, 2008, Martinez.
U.S. Appl. No. 12/339,355, filed Dec. 19, 2008, Higgins.
U.S. Appl. No. 12/329,038, filed Dec. 5, 2008, Higgins.
U.S. Appl. No. 12/326,553, filed Dec. 2, 2008, Churchill.
U.S. Appl. No. 12/242,656, filed Sep. 30, 2008, Burgener.
U.S. Appl. No. 12/273,371, filed Nov. 18, 2008, Nair.
U.S. Appl. No. 12/357,311, filed Jan. 21, 2009, Higgins.
U.S. Appl. No. 12/357,332, filed Jan. 21, 2009, Higgins.
U.S. Appl. No. 12/357,345, filed Jan. 21, 2009, Higgins.
U.S. Appl. No. 12/357,285, filed Jan. 21, 2009, Higgins.

* cited by examiner

SYSTEM AND METHOD FOR DATA PRIVACY IN URL BASED CONTEXT QUERIES

This application includes material which is subject to copyright protection. The copyright owner has no objection to the facsimile reproduction by anyone of the patent disclosure, as it appears in the Patent and Trademark Office files or records, but otherwise reserves all copyright rights whatsoever.

FIELD OF THE INVENTION

The present invention relates to systems and methods for querying data over the Internet and, more particularly, to systems and methods for URL based context queries.

BACKGROUND OF THE INVENTION

A great deal of information is generated when people use electronic devices, such as when people use mobile phones and cable set-top boxes. Such information, such as location, applications used, social network, physical and online locations visited, to name a few, could be used to deliver useful services and information to end users, and provide commercial opportunities to advertisers and retailers. However, most of this information is effectively abandoned due to deficiencies in the way such information can be captured. For example, and with respect to a mobile phone, information is generally not gathered while the mobile phone is idle (i.e., not being used by a user). Other information, such as presence of others in the immediate vicinity, time and frequency of messages to other users, and activities of a user's social network are also not captured effectively.

SUMMARY OF THE INVENTION

In one embodiment, the invention is a method. A reference to a data object is received from a user. At least one entity that controls the data object is identified via the network. At least one permission for the data object is retrieved via the network, wherein the permission is associated with the entity that controls the data object. It is then determined, via the network, if the user is permitted to access to the data object using the permission for the data object and spatial data, temporal data social data and logical data available to the network that relates to the user and to the permission for the data object. If the user is permitted access to the data object, access is granted to the data object, and if the user is nor permitted access to the data object, access is denied to the data object.

In another embodiment, the invention is a system comprising: an object reference receiving module that receives references to data objects from users; a controlling entity identification module that identifies, for each reference to a data object received by the object reference receiving module, at least one entity that controls the data object; a permission retrieval module that retrieves, for each reference to a data object received by the object reference receiving module and processed by the permission retrieval module, at least one permission for the data object, wherein the at least one permission is associated with the at least entity that controls the data object; a permission determination module that determines, via the network, for each reference to a data object received by the object reference receiving module and processed by the permission retrieval module and the permission retrieval module, if the user associated with the reference to a data object is permitted to access to the data object using the at least one permission for the data object and spatial data, temporal data social data and logical data available to the network that relates to the user and to the at least one permission for the data object, wherein if the user is permitted access to the data object, access is granted to the data object, and if the user is nor permitted access to the data object, access is denied to the data object.

BRIEF DESCRIPTION OF THE DRAWINGS

The foregoing and other objects, features, and advantages of the invention will be apparent from the following more particular description of preferred embodiments as illustrated in the accompanying drawings, in which reference characters refer to the same parts throughout the various views. The drawings are not necessarily to scale, emphasis instead being placed upon illustrating principles of the invention.

DETAILED DESCRIPTION

Figure 1:
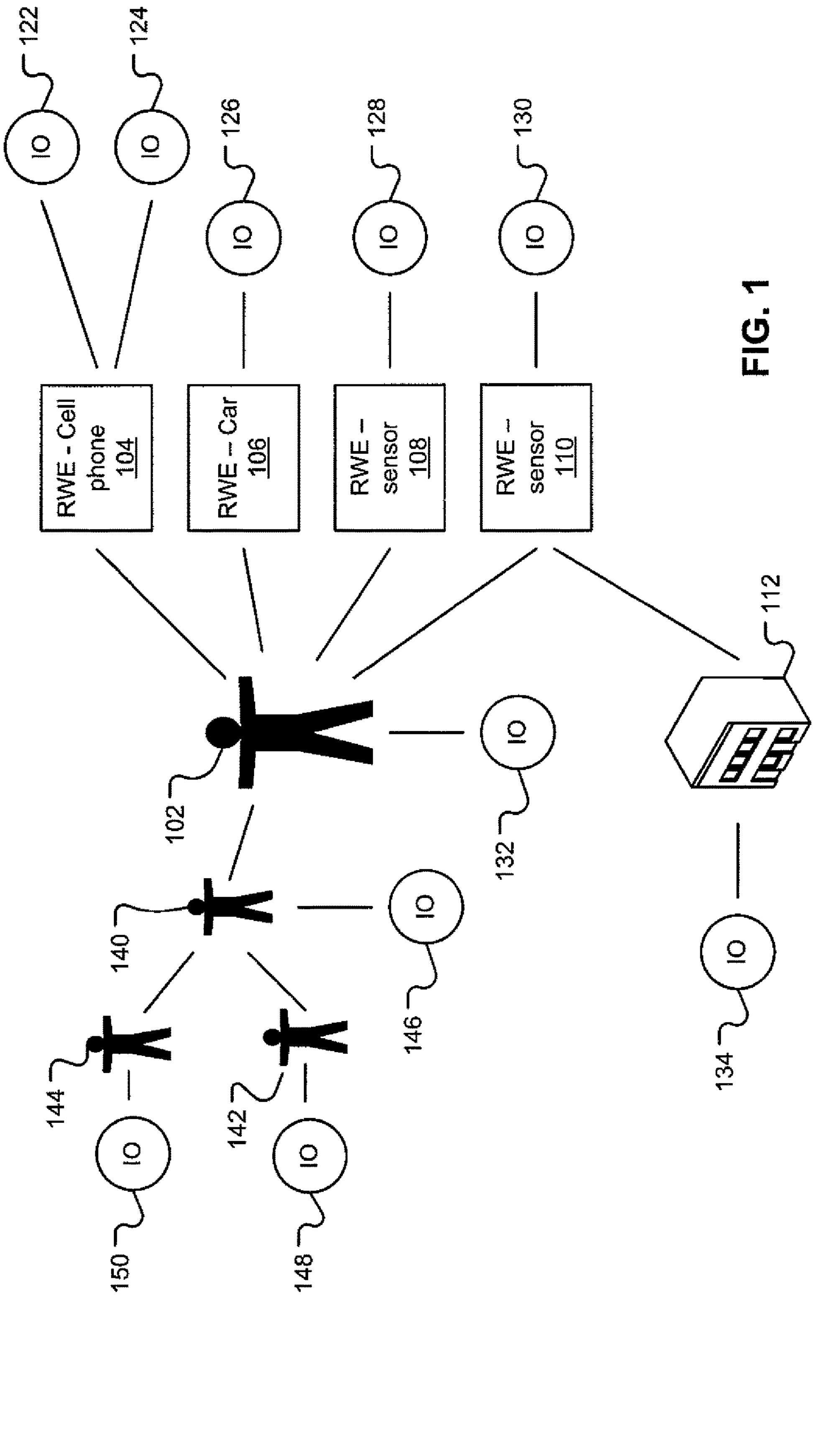
FIG. 1 illustrates relationships between real-world entities (RWE) and information objects (IO) on one embodiment of a W4 Communications Network (W4 COMN.)

The present invention is described below with reference to block diagrams and operational illustrations of methods and devices to select and present media related to a specific topic. It is understood that each block of the block diagrams or operational illustrations, and combinations of blocks in the block diagrams or operational illustrations, can be implemented by means of analog or digital hardware and computer program instructions.

These computer program instructions can be provided to a processor of a general purpose computer, special purpose computer, ASIC, or other programmable data processing apparatus, such that the instructions, which execute via the processor of the computer or other programmable data processing apparatus, implements the functions/acts specified in the block diagrams or operational block or blocks.

In some alternate implementations, the functions/acts noted in the blocks can occur out of the order noted in the operational illustrations. For example, two blocks shown in succession can in fact be executed substantially concurrently or the blocks can sometimes be executed in the reverse order, depending upon the functionality/acts involved.

For the purposes of this disclosure the term "server" should be understood to refer to a service point which provides processing, database, and communication facilities. By way of example, and not limitation, the term "server" can refer to a single, physical processor with associated communications and data storage and database facilities, or it can refer to a networked or clustered complex of processors and associated network and storage devices, as well as operating software and one or more database systems and applications software which support the services provided by the server.

For the purposes of this disclosure the term "end user" or "user" should be understood to refer to a consumer of data supplied by a data provider. By way of example, and not limitation, the term "end user" can refer to a person who receives data provided by the data provider over the Internet in a browser session, or can refer to an automated software application which receives the data and stores or processes the data.

For the purposes of this disclosure the term "media" and "media content" should be understood to refer to binary data which contains content which can be of interest to an end user. By way of example, and not limitation, the term "media" and "media content" can refer to multimedia data, such as video data or audio data, or any other form of data capable of being transformed into a form perceivable by an end user. Such data can, furthermore, be encoded in any manner currently known, or which can be developed in the future, for specific purposes. By way of example, and not limitation, the data can be encrypted, compressed, and/or can contained embedded metadata.

For the purposes of this disclosure, a computer readable medium stores computer data in machine readable form. By way of example, and not limitation, a computer readable medium can comprise computer storage media and communication media. Computer storage media includes volatile and non-volatile, removable and non-removable media implemented in any method or technology for storage of information such as computer-readable instructions, data structures, program modules or other data. Computer storage media includes, but is not limited to, RAM, ROM, EPROM, EEPROM, flash memory or other solid-state memory technology, CD-ROM, DVD, or other optical storage, magnetic cassettes, magnetic tape, magnetic disk storage or other mass storage devices, or any other medium which can be used to store the desired information and which can be accessed by the computer.

For the purposes of this disclosure a module is a software, hardware, or firmware (or combinations thereof) system, process or functionality, or component thereof, that performs or facilitates the processes, features, and/or functions described herein (with or without human interaction or augmentation). A module can include sub-modules. Software components of a module may be stored on a computer readable medium. Modules may be integral to one or more servers, or be loaded and executed by one or more servers. One or more modules may grouped into an engine or an application.

For the purposes of this disclosure an engine is a software, hardware, or firmware (or combinations thereof) system, process or functionality that performs or facilitates the processes, features, and/or functions described herein (with or without human interaction or augmentation).

Embodiments of the present invention utilize information provided by a network which is capable of providing data collected and stored by multiple devices on a network. Such information may include, without limitation, temporal information, spatial information, and user information relating to a specific user or hardware device. User information may include, without limitation, user demographics, user preferences, user social networks, and user behavior. One embodiment of such a network is a W4 Communications Network.

A "W4 Communications Network" or W4 COMN, provides information related to the "Who, What, When and Where" of interactions within the network. In one embodiment, the W4 COMN is a collection of users, devices and processes that foster both synchronous and asynchronous communications between users and their proxies providing an instrumented network of sensors providing data recognition and collection in real-world environments about any subject, location, user or combination thereof.

In one embodiment, the W4 COMN can handle the routing/addressing, scheduling, filtering, prioritization, replying, forwarding, storing, deleting, privacy, transacting, triggering of a new message, propagating changes, transcoding and linking. Furthermore, these actions can be performed on any communication channel accessible by the W4 COMN.

In one embodiment, the W4 COMN uses a data modeling strategy for creating profiles for not only users and locations, but also any device on the network and any kind of user-defined data with user-specified conditions. Using Social, Spatial, Temporal and Logical data available about a specific user, topic or logical data object, every entity known to the W4 COMN can be mapped and represented against all other known entities and data objects in order to create both a micro graph for every entity as well as a global graph that relates all known entities with one another. In one embodiment, such relationships between entities and data objects are stored in a global index within the W4 COMN.

In one embodiment, a W4 COMN network relates to what may be termed "real-world entities", hereinafter referred to as RWEs. A RWE refers to, without limitation, a person, device, location, or other physical thing known to a W4 COMN. In one embodiment, each RWE known to a W4 COMN is assigned a unique W4 identification number that identifies the RWE within the W4 COMN.

RWEs can interact with the network directly or through proxies, which can themselves be RWEs. Examples of RWEs that interact directly with the W4 COMN include any device such as a sensor, motor, or other piece of hardware connected to the W4 COMN in order to receive or transmit data or control signals. RWE may include all devices that can serve as network nodes or generate, request and/or consume data in a networked environment or that can be controlled through a network. Such devices include any kind of "dumb" device purpose-designed to interact with a network (e.g., cell phones, cable television set top boxes, fax machines, telephones, and radio frequency identification (RFID) tags, sensors, etc.).

Examples of RWEs that may use proxies to interact with W4 COMN network include non-electronic entities including physical entities, such as people, locations (e.g., states, cities, houses, buildings, airports, roads, etc.) and things (e.g., animals, pets, livestock, gardens, physical objects, cars, airplanes, works of art, etc.), and intangible entities such as business entities, legal entities, groups of people or sports teams. In addition, "smart" devices (e.g., computing devices such as smart phones, smart set top boxes, smart cars that support communication with other devices or networks, laptop computers, personal computers, server computers, satellites, etc.) may be considered RWE that use proxies to interact with the network, where software applications executing on the device that serve as the devices' proxies.

In one embodiment, a W4 COMN may allow associations between RWEs to be determined and tracked. For example, a given user (an RWE) can be associated with any number and type of other RWEs including other people, cell phones, smart credit cards, personal data assistants, email and other communication service accounts, networked computers, smart appliances, set top boxes and receivers for cable television and other media services, and any other networked device. This association can be made explicitly by the user, such as when the RWE is installed into the W4 COMN.

An example of this is the set up of a new cell phone, cable television service or email account in which a user explicitly identifies an RWE (e.g., the user's phone for the cell phone service, the user's set top box and/or a location for cable service, or a username and password for the online service) as being directly associated with the user. This explicit association can include the user identifying a specific relationship between the user and the RWE (e.g., this is my device, this is my home appliance, this person is my friend/father/son/etc., this device is shared between me and other users, etc.). RWEs can also be implicitly associated with a user based on a current situation. For example, a weather sensor on the W4 COMN can be implicitly associated with a user based on information indicating that the user lives or is passing near the sensor's location.

In one embodiment, a W4 COMN network may additionally include what may be termed "information-objects", hereinafter referred to as IOs. An information object (IO) is a logical object that may store, maintain, generate or otherwise provides data for use by RWEs and/or the W4 COMN. In one embodiment, data within in an IO can be revised by the act of an RWE An IO within in a W4 COMN can be provided a unique W4 identification number that identifies the IO within the W4 COMN.

In one embodiment, IOs include passive objects such as communication signals (e.g., digital and analog telephone signals, streaming media and interprocess communications), email messages, transaction records, virtual cards, event records (e.g., a data file identifying a time, possibly in combination with one or more RWEs such as users and locations, that can further be associated with a known topic/activity/significance such as a concert, rally, meeting, sporting event, etc.), recordings of phone calls, calendar entries, web pages, database entries, electronic media objects (e.g., media files containing songs, videos, pictures, images, audio messages, phone calls, etc.), electronic files and associated metadata.

In one embodiment, IOs include any executing process or application that consumes or generates data such as an email communication application (such as OUTLOOK by MICROSOFT, or YAHOO! MAIL by YAHOO!), a calendaring application, a word processing application, an image editing application, a media player application, a weather monitoring application, a browser application and a web page server application. Such active IOs can or can not serve as a proxy for one or more RWEs. For example, voice communication software on a smart phone can serve as the proxy for both the smart phone and for the owner of the smart phone.

In one embodiment, for every IO there are at least three classes of associated RWEs. The first is the RWE that owns or controls the IO, whether as the creator or a rights holder (e.g., an RWE with editing rights or use rights to the IO). The second is the RWE(s) that the IO relates to, for example by containing information about the RWE or that identifies the RWE. The third are any RWEs that access the IO in order to obtain data from the IO for some purpose.

Within the context of a W4 COMN, "available data" and "W4 data" means data that exists in an IO or data that can be collected from a known IO or RWE such as a deployed sensor. Within the context of a W4 COMN, "sensor" means any source of W4 data including PCs, phones, portable PCs or other wireless devices, household devices, cars, appliances, security scanners, video surveillance, RFID tags in clothes, products and locations, online data or any other source of information about a real-world user/topic/thing (RWE) or logic-based agent/process/topic/thing (IO).

FIG. 1 illustrates one embodiment of relationships between RWEs and IOs on a W4 COMN. A user 102 is a RWE provided with a unique network ID. The user 102 may be a human that communicates with the network using proxy devices 104, 106, 108, 110 associated with the user 102, all of which are RWEs having a unique network ID. These proxies can communicate directly with the W4 COMN or can communicate with the W4 COMN using IOs such as applications executed on or by a proxy device.

In one embodiment, the proxy devices 104, 106, 108, 110 can be explicitly associated with the user 102. For example, one device 104 can be a smart phone connected by a cellular service provider to the network and another device 106 can be a smart vehicle that is connected to the network. Other devices can be implicitly associated with the user 102.

For example, one device 108 can be a "dumb" weather sensor at a location matching the current location of the user's cell phone 104, and thus implicitly associated with the user 102 while the two RWEs 104, 108 are co-located. Another implicitly associated device 110 can be a sensor 110 for physical location 112 known to the W4 COMN. The location 112 is known, either explicitly (through a user-designated relationship, e.g., this is my home, place of employment, parent, etc.) or implicitly (the user 102 is often co-located with the RWE 112 as evidenced by data from the sensor 110 at that location 112), to be associated with the first user 102.

The user 102 can be directly associated with one or more persons 140, and indirectly associated with still more persons 142, 144 through a chain of direct associations. Such associations can be explicit (e.g., the user 102 can have identified the associated person 140 as his/her father, or can have identified the person 140 as a member of the user's social network) or implicit (e.g., they share the same address). Tracking the associations between people (and other RWEs as well) allows the creation of the concept of "intimacy", where intimacy may be defined as a measure of the degree of association between two people or RWEs. For example, each degree of removal between RWEs can be considered a lower level of intimacy, and assigned lower intimacy score. Intimacy can be based solely on explicit social data or can be expanded to include all W4 data including spatial data and temporal data.

In one embodiment, each RWE 102, 104, 106, 108, 110, 112, 140, 142, 144 of a W4 COMN can be associated with one or more IOs as shown. FIG. 1 illustrates two IOs 122, 124 as associated with the cell phone device 104. One IO 122 can be a passive data object such as an event record that is used by scheduling/calendaring software on the cell phone, a contact IO used by an address book application, a historical record of a transaction made using the device 104 or a copy of a message sent from the device 104. The other IO 124 can be an active software process or application that serves as the device's proxy to the W4 COMN by transmitting or receiving data via the W4 COMN. Voice communication software, scheduling/calendaring software, an address book application or a text messaging application are all examples of IOs that can communicate with other IOs and RWEs on the network. IOs may additionally relate to topics of interest to one or more RWEs, such topics including, without limitation, musical artists, genre of music, a location and so forth.

The IOs 122, 124 can be locally stored on the device 104 or stored remotely on some node or datastore accessible to the W4 COMN, such as a message server or cell phone service datacenter. The IO 126 associated with the vehicle 108 can be an electronic file containing the specifications and/or current status of the vehicle 108, such as make, model, identification number, current location, current speed, current condition, current owner, etc. The IO 128 associated with sensor 108 can identify the current state of the subject(s) monitored by the sensor 108, such as current weather or current traffic. The IO 130 associated with the cell phone 110 can be information in a database identifying recent calls or the amount of charges on the current bill.

RWEs which can only interact with the W4 COMN through proxies, such as people 102, 140, 142, 144, computing devices 104, 106 and locations 112, can have one or more IOs 132, 134, 146, 148, 150 directly associated with them which contain RWE-specific information for the associated RWE. For example, IOs associated with a person 132, 146, 148, 150 can include a user profile containing email addresses, telephone numbers, physical addresses, user preferences, identification of devices and other RWEs associated with the user. The IOs may additionally include records of the user's past interactions with other RWEs on the W4 COMN (e.g., transaction records, copies of messages, listings of time and location combinations recording the user's whereabouts in the past), the unique W4 COMN identifier for the location and/or any relationship information (e.g., explicit user-designations of the user's relationships with relatives, employers, co-workers, neighbors, service providers, etc.).

Another example of IOs associated with a person 132, 146, 148, 150 includes remote applications through which a person can communicate with the W4 COMN such as an account with a web-based email service such as Yahoo! Mail. A location's IO 134 can contain information such as the exact coordinates of the location, driving directions to the location, a classification of the location (residence, place of business, public, non-public, etc.), information about the services or products that can be obtained at the location, the unique W4 COMN identifier for the location, businesses located at the location, photographs of the location, etc.

In one embodiment, RWEs and IOs are correlated to identify relationships between them. RWEs and IOs may be correlated using metadata. For example, if an IO is a music file, metadata for the file can include data identifying the artist, song, etc., album art, and the format of the music data. This metadata can be stored as part of the music file or in one or more different IOs that are associated with the music file or both. W4 metadata can additionally include the owner of the music file and the rights the owner has in the music file. As another example, if the IO is a picture taken by an electronic camera, the picture can include in addition to the primary image data from which an image can be created on a display, metadata identifying when the picture was taken, where the camera was when the picture was taken, what camera took the picture, who, if anyone, is associated (e.g., designated as the camera's owner) with the camera, and who and what are the subjects of/in the picture. The W4 COMN uses all the available metadata in order to identify implicit and explicit associations between entities and data objects.

Figure 2:
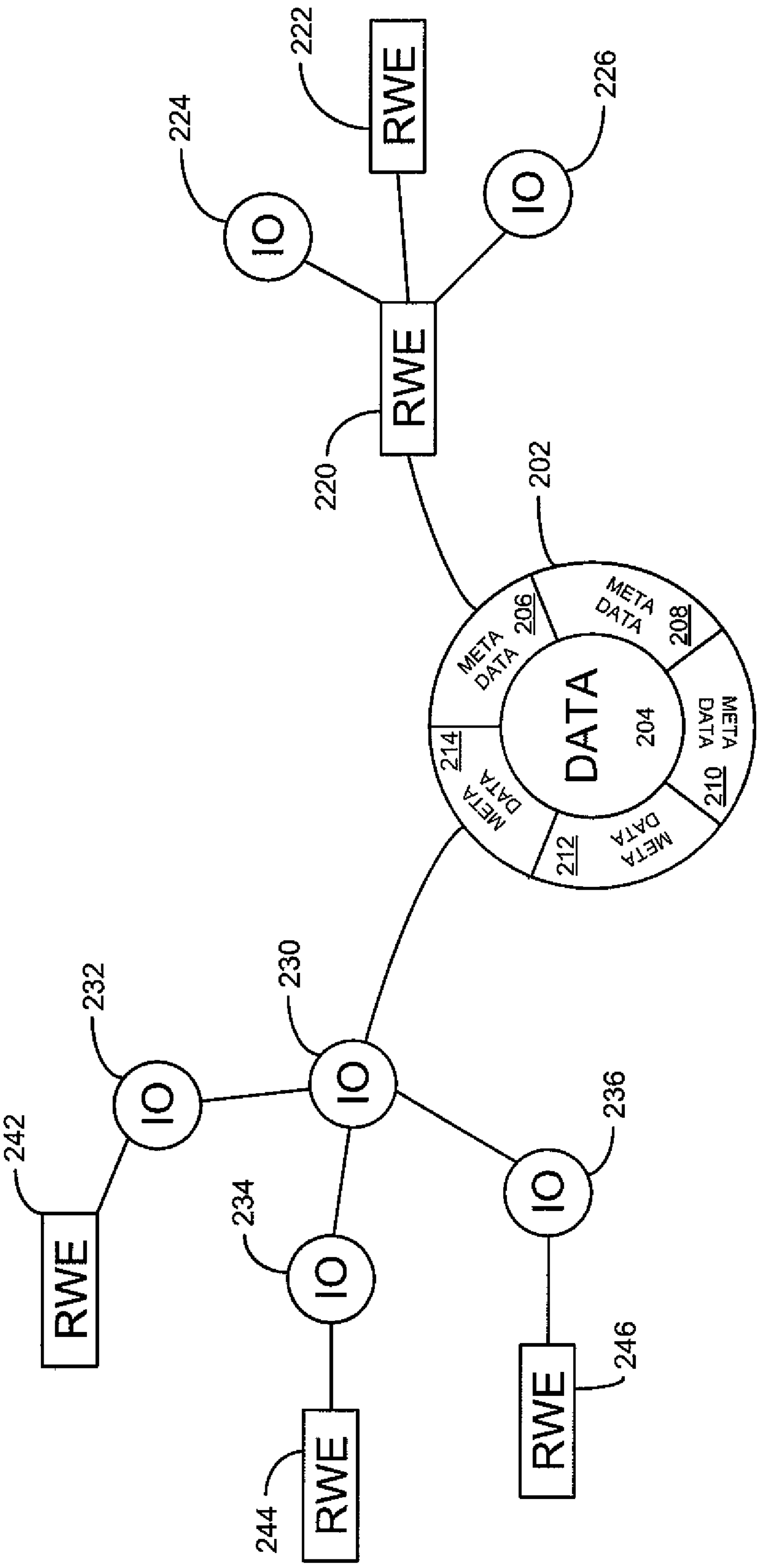
FIG. 2 illustrates metadata defining the relationships between RWEs and IOs on one embodiment of a W4 COMN.

FIG. 2 illustrates one embodiment of metadata defining the relationships between RWEs and IOs on the W4 COMN. In the embodiment shown, an IO 202 includes object data 204 and five discrete items of metadata 206, 208, 210, 212, 214. Some items of metadata 208, 210, 212 can contain information related only to the object data 204 and unrelated to any other IO or RWE. For example, a creation date, text or an image that is to be associated with the object data 204 of the IO 202.

Some of items of metadata 206, 214, on the other hand, can identify relationships between the IO 202 and other RWEs and IOs. As illustrated, the IO 202 is associated by one item of metadata 206 with an RWE 220 that RWE 220 is further associated with two IOs 224, 226 and a second RWE 222 based on some information known to the W4 COMN. For example, could describe the relations between an image (IO 202) containing metadata 206 that identifies the electronic camera (the first RWE 220) and the user (the second RWE 224) that is known by the system to be the owner of the camera 220. Such ownership information can be determined, for example, from one or another of the IOs 224, 226 associated with the camera 220.

FIG. 2 also illustrates metadata 214 that associates the IO 202 with another IO 230. This IO 230 is itself associated with three other IOs 232, 234, 236 that are further associated with different RWEs 242, 244, 246. This part of FIG. 2, for example, could describe the relations between a music file (IO 202) containing metadata 206 that identifies the digital rights file (the first IO 230) that defines the scope of the rights of use associated with this music file 202. The other IOs 232, 234, 236 are other music files that are associated with the rights of use and which are currently associated with specific owners (RWEs 242, 244, 246).

Figure 3:
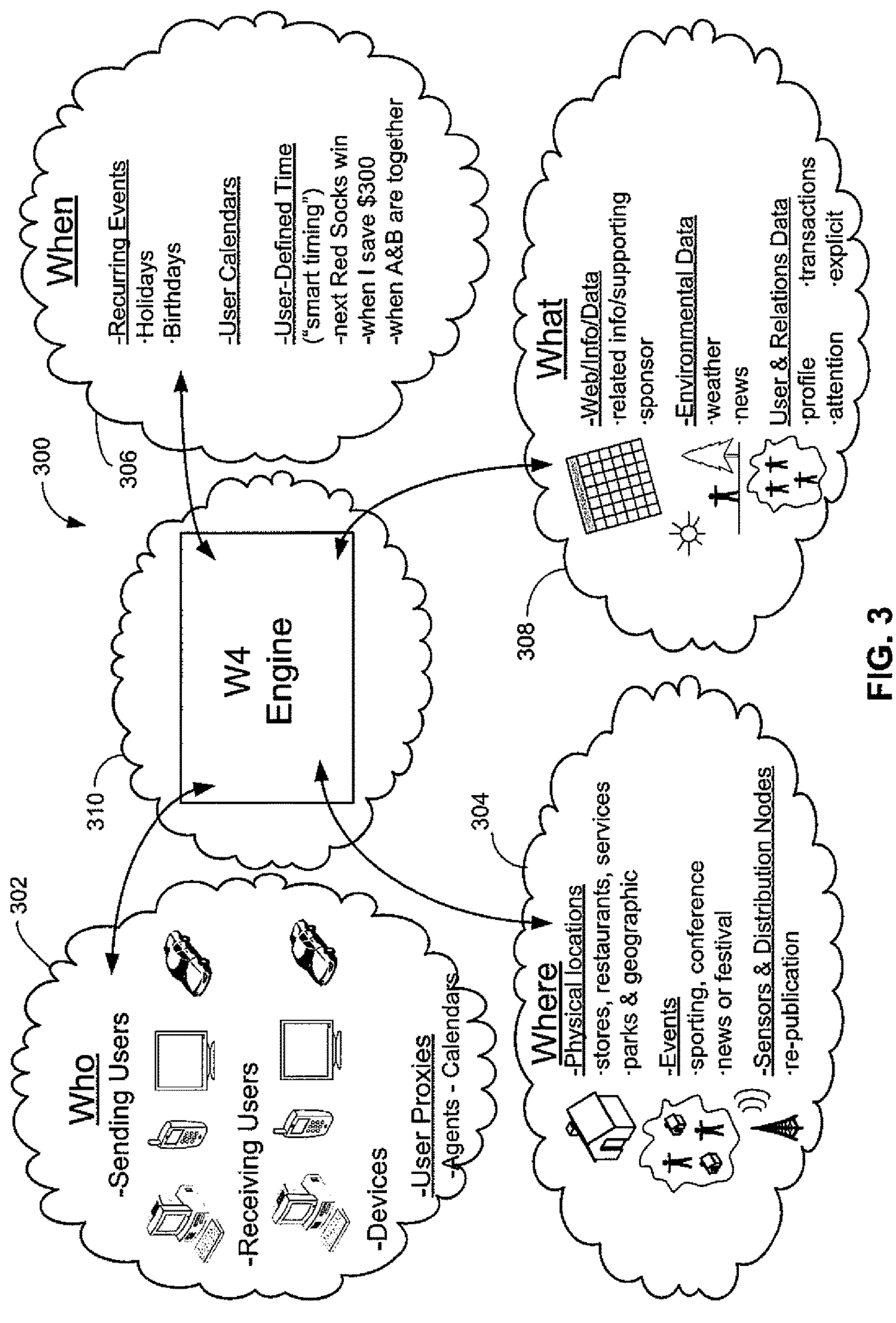
FIG. 3 illustrates a conceptual model of one embodiment of a W4 COMN.

FIG. 3 illustrates one embodiment of a conceptual model of a W4 COMN. The W4 COMN 300 creates an instrumented messaging infrastructure in the form of a global logical network cloud conceptually sub-divided into networked-clouds for each of the 4Ws: Who, Where, What and When. In the Who cloud 302 are all users whether acting as senders, receivers, data points or confirmation/certification sources as well as user proxies in the forms of user-program processes, devices, agents, calendars, etc.

In the Where cloud 304 are all physical locations, events, sensors or other RWEs associated with a spatial reference point or location. The When cloud 306 is composed of natural temporal events (that is events that are not associated with particular location or person such as days, times, seasons) as well as collective user temporal events (holidays, anniversaries, elections, etc.) and user-defined temporal events (birthdays, smart-timing programs).

The What cloud 308 is comprised of all known data—web or private, commercial or user—accessible to the W4 COMN, including for example environmental data like weather and news, RWE-generated data, IOs and IO data, user data, models, processes and applications. Thus, conceptually, most data is contained in the What cloud 308.

Some entities, sensors or data may potentially exist in multiple clouds either disparate in time or simultaneously. Additionally, some IOs and RWEs can be composites in that they combine elements from one or more clouds. Such composites can be classified as appropriate to facilitate the determination of associations between RWEs and IOs. For example, an event consisting of a location and time could be equally classified within the When cloud 306, the What cloud 308 and/or the Where cloud 304.

In one embodiment, a W4 engine 310 is center of the W4 COMN's intelligence for making all decisions in the W4 COMN. The W4 engine 310 controls all interactions between each layer of the W4 COMN and is responsible for executing any approved user or application objective enabled by W4 COMN operations or interoperating applications. In an embodiment, the W4 COMN is an open platform with standardized, published APIs for requesting (among other things) synchronization, disambiguation, user or topic addressing, access rights, prioritization or other value-based ranking, smart scheduling, automation and topical, social, spatial or temporal alerts.

One function of the W4 COMN is to collect data concerning all communications and interactions conducted via the W4 COMN, which can include storing copies of IOs and information identifying all RWEs and other information related to the IOs (e.g., who, what, when, where information). Other data collected by the W4 COMN can include information about the status of any given RWE and IO at any given time, such as the location, operational state, monitored conditions (e.g., for an RWE that is a weather sensor, the current weather conditions being monitored or for an RWE that is a cell phone, its current location based on the cellular towers it is in contact with) and current status.

The W4 engine 310 is also responsible for identifying RWEs and relationships between RWEs and IOs from the data and communication streams passing through the W4 COMN. The function of identifying RWEs associated with or implicated by IOs and actions performed by other RWEs may be referred to as entity extraction. Entity extraction can include both simple actions, such as identifying the sender and receivers of a particular IO, and more complicated analyses of the data collected by and/or available to the W4 COMN, for example determining that a message listed the time and location of an upcoming event and associating that event with the sender and receiver(s) of the message based on the context of the message or determining that an RWE is stuck in a traffic jam based on a correlation of the RWE's location with the status of a co-located traffic monitor.

It should be noted that when performing entity extraction from an IO, the IO can be an opaque object with only where only W4 metadata related to the object is visible, but internal data of the IO (i.e., the actual primary or object data contained within the object) are not, and thus metadata extraction is limited to the metadata. Alternatively, if internal data of the IO is visible, it can also be used in entity extraction, e.g. strings within an email are extracted and associated as RWEs to for use in determining the relationships between the sender, user, topic or other RWE or IO impacted by the object or process.

In the embodiment shown, the W4 engine 310 can be one or a group of distributed computing devices, such as a general-purpose personal computers (PCs) or purpose built server computers, connected to the W4 COMN by communication hardware and/or software. Such computing devices can be a single device or a group of devices acting together. Computing devices can be provided with any number of program modules and data files stored in a local or remote mass storage device and local memory (e.g., RAM) of the computing device. For example, as mentioned above, a computing device can include an operating system suitable for controlling the operation of a networked computer, such as the WINDOWS XP or WINDOWS SERVER operating systems from MICROSOFT CORPORATION.

Some RWEs can also be computing devices such as, without limitation, smart phones, web-enabled appliances, PCs, laptop computers, and personal data assistants (PDAs). Computing devices can be connected to one or more communications networks such as the Internet, a publicly switched telephone network, a cellular telephone network, a satellite communication network, a wired communication network such as a cable television or private area network. Computing devices can be connected any such network via a wired data connection or wireless connection such as a wi-fi, a WiMAX (802.36), a Bluetooth or a cellular telephone connection.

Local data structures, including discrete IOs, can be stored on a computer-readable medium (not shown) that is connected to, or part of, any of the computing devices described herein including the W4 engine 310. For example, in one embodiment, the data backbone of the W4 COMN, discussed below, includes multiple mass storage devices that maintain the IOs, metadata and data necessary to determine relationships between RWEs and IOs as described herein.

Figure 4:
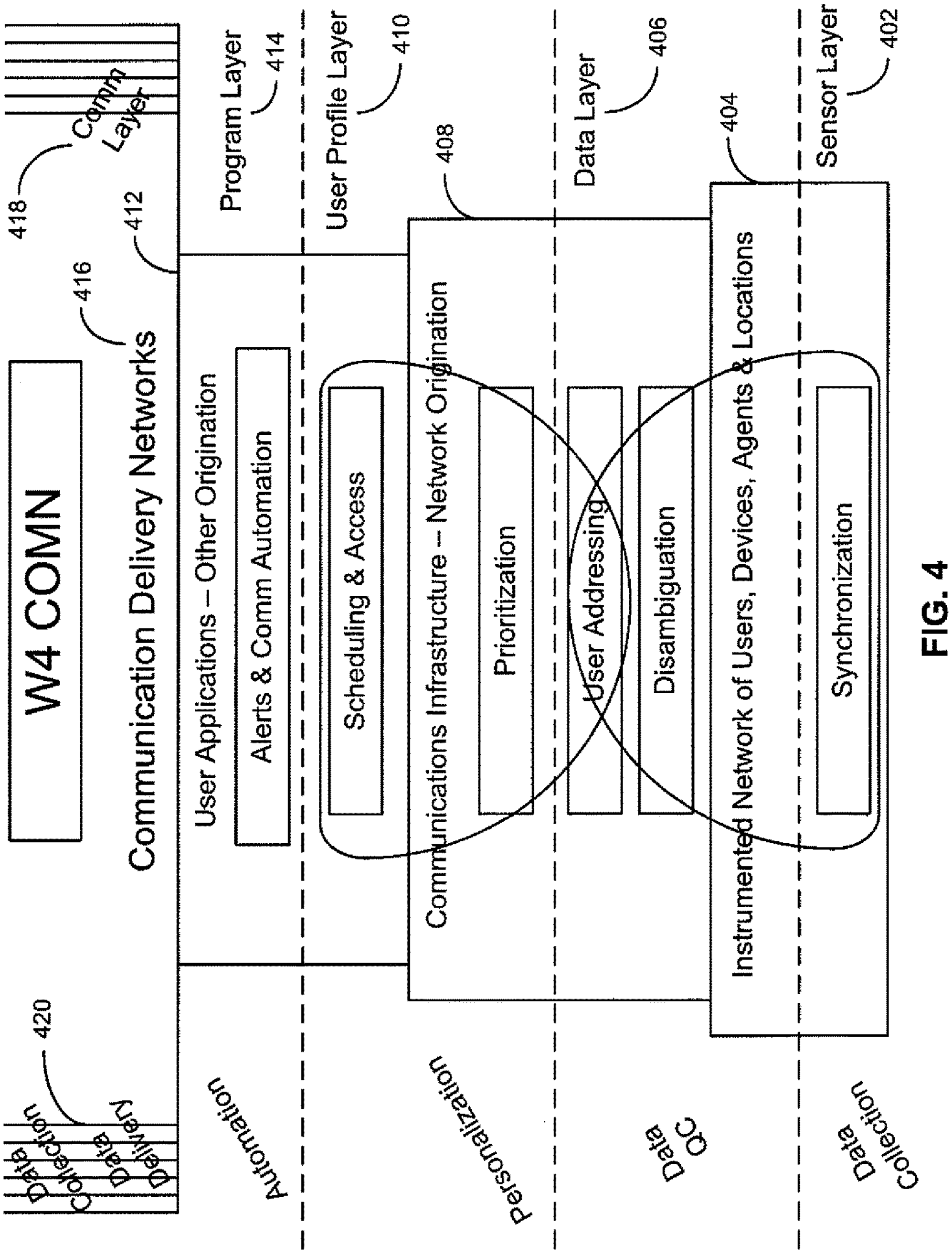
FIG. 4 illustrates the functional layers of one embodiment of the W4 COMN architecture.

FIG. 4 illustrates one embodiment of the functional layers of a W4 COMN architecture. At the lowest layer, referred to as the sensor layer 402, is the network 404 of the actual devices, users, nodes and other RWEs. Sensors include known technologies like web analytics, GPS, cell-tower pings, use logs, credit card transactions, online purchases, explicit user profiles and implicit user profiling achieved through behavioral targeting, search analysis and other analytics models used to optimize specific network applications or functions.

The data layer 406 stores and catalogs the data produced by the sensor layer 402. The data can be managed by either the network 404 of sensors or the network infrastructure 406 that is built on top of the instrumented network of users, devices, agents, locations, processes and sensors. The network infrastructure 408 is the core under-the-covers network infrastructure that includes the hardware and software necessary to receive that transmit data from the sensors, devices, etc. of the network 404. It further includes the processing and storage capability necessary to meaningfully categorize and track the data created by the network 404.

The user profiling layer 410 performs the W4 COMN's user profiling functions. This layer 410 can further be distributed between the network infrastructure 408 and user applications/processes 412 executing on the W4 engine or disparate user computing devices. Personalization is enabled across any single or combination of communication channels and modes including email, IM, texting (SMS, etc.), photo-blogging, audio (e.g. telephone call), video (teleconferencing, live broadcast), games, data confidence processes, security, certification or any other W4 COMM process call for available data.

In one embodiment, the user profiling layer 410 is a logic-based layer above all sensors to which sensor data are sent in the rawest form to be mapped and placed into the W4 COMN data backbone 420. The data (collected and refined, related and deduplicated, synchronized and disambiguated) are then stored in one or a collection of related databases available applications approved on the W4 COMN. Network-originating actions and communications are based upon the fields of the data backbone, and some of these actions are such that they themselves become records somewhere in the backbone, e.g. invoicing, while others, e.g. fraud detection, synchronization, disambiguation, can be done without an impact to profiles and models within the backbone.

Actions originating from outside the network, e.g., RWEs such as users, locations, proxies and processes, come from the applications layer 414 of the W4 COMN. Some applications can be developed by the W4 COMN operator and appear to be implemented as part of the communications infrastructure 408, e.g. email or calendar programs because of how closely they operate with the sensor processing and user profiling layer 410. The applications 412 also serve as a sensor in that they, through their actions, generate data back to the data layer 406 via the data backbone concerning any data created or available due to the applications execution.

In one embodiment, the applications layer 414 can also provide a user interface (UI) based on device, network, carrier as well as user-selected or security-based customizations. Any UI can operate within the W4 COMN if it is instrumented to provide data on user interactions or actions back to the network. In the case of W4 COMN enabled mobile devices, the UI can also be used to confirm or disambiguate incomplete W4 data in real-time, as well as correlation, triangulation and synchronization sensors for other nearby enabled or non-enabled devices.

At some point, the network effects enough enabled devices allow the network to gather complete or nearly complete data (sufficient for profiling and tracking) of a non-enabled device because of its regular intersection and sensing by enabled devices in its real-world location.

Above the applications layer 414, or hosted within it, is the communications delivery network 416. The communications delivery network can be operated by the W4 COMN operator or be independent third-party carrier service. Data may be delivered via synchronous or asynchronous communication. In every case, the communication delivery network 414 will be sending or receiving data on behalf of a specific application or network infrastructure 408 request.

The communication delivery layer 418 also has elements that act as sensors including W4 entity extraction from phone calls, emails, blogs, etc. as well as specific user commands within the delivery network context. For example, "save and prioritize this call" said before end of call can trigger a recording of the previous conversation to be saved and for the W4 entities within the conversation to analyzed and increased in weighting prioritization decisions in the personalization/user profiling layer 410.

Figure 5:
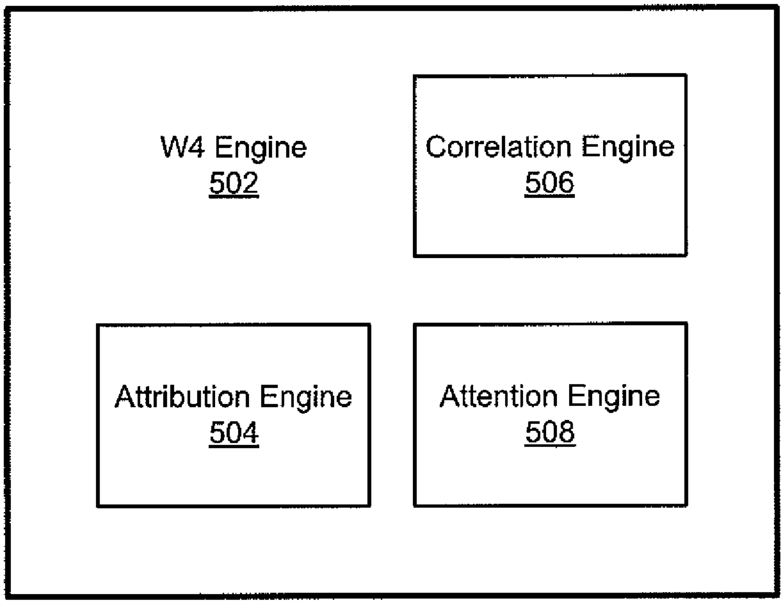
FIG. 5 illustrates the analysis components of one embodiment of a W4 engine as shown in FIG. 2.

FIG. 5 illustrates one embodiment of the analysis components of a W4 engine as shown in FIG. 3. As discussed above, the W4 Engine is responsible for identifying RWEs and relationships between RWEs and IOs from the data and communication streams passing through the W4 COMN.

In one embodiment the W4 engine connects, interoperates and instruments all network participants through a series of sub-engines that perform different operations in the entity extraction process. The attribution engine 504 tracks the real-world ownership, control, publishing or other conditional rights of any RWE in any IO. Whenever a new IO is detected by the W4 engine 502, e.g., through creation or transmission of a new message, a new transaction record, a new image file, etc., ownership is assigned to the IO. The attribution engine 504 creates this ownership information and further allows this information to be determined for each IO known to the W4 COMN.

The correlation engine 506 can operates two capacities: first, to identify associated RWEs and IOs and their relationships (such as by creating a combined graph of any combination of RWEs and IOs and their attributes, relationships and reputations within contexts or situations) and second, as a sensor analytics pre-processor for attention events from any internal or external source.

In one embodiment, the identification of associated RWEs and IOs function of the correlation engine 506 is done by graphing the available data, using, for example, one or more histograms A histogram is a mapping technique that counts the number of observations that fall into various disjoint categories (i.e. bins.). By selecting each IO, RWE, and other known parameters (e.g., times, dates, locations, etc.) as different bins and mapping the available data, relationships between RWEs, IOs and the other parameters can be identified. A histogram of all RWEs and IOs is created, from which correlations based on the graph can be made.

As a pre-processor, the correlation engine 506 monitors the information provided by RWEs in order to determine if any conditions are identified that can trigger an action on the part of the W4 engine 502. For example, if a delivery condition has been associated with a message, when the correlation engine 506 determines that the condition is met, it can transmit the appropriate trigger information to the W4 engine 502 that triggers delivery of the message.

The attention engine 508 instruments all appropriate network nodes, clouds, users, applications or any combination thereof and includes close interaction with both the correlation engine 506 and the attribution engine 504.

Figure 6:
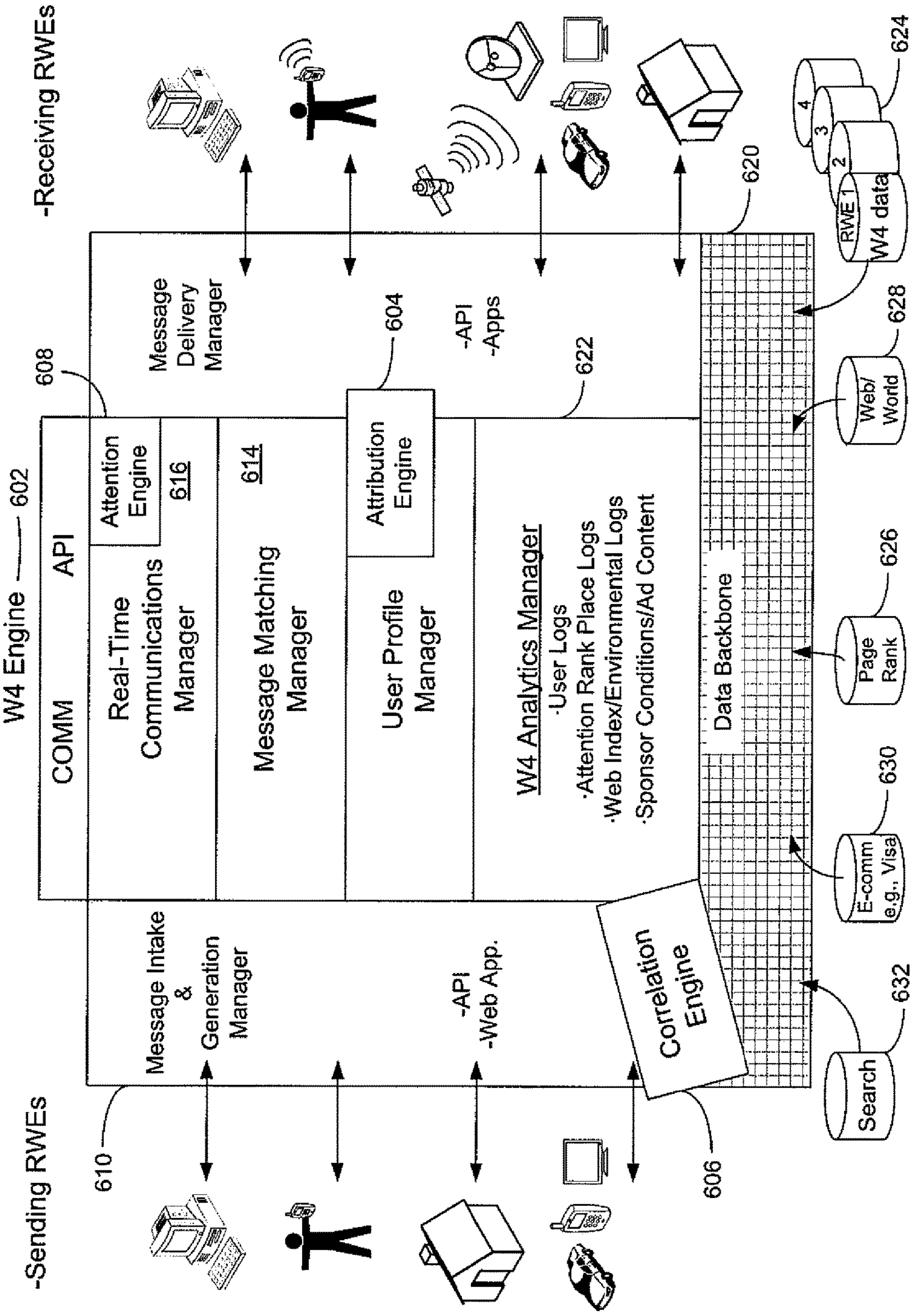
FIG. 6 illustrates one embodiment of a W4 engine showing different components within the sub-engines shown in FIG. 5.

FIG. 6 illustrates one embodiment of a W4 engine showing different components within the sub-engines described above with reference to FIG. 4. In one embodiment the W4 engine 602 includes an attention engine 608, attribution engine 604 and correlation engine 606 with several sub-managers based upon basic function.

The attention engine 608 includes a message intake and generation manager 610 as well as a message delivery manager 612 that work closely with both a message matching manager 614 and a real-time communications manager 616 to deliver and instrument all communications across the W4 COMN.

The attribution engine 604 works within the user profile manager 618 and in conjunction with all other modules to identify, process/verify and represent ownership and rights information related to RWEs, IOs and combinations thereof.

The correlation engine 606 dumps data from both of its channels (sensors and processes) into the same data backbone 620 which is organized and controlled by the W4 analytics manager 622. The data backbone 620 includes both aggregated and individualized archived versions of data from all network operations including user logs 624, attention rank place logs 626, web indices and environmental logs 618, e-commerce and financial transaction information 630, search indexes and logs 632, sponsor content or conditionals, ad copy and any and all other data used in any W4COMN process, IO or event. Because of the amount of data that the W4 COMN will potentially store, the data backbone 620 includes numerous database servers and datastores in communication with the W4 COMN to provide sufficient storage capacity.

The data collected by the W4 COMN includes spatial data, temporal data, RWE interaction data, IO content data (e.g., media data), and user data including explicitly-provided and deduced social and relationship data. Spatial data can be any data identifying a location associated with an RWE. For example, the spatial data can include any passively collected location data, such as cell tower data, global packet radio service (GPRS) data, global positioning service (GPS) data, WI-FI data, personal area network data, IP address data and data from other network access points, or actively collected location data, such as location data entered by the user.

Temporal data is time based data (e.g., time stamps) that relate to specific times and/or events associated with a user and/or the electronic device. For example, the temporal data can be passively collected time data (e.g., time data from a clock resident on the electronic device, or time data from a network clock), or the temporal data can be actively collected time data, such as time data entered by the user of the electronic device (e.g., a user maintained calendar).

Logical and IO data refers to the data contained by an IO as well as data associated with the IO such as creation time, owner, associated RWEs, when the IO was last accessed, the topic or subject of the IO (from message content or "re" or subject line, as some examples) etc. For example, an IO may relate to media data. Media data can include any data relating to presentable media, such as audio data, visual data, and audiovisual data. Audio data can be data relating to downloaded music, such as genre, artist, album and the like, and includes data regarding ringtones, ringbacks, media purchased, playlists, and media shared, to name a few. The visual data can be data relating to images and/or text received by the electronic device (e.g., via the Internet or other network). The visual data can be data relating to images and/or text sent from and/or captured at the electronic device.

Audiovisual data can be data associated with any videos captured at, downloaded to, or otherwise associated with the electronic device. The media data includes media presented to the user via a network, such as use of the Internet, and includes data relating to text entered and/or received by the user using the network (e.g., search terms), and interaction with the network media, such as click data (e.g., advertisement banner clicks, bookmarks, click patterns and the like). Thus, the media data can include data relating to the user's RSS feeds, subscriptions, group memberships, game services, alerts, and the like.

The media data can include non-network activity, such as image capture and/or video capture using an electronic device, such as a mobile phone. The image data can include metadata added by the user, or other data associated with the image, such as, with respect to photos, location when the photos were taken, direction of the shot, content of the shot, and time of day, to name a few. Media data can be used, for example, to deduce activities information or preferences information, such as cultural and/or buying preferences information.

Relationship data can include data relating to the relationships of an RWE or IO to another RWE or IO. For example, the relationship data can include user identity data, such as gender, age, race, name, social security number, photographs and other information associated with the user's identity. User identity information can also include e-mail addresses, login names and passwords. Relationship data can further include data identifying explicitly associated RWEs. For example, relationship data for a cell phone can indicate the user that owns the cell phone and the company that provides the service to the phone. As another example, relationship data for a smart car can identify the owner, a credit card associated with the owner for payment of electronic tolls, those users permitted to drive the car and the service station for the car.

Relationship data can also include social network data. Social network data includes data relating to any relationship that is explicitly defined by a user or other RWE, such as data relating to a user's friends, family, co-workers, business relations, and the like. Social network data can include, for example, data corresponding with a user-maintained electronic address book. Relationship data can be correlated with, for example, location data to deduce social network information, such as primary relationships (e.g., user-spouse, user-children and user-parent relationships) or other relationships (e.g., user-friends, user-co-worker, user-business associate relationships). Relationship data also can be utilized to deduce, for example, activities information.

Interaction data can be any data associated with user interaction of the electronic device, whether active or passive. Examples of interaction data include interpersonal communication data, media data, relationship data, transactional data and device interaction data, all of which are described in further detail below. Table 1, below, is a non-exhaustive list including examples of electronic data.

TABLE 1

Examples of Electronic Data

| Spatial Data | Temporal Data | Interaction Data |
|---|---|---|
| Cell tower | Time stamps | Interpersonal |
| GPRS | Local clock | communications |
| GPS | Network clock | Media |

TABLE 1-continued

| Examples of Electronic Data | | |
|---|---|---|
| Spatial Data | Temporal Data | Interaction Data |
| WiFi<br>Personal area network<br>Network access points<br>User input of location<br>Geo-coordinates | User input of time | Relationships<br>Transactions<br>Device interactions |

Interaction data includes communication data between any RWEs that is transferred via the W4 COMN. For example, the communication data can be data associated with an incoming or outgoing short message service (SMS) message, email message, voice call (e.g., a cell phone call, a voice over IP call), or other type of interpersonal communication related to an RWE. Communication data can be correlated with, for example, temporal data to deduce information regarding frequency of communications, including concentrated communication patterns, which can indicate user activity information.

The interaction data can also include transactional data. The transactional data can be any data associated with commercial transactions undertaken by or at the mobile electronic device, such as vendor information, financial institution information (e.g., bank information), financial account information (e.g., credit card information), merchandise information and costs/prices information, and purchase frequency information, to name a few. The transactional data can be utilized, for example, to deduce activities and preferences information. The transactional information can also be used to deduce types of devices and/or services the user owns and/or in which the user can have an interest.

The interaction data can also include device or other RWE interaction data. Such data includes both data generated by interactions between a user and a RWE on the W4 COMN and interactions between the RWE and the W4 COMN. RWE interaction data can be any data relating to an RWE's interaction with the electronic device not included in any of the above categories, such as habitual patterns associated with use of an electronic device data of other modules/applications, such as data regarding which applications are used on an electronic device and how often and when those applications are used. As described in further detail below, device interaction data can be correlated with other data to deduce information regarding user activities and patterns associated therewith. Table 2, below, is a non-exhaustive list including examples of interaction data.

TABLE 2

| Examples of Interaction Data | |
|---|---|
| Type of Data | Example(s) |
| Interpersonal communication data | Text-based communications, such as SMS and e-mail<br>Audio-based communications, such as voice calls, voice notes, voice mail<br>Media-based communications, such as multimedia messaging service (MMS) communications<br>Unique identifiers associated with a communication, such as phone numbers, e-mail addresses, and network addresses |

TABLE 2-continued

| Examples of Interaction Data | |
|---|---|
| Type of Data | Example(s) |
| Media data | Audio data, such as music data (artist, genre, track, album, etc.)<br>Visual data, such as any text, images and video data, including Internet data, picture data, podcast data and playlist data<br>Network interaction data, such as click patterns and channel viewing patterns |
| Relationship data | User identifying information, such as name, age, gender, race, and social security number<br>Social network data |
| Transactional data | Vendors<br>Financial accounts, such as credit cards and banks data<br>Type of merchandise/services purchased<br>Cost of purchases<br>Inventory of purchases |
| Device interaction data | Any data not captured above dealing with user interaction of the device, such as patterns of use of the device, applications utilized, and so forth |

URL Based Query for Retrieving Data Related to a Context

A W4 COMN provides an unbounded, ever evolving, and nearly incomprehensible set of data. The richness of such data is, however, only useful if it can be accessed in a simple and intuitive way. The W4 paradigm suggests a solution. In one embodiment, a W4 query can be expressed as a context based query, that is to say, a query containing who, what, when, and where criteria grouped together in a manner that states or implies relationships between the criteria.

"Who" criteria are persons, devices, or proxies who are related to the ideas embodied in the context. "Who" may be a known person, such as the user or a specific person known by the user. "Who" may also be a list of specific persons, such as the contact list stored on the PDA of a user, the guest list of a party, or persons listed on a user's social network profile as friends. Alternatively, "Who" can be a general description of persons of interest, such as persons who are interested in surfing, single women in their 40's who drive motorcycles and like yoga, men who like football and commute by bus, persons who pass by a billboard more than three times a week and/or customers of a specific restaurant who also drive BMWs.

"What" criteria are objects or topics, concrete or abstract that relate to the ideas embodied in the context. "What" may be a form of media of interest, such as photos, music or videos. "What" may be an object such as a car, a piece of jewelry or other object of shared interest. "What" may be a genre of music or video, such as country or rock. "What" may be subject matter addressed in media, such as love songs or even specific lyrical phrases. Alternatively, "What" may be a mood or atmosphere, such as happy, sad, energetic, or relaxed. As an indicator of topical relevance, "What" criteria are an unbounded set of things determined by human creation, attention and association or tagging.

"When" criteria are temporal constructs such as dates and times which are related to the ideas embodied in the context. "When" may be the current date and time. "When" may also be a specific date and time in the past or the future, or a range of dates and times in the past or the future, such as a duration, e.g. two hours, four weeks, one year. "When" may be a conditional occurrence if specified conditions or criteria are met, e.g. the next time a user initiates a phone call. "When" may be an offset from a specific date, for example, ten days in the past, or an offset from a conditional occurrence, ten days after a mortgage payment is late. Alternatively, “When” can be an event on a calendar, such as a birthday, a season or a holiday, or an event of personal or societal/social importance, such as the last time a favorite sports team won a championship.

“Where” criteria are physical locations which are related to the ideas embodied in the context. “Where” may be a user’s current location. “Where” may be specific places, such as a country, a state, a city, a neighborhood. “Where” may be defined as the location of an event, such as a concert or some other newsworthy occurrence, or alternatively the personal location of a user when they learned of an event, e.g. where were you when you heard about 9/11. Alternatively, “Where” can be a general description of places of interest, such as blues or jazz clubs, or a conditional location depending on the satisfaction or resolution of specified criteria. For example, “where” can be the real-time most popular club for 24-35 year olds, or “where” can be the research lab where breast cancer is finally cured. “Where” can also be defined in relation to a given user, e.g. a user’s most frequently visited restaurants or the set of cities visited by a salesman over the past month.

A system to support context based query of W4 data in a W4 COMN is most useful to the extent that it is generally available to all the devices in the W4 COMN. A simple and logical implementation is to embody context queries comprising “who”, “what”, “when” and “where” criteria in a HTTP URL that can be used by a wide variety of devices over an external network such as the Internet to present context queries to an available query server.

The one embodiment, the basic format of a URL based context query can be expressed as follows:

http://<query server>/<context query> where the <context query> is a query that can contain any “who”, “what”, “when” and “where” criteria. Such a context query URL becomes, in effect, are a pointer into specific spatial, social, temporal, and topical context. Unlike a static pointer, however, the single context query URL effectively points to the most up-to-date collection of content (e.g., Flickr photos, Y! Local venues, upcoming events, blog entries, etc.) related to the context specified in the URL as well as to the co-presence of people and/or objects in the context specified in the query.

The URL context queries can encode the information in a variety of different ways.

Human Readable Context Queries

A human readable context query contains information in a human readable format that allows users to deduce the results without needing to follow the link. In one embodiment, the basic format of a context query can be:

[<who:value>]/[<what:value>]/[<when:value>]/[<where:value>]

Where a context query could contain any combination of “who”, “what”, “when” and “where” criteria. In one embodiment, criteria can implied to be in an independent “AND” relationship. For example:

who:A/where:B/when:C is equivalent to who=A and where=B and when=C

In one embodiment, criteria have standardized attributes, for example, “what” and “where” criteria may have “subject” attributes, who criteria may have “name” attributes, and so forth. Thus a criteria may be stated as <criteria-attribute:value>

In one embodiment, where no attribute is specified, all attributes of a criteria are searched. In one embodiment, each criteria type can be further supplemented with dependant criteria types that qualify a criteria, generally in the format:

<criteria:value>/<dependant criteria:value> where there can be one to many dependant criteria. Dependant criteria can, in general, be used to further select a subset of data within a set of data selected by a criteria. In one embodiment, human readable context query URLs can be subdivided into 3 categories:

(1.) Canonical URL Context Queries:

Canonical URLs contain the context criteria values in a globally unique format. This means that the URLs pointing to specific contexts are also unique. For example, the following URL points to information objects related to “new year” at 11 P.M. on Dec. 31, 2007 from Sunnyvale. “Related” can mean, for example, that the content/objects/people contained within the W4 URL were either tagged with the string “new year” or have been inferred to be related to the concept “new year” which the string is an alias for.

http://w4.yahoo.com/where/United+States/California/Sunnyvale/when/20071231T230000/what/new+year (2.) Aliased/Relative URL Context Queries:

Aliased/Relative URL context queries include aliased and/or relative information in the URL. This means that the results of the query will vary based on the context of the user making the query. Relative URLs are useful for users to query for themselves given their easily understandable and colloquial language, but can be translated into a non-relative (canonical) URL for sharing. This shared non-relative URL can itself be translated again into a new relative URL valid for the other users. For example, consider a query which points to information objects from “home” that were created or updated “yesterday afternoon” by the user.

http://w4.yahoo.com/where/home/when/yesterday/afternoon/who/me

As different users visit this W4 URL at different time the results will vary based on the user, their definition of “home” and the query time.

(3.) Parsed W4 URLs:

Parsed URL context queries are parsed at runtime and the parsed information is dynamically converted into a set of unique criteria. This means that there can be multiple URLs that all point to the same context. It also means that the definition of the context may vary based on the method used to parse the given text. For example, the two following W4 URLs will point to the same context:

http://w4.yahoo.com/where:701+first+avenue,sunnyvale,ca/when:22-april-08/what:yahoo
http://w4.yahoo.com/where:701+first+avenue,94089/when:2008-04-22/what:yahoo Numeric Context Queries Numeric context queries encode the query criteria in specific machine-readable formats within the URL itself. This technique results in unique context queries which are unambiguous and are not subject to change as the human definition of a location or object changes. They are suitable for archival purposes and contain sufficient information to guarantee that the context can be reliably reconstructed. The specifics of how each particular type of information can be numerically encoded are discussed within the sections about each context type. It is also possible that certain embodiments may encrypt the information using any standard encryption techniques (e.g., PGP, RSA, public key, AES, etc.) such that only authorized users can decrypt and use the encoded information.

For example, the following URL context query encodes the following information: polygon covering San Francisco, time from 10 A.M.-2 P.M. on 22 Apr. 2008, with the user specified by a Yahoo ID.

--- http://w4.yahoo.com/-122.40650177,37.7494697571,122.3790893555, 37.7494697571,122.3790893555,37.7862281799,122.40650177, 37.7862281799,122.40650177,37.7494697571/ 20070422T100000/20070422T140000/johndoe- 1a

---

Identifier Context Queries

Identifier context queries do not expose any of the contextual information within the URL itself and instead display only an identifier that points to the context. When someone attempts to access the URL, the target server can first authenticate the user to see if the user has the privileges to view the context, and, if so it looks up the context (in numeric and/or human readable form) associated with the identifier. In some instances, users may have partial privileges to a context to see some portions of the URL while others remain encoded. The advantage of this system is that not only are the information objects obscured from unauthorized users, but even the context referred to in the W4 URL is not readable. Additionally, the Identifier-Based Context queries can be smaller and easier to type in a browser. For example, the following W4 URL could point to any arbitrary context:

http://w4.yahoo.com/djktlec

Context Criteria

Who, what, when and where criteria can be specified in any format that clearly state values the respective criteria can take. The following paragraphs provide examples that are intended to be illustrative, and not limiting.

(1.) Where Criteria (Location Specifications)

Where criteria can be specified in a variety of different ways. Where criteria in canonical context queries consist of text that is directly mapped to a unique point or bounded area in space. In the case of parsed context queries, the input string (e.g., "Sunnyvale, Calif.") is fed into a location parser that returns a point and/or area that the string refers to (e.g. the city limits of Sunnyvale).

It is important to note that in the case of both canonical and parsed location information, it is possible that the definition of a place (e.g., "US/California/Sunnyvale", "Sunnyvale, Calif.") may vary over time. The geopolitical boundaries that define Sunnyvale may shrink, expand or even disappear over time. Therefore the location system may store multiple definitions for a location and use the appropriate location definition based on the context of the query. For example, the query can specify a context that uses boundaries that are existent at the time expressed in the query. For example:

http://w4.yahoo.com/where:Sunnyvale,CA/wheredefine: 2008 specifies a context query requesting information regarding Sunnyvale as it existed in 1998.

As opposed to:

http://w4.yahoo.com/where:Sunnyvale,CA/when:1998 which requests information regarding 1998 using the boundaries of Sunnyvale as they exist over all of time.

It is also possible that the query could express the use of a differing spatial and temporal boundaries, i.e., show the information objects from 2008 that fit within the 1998 definition of Sunnyvale, or alternately, show the information objects from 1998 that fit within the 2008 definition of Sunnyvale. For example:

http://w4.yahoo.com/where:Sunnyvale,CA/wheredefine: 1998/when:2008

Note that this context query illustrates one embodiment of a dependant criteria "wheredefine" that qualifies the "where" criteria to define the appropriate time to use to determine a location boundary.

Numerical location information is important for both numerical context queries and for backend storage in the case of Identifier-Based context queries. Location can be numerically encoded and stored in a variety of ways such as point (37.23, −122.45), point-radius (37.23, −122.45, 1000m), bounding box (−122. 49, 37.74, −122. 41, 37.79), polygon (−122. 40650177, 37.7494697571, 122. 40650177, 37.7494697571, 122.3790893555, 37.7862281799, 122.40650177, 37.7862281799, 122.40650177, 37.7494697571), geotudes (http://www.geotude.com), geohashes (http://geohash.org), woeid (Where On Earth ID), placeids (hashed woeids), cell tower ID, WiFi beacon, Bluetooth beacon, etc.

Another point of contention for location specification is the exact location being defined. Information objects may have multiple locations associated with them. For example a photograph can be referenced by the photographer's location, the subject of the photograph's location (note that photographer and subject location may be very different, for example a photo the White House from the top of the Washington Monument), locations associated with the persons, places or objects associated with the photo or just a single location that could be photographer, subject or associated location. In one embodiment, location queries can specify both kinds of location and the system can to return IOs that fit into the queried context. For example, http://w4.yahoo.com/where-photographer:Berkeley,CA/what:Alcatraz specifies a where criteria using a "photographer" attribute to select photos relating to Alcatraz taken from Berkeley, Calif., as opposed to http://w4.yahoo.com/where-subject:San+Francisco,CA/what:Alcatraz which uses where criteria using a "subject" attribute to select photo subjects in San Francisco, Calif. relating to Alcatraz (perhaps taken from Alcatraz.)

(2.) When Criteria (Time Specifications)

When criteria can be specified in a variety of different ways. In one embodiment, time specifications can take the following formats

- A single date (e.g.: when:22-April-2008)
- Start and end times (e.g.: from:20-APR-2008 and to:1-MAY-2008)
- Support multiple granularities from milliseconds all the way to years or decades
- Periodic times (e.g., Sundays, $4^{th}$ day of month, second Saturday, etc.)
- Event specification (Christmas, Ramadan.)
- Relative dates (yesterday, next week.)
- Specify in both GMT and local time (derived from location context.)

Time values can be expressed in any standardized time format. Some standardized ways to specify numeric times are:

- MySQL datetime (e.g. http://w4.yahoo.com/where: Sunnyvale,CA/when:2008-04-01 11:25:00)

iCal format (e.g. http://w4.yahoo.com/where:Sunnyvale, CA/DTSTART: 19970714T170000Z/DTEND: 19970715T035959Z)

RFC 2445—Internet Calendaring and Scheduling Core Object Specification (http://www.faqs.org/rfcs/rfc2445.html). This specification is an extension of the iCal format and includes significant support for periodic and repeating events.

Coordinated Universal Time (UTC). (e.g. http://w4.yahoo.com/ where:Sunnyvale,CA/when:1997-07-16T19:20:30.45+01:00)

Unix Time. Eg: http://w4.yahoo.com/where:Sunnyvale, CA/when:1095379200.25

Parsed context support and translate between many different types of time specification formats. iCal format and/or the RFC 2445 specification are useful descriptors for canonical, numerical and ID-based URLs.

(3.) Who Criteria (Person Specifications)

Person specification comprises the social aspect of context queries. It allows users to specify social dimensions and contexts from which they would like to receive information objects. The person specification can be done in two ways: a) the returned objects are created by the specified person (e.g., photos taken by Joe); and b) the returned objects are somehow related to the specified person (e.g., photos taken of Joe, photos owned by Joe, photos annotated by Joe, photos shared or re-published by Joe, photos linked or embed by Joe, etc.)

Persons can be specified using any alias, string or identifier that uniquely identifies a person or group of persons having specific attributes. Examples include Yahoo! ID, OpenID, email address, social security number, phone number, etc. In the case of aliased/relative context queries, the system can disambiguate between various persons based on the context of the user—for e.g., the term "Joe" will mean different things to different people and is determined based on the social context of the user that is accessing the URL (e.g. two persons may each have a friend with the first name of "Joe", but different last names, or has one friend named Joe and one co-worker named Joe.)

Users should also be able to specify people within their social networks, address books and contact lists such as "friends", "family", "partner", messenger groups, etc. In the case of a social network based specification such as "friends", the system decodes the user's social graph to understand which users are being specified by the term "friends". It is important to note that social network graphs are also time sensitive—the system keeps time information associated with each node in the graph. For example, the URL http://w4.yahoo.com/where:Sunnyvale,CA/who:friends/who-when:1998/when:2008 shows all the Sunnyvale media objects created in 2008 by the people who were in the users social network in 1998. Note the use of a "who" criteria for a group "friends" and a "who" attribute of "when."

In one embodiment, person specifications also allow the specification of criteria attributes including interests, types and categories. Examples include "all males aged 25-45", "Formula 1 fans", "living in Oakland", etc. For example:

http://w4.yahoo.com/where:Sunnyvale, CA/who-age:25-35/who-sex:male/who-interest:formula1

(4.) What Criteria (Object Specification)

What criteria can be specified in a variety of different ways. This is a particularly broad category and can often include items that can be specified in the other query criteria. Terms that can be listed in the "what" part of a context URL include: (1) real world entities; and (2) topics (which do not necessarily refer to real world entities) or tags (which relate to real world entities or information objects.)

In one embodiment, the primary real world entities to be specified will be uniquely identified world objects ("Golden Gate Bridge" or "Joe's car"), persons ("John Doe"), locations ("Sunnyvale") and events ("Yahoo Party 2007"). The system understands the different properties of each type of object and treats it accordingly. Allowing persons and locations to be referenced in the what dimension allows W4 URLs to specify, for example, content about one person, but created by another, i.e http://w4.yahoo.com/what:Joe/who:Bob describes content created by Bob, but about Joe. The objects can also be specified by canonical textual and/or numeric unique identifiers as described above, by relative non-unique identifiers as described above, or by parsed identifiers as described above. The ability to refer to topics in the "what" part of a context query can also be accomplished by the means described above for referring to real world entities. Alternatively, or additionally, descriptors for topics will be "tags" which are text strings which may or may not resolve to uniquely identified topic or concept. For example:

http://w4.yahoo.com/when:20080420/what:Golden+Gate+Bridge

A specified object within a context query can also be second context query URL. This construct is a essentially a nested subquery and has the general format:

[<criteria:value>]/<query server>/<context query>

Where the nested subquery, <query server>/<context query> is applied to the primary query specified by one to many <criteria:value> pairs. For example, suppose a URL context query, http://w4.yahoo.com/djktlec, defines a context related to the Spanish Grand Prix. If a user is interested in reviews or commentaries or other data relating to the race created on the date of the race in San Francisco, Calif., a context query can be specified as follows. The primary query selects all data from or relating to San Francisco, Calif., on the date of the race, and the subquery selects a subset of such data relating to the race context.

http://w4.yahoo.com/when:20080420/where:San+Francisco/what:w4.yahoo.com/djktlec

Generation of URL-Based Context Queries

In one embodiment, objects (whether IOs or RWEs) in a W4 data store are tagged or indexed by the data's who, what, when and where attributes. For example, an image of a photograph can contain attributes including the photographer (who), the subject (what, e.g. Alcatraz), the location (where, e.g. San Francisco) and the time of creation (when, e.g. Jan. 5, 2008: 2:20 P.M.) Where a set of IOs, RWEs or both contain the same or similar values, the IOs and RWEs can be said to cluster about that value. For example, a set of IOs relating to photographs can cluster about the name of a photographer (who), the year it was taken (when), where the photograph was taken (where), the subject of the photograph (what), or a property of the photograph, such as black and white or color (another what).

Thus, data objects in a W4 COMN or similar network can be said to cluster in an n-dimensional space. In one embodiment, the n-dimensional space is a four-dimensional space with "where", "when", "who" and "what" dimensions or data axes, or stated in another way spatial, temporal, social and topical or logical dimensions. More dimensions are, of course, possible, and as seen above it is common for the "what" dimension to be represented in multiple dimensions depending on the topic or tags purpose. A spatial dimension can, in its most elementary form be expressed as an absolute location in space. Even if spatial dimensions are expressed in a relative format (e.g. a location, a distance from another object, an entity at a point in time), such dimensions can always be resolved to an absolute point or region in real world space. The temporal dimension is not generally multivariate. A temporal dimension can, in its most elementary form be expressed as an absolute time interval. Even if temporal dimensions are expressed in a relative format (i.e. the date of an event, an offset from an event), such dimensions can always be resolved to an interval (or set of intervals in the case of recurring holidays or events) with absolute start and end times.

The "what", or topical dimension is inherently multivariate as it can relate to object attributes that are essentially independent from one another and can relate to objects in multiple classes. For example, a media clip may have topical attributes such as subject, genre, mood, and format (i.e. JPEG, TIFF, FLV and so forth). For example, there are many media clips relating love songs (subject.) The subject of the song, however, likely has no relationship to the format. In one embodiment, every topic attribute can be a data dimension. For example, subject, genre, mood can each be a topical dimension containing multiple object types, such as images, video, and audio clips and so forth. In practice, certain attributes such as subject may be more meaningful as topical dimensions. On the other hand, in one embodiment, disparate topics could be combined in a single "what" dimension as the logical equivalent of <what-attribute>:<value> pairs.

The who or social dimension relates to a single class of objects—persons. In one embodiment, the social dimension can be viewed as a single variable dimension, where every reference can ultimately be resolved to a unique individual or group of unique individuals. Yet a person, unlike a time or a spatial location, may have more complex social attributes, such as family, or friends. Thus, in another embodiment, one social dimension can reflect individuals, another dimension may reflect friends of individuals.

In one embodiment, disparate social dimensions could be combined in a single who dimension of a W4 data space as the logical equivalent of three value pairs:

<who>:<value>,<who-relation>:<value>,<who-relation-who><value> where who is a unique individual, who-relation is a relationship type, and another individual. For example:

<who>:<Joe D.>,<who-relation>:<self>, <who-relation-who>< Joe D.>
<who>:<Joe D.>,<who-relation>:<friend>, <who-relation-who>< Lance.>
<who>:<Joe D.>,<who-relation>:<family>, <who-relation-who>< Jim D.> illustrates how Joe D. could be indexed in single "who" dimension reflecting self, friends and family The foregoing embodiments of the how data relating to RWEs and IOs in a W4 COMN can be organized in a multidimensional data space are intended to be illustrative and not limiting. The following methods can be applied to any data space of 1 to n dimensions.

Once objects in a W4 COMN are located within a multidimensional data space, objects can be clustered within one or more dimensions to reveal relationships between the objects. In one embodiment, objects can be clustered in a multidimensional space using a conceptual distance metric in W4 space. Distance along the "where" axis is relatively easy to define: e.g. Euclidean distance between the centroids of two areas (or more precisely, the length of the great circle segment connecting the two centroids,)

Distance in the "when" dimension can be defined, in one embodiment as simply the amount of time between the midpoints of two intervals (though this can be complicated by the size of the intervals; intervals with the same midpoint are more similar if their endpoints and overall duration are more similar.) In the case of cyclic time, however, even distance in the "when" dimension can have hidden subtleties—is the distance between consecutive Tuesdays less than the distance between the 24th day of consecutive months or less than the distance between a Tuesday and the previous Sunday? One approach to handling cyclic time is to construct a time feature vector in which the time is represented in many ways (e.g. hour of day, segment of day: morning/afternoon/evening, day of week, day of month, etc.). Matching such time vectors produces some similarity between times related only by a few features (e.g. same day of the week) and much similarity between nearby times (times separated by an hour will match day of week, day of month, segment of day, etc.)

A distance metric in the "what" dimension can be constructed based on some notion of semantic distance between topics. In one embodiment, semantic distance can be determined using the hyponym/hypemym and holonym/meronym relationships expressed in a semantic lexicon such as WordNet. It is similarly possible to define a social distance metric along the "who" dimension based on the number of hops in the social graph between two individuals, perhaps even weighting different types of relationship (e.g., distance between siblings is less than distance between coworkers). Though for both "who" and "what", the weightings applied to each edge of the graph are somewhat arbitrary.

As a final complication, defining distance over multiple dimensions is exceedingly difficult—are events separated by hours closer to one another than events separated by kilometers? Given enough training data (i.e. a large quantity of W4 data clustered or grouped into subjectively good groups) weightings can be determined for graph edges and can be used to determine some weights that allow computation of relative distance across multiple dimensions.

The task of clustering in data W4 space can be simplified by first clustering along each dimension individually. Within each dimension clustering can be performed in a hierarchical manner: first finding clusters with a small spread, then moving up in scale to join small clusters into larger ones. Then multiple dimensions can be examined for objects which appear in clusters in multiple dimension. Such clusters can then be merged into a single cluster—i.e. agglomerative clustering. This agglomeration across dimensions can again be performed at multiple scales.

Figure 7:
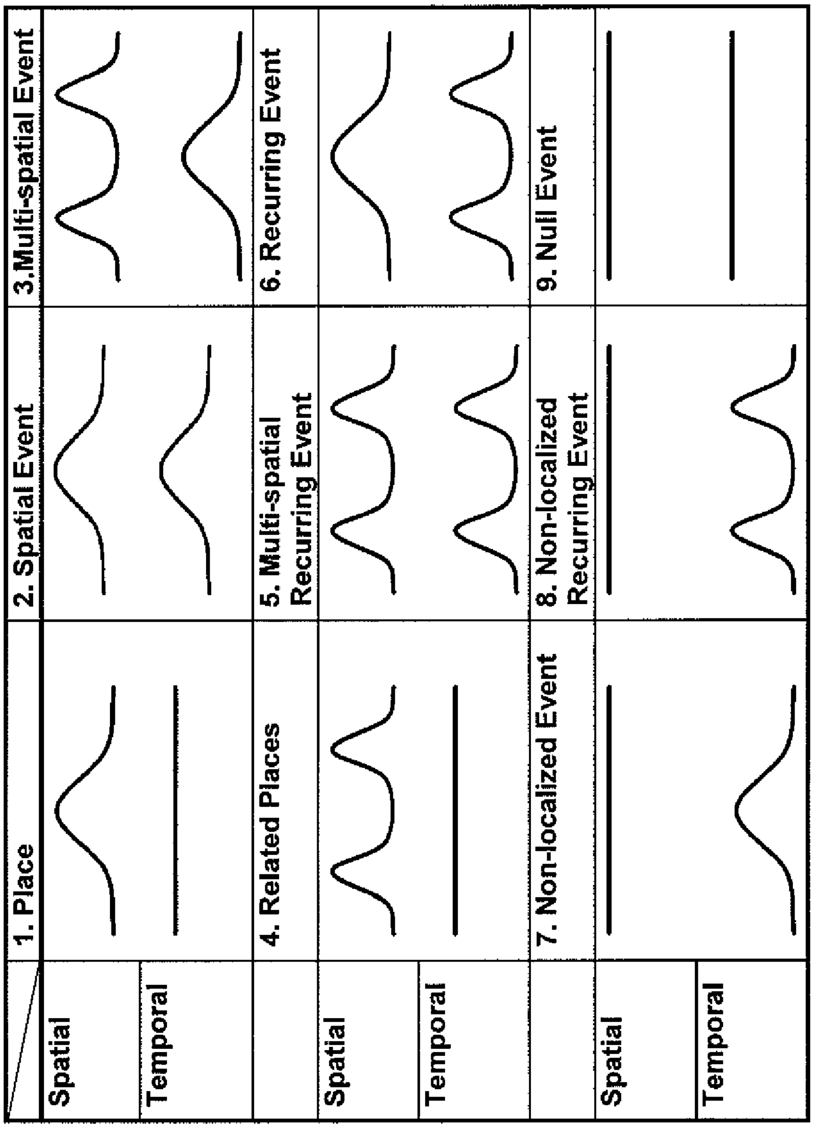
FIG. 7 illustrates nine basic types of spatiotemporal patterns.

In one embodiment, when performing event clustering there are nine basic types of spatiotemporal patterns as illustrated in FIG. 7 (where the graphs represent media/attention/presence distribution in space or time.)

1. Place: There is a peak in the spatial distribution, but a uniform temporal distribution, e.g. Golden Gate Bridge.

2. Spatial Event: A corresponding peak in both dimensions, a one-time event, e.g. SuperBowl XL.

3. Multi-spatial Event: Multiple spatial peaks corresponding to a single temporal peak, an event that occurs in multiple locations at the same time, e.g. the Live Aid concert.

4. Related Places: Multiple spatial peaks with a uniform temporal distribution, distinct places but related in some way, e.g. the set of F1 race tracks.

5. Multi-spatial Recurring Event: Multiple spatial peaks corresponding to multiple temporal peaks, e.g. Iron Maiden's US tour.

6. Recurring Event: A single spatial peak corresponding to multiple temporal peaks, an event that occurs periodically in the place, e.g. a weekly status meeting at the office.

7. Non-localized Event: A uniform spatial distribution with a single temporal peak, a one time global event, e.g. Millennium celebrations around the globe.

8. Non-localized Recurring Event: Uniform spatial distribution with multiple temporal peaks, a repeating global event, e.g. Christmas 9. Null Event: No distinct spatial or temporal pattern.

In many cases it is sufficient to cluster along only the "where" and "when" dimensions (those two dimensions often being sufficient to define an event.) The "who" and "what" dimensions can be used primarily as filters, e.g. filtering to events attended only by a given person (who) or concerning a particular topic (what.) There may be cases when clustering works well proceeding from "where" to "when" to "who" to "what" dimensions, there may be situations where an alternate ordering will work better (either running more efficiently or yielding subjectively better results)—the algorithm can be tuned empirically using a large set of data.

Data clusters be used to automatically generate context query URLs. Generation of URLs can, in one embodiment, be seeded or unseeded. Seeded URL generation uses a seed value or a set of seed values for one or more spatial, temporal, social, or topical criteria. For example, a user may be interested a particular musical artist. In one embodiment, selection of the artist fixes the "who" dimension as the musical artist. Alternatively, the "who" dimension could be expanded by identifying a limited set if individuals that have a strong, clustered associations with the artist. Such individual could include band members, close friends and family.

Once the who dimension of the data is fixed, the system can then search for data clusters in an n-dimensional space associated with those "who" values in the "who" dimension. There can be, of course, a potentially unbounded set of clusters of data associated with a set of discrete "who" values. The system can, in one embodiment, select clusters based on user specified or system default selection criteria. Generally speaking, selection criteria are criteria that relate to one or more properties of clusters. The properties of clusters depend on the exact implementation of the system's clustering methodology. For example, in one embodiment data clusters have attributes indicating the number of "who", "what", "when" and "where" dimensions that define the cluster, "who", "what", "when" and "where" values that the cluster centers on, and the total number of data objects within the cluster.

In such a case, selection criteria can include clusters relating to objects that relate to a threshold number of dimensions, such as, for example, a cluster that matches not only on the "who" dimension, but on at least three "what" dimensions (in a data-space implementing multiple "what" dimensions.) Selection criteria can select clusters relating to a threshold number of objects, for example, only clusters relating to at least 100 objects are selected.

Once a set of clusters of data have been identified, the clusters define one or more contexts that can be used create URL context queries. As discussed above, a cluster corresponds to objects matching along one or more "who", "what", "when" and "where" dimensions. Where a dimension contains multiple attributes, the cluster may represent matches on multiple attributes. Each object, within a given dimension, matches the other objects in the cluster on a value, set of values or a range of values. Such relationships can be expressed as a set of <criteria-attribute>:<value> pairs, where the a given criteria and attribute represents the W4 dimension, and the value is that value common to the cluster.

For example, suppose a user specifies a seed value of a name of a musical artist, "Artist A". If the system identifies a nearby cluster of interest centering on a "what" of "concert", a "where" of "San Francisco, Calif.", and a "when" of Apr. 29, 2008, the corresponding <criteria-attribute>: <value> pairs that define the cluster could be: <who>: <Artist A>, <what>:<concert>, <where>:<San Francisco, CA>, <when>:<April 29, 2008>. Such <criteria-attribute>: <value> pairs can be directly translated to a URL based context query.

http://w4.yahoo.com/who/Artist+A/what/concert/where/SanFrancisco, CA/when/20080429.

or stated more generally:

http://<query server>/[<criteria-attribute>/<value>/]

where [<criteria-attribute>/<value>/] is repeated for every <criteria-attribute>:<value> pair.

In one embodiment, the system can also recognize that a given criteria can be expressed by relational criteria that express the same context or a larger containing context. For example:

http://w4.yahoo.com/who/Artist+A/what/concert/where/SanFrancisco, CA/when/20080429.

could also be expressed as http://w4.yahoo.com/who/Artist+A/what/concert/where/here/when/this-week if the user generates the URL based context query while geo-located in San Francisco the same week of the concert.

The system may also recognize that two or more data clusters are closely related in one or more dimensions, and identify an encompassing set. For example, if clusters are identified logically containing <who>:<Artist A>, <what>: <concert>, <where>:<San Francisco, CA>, <when>:<April 29, 2008>.
<who>:<Artist A>, <what>: <concert>, <where>:<Los Angeles, CA>, <when>:<May 10, 2008>.
<who>:<Artist A>, <what>: <concert>, <where>:<San Diego, CA>, <when>:<June 15, 2008>.

a superset can be identified that encompasses all three clusters:

| |
|---|
| <who>:<Artist A>, <what>: <concert>, <where>:<California>, <when>:<Spring, 2008> |

which could be formatted:

| |
|---|
| http://w4.yahoo.com/who/Artist+A/what/concert/where/california/when/spring+2008 |

Unseeded URL generation does not use a seed value or a set of seed values for one or more spatial, temporal, social, or topical criteria. Rather, in one embodiment, the entire W4 data space is searched for clusters along all W4 dimensions. In one embodiment, the process can proceed initially along a first dimension, for example the "where" dimension searching for clusters in the "where" dimension. Where such clusters exist, the remaining dimensions can be searched for clusters in the manner described under seeded searches. Alternatively, in another embodiment, each dimension can be searched for clusters meeting selection criteria such as, for example, a minimum number of objects associated with the cluster, then the set of all clusters meeting selection criteria can be compared to identify clusters selected on two or dimensions.

Once a cluster has been selected for URL generation, URL generation can proceed, in one embodiment, as described above under seeded URL generation.

Autohyperlinking and Navigation in URL Based Context Queries

As described above, a context query can be used to select data objects in a W4 COMN or similar network relating to a context. Data objects relating to a context query can be delivered to a user executing the query in any format suitable for delivery of electronic data. Perhaps the most natural form for data delivery of data stored and accessed over the Internet, however, is as hyperlinks to W4 objects.

When a URL context query is executed, a set of RWEs and IOs relating to the context are identified. Each object is addressable from a browser session. A hyperlink can be constructed that allows retrieval of data relating to the objects. In one embodiment, each hyperlink is embedded in a dynamically generated webpage that is displayed to the end user. For example when the URL:

| |
|---|
| http://w4.yahoo.com/who/Artist+A/what/concert/where/SanFrancisco,CA/when/20080429 |

is executed in a browser session, the query selects a set of IOs and RWEs relating to the context. Where the query resolves directly to an IO representing a data object, such as a video of the concert, images from the concert, or a news story about the concert, the hyperlinks points to the data object itself, such as a JPEG, WAV, HTML or text file that a user can access directly from a browser. Where multiple data objects exist relating to the same content, links can be presented to all objects, or a single instance can be selected using user or default preferences, such as preferred sources or the highest quality available.

There may also be objects related to a context, however, that are not data objects. RWEs may be related to a context, but typically are represented in a W4 COMN by multiple data objects. For example, Artist A may have been performing supported by Artist B, a separate RWE in the W4 dataspace that is associated with multiple data objects (e.g. a profile, a BLOG, media objects and so forth.) In one embodiment, the system could automatically select a data object representing Artist's B W4 profile and provide a hyperlink to that object. Alternatively, the Artist B could be represented as a hyperlink containing a URL context query:

http://w4.yahoo.com/who/Artist+B that returns all available W4 data relating to Artist B. Similarly, logical IOs that are related to a context query may represent a topical IO that does not link to a single data object. For example, the music performed by Artist A may fall into genre D. If a topical IO for genre D falls within the context, in one embodiment, genre D could be represented as a hyperlink containing a URL context query:

http://w4.yahoo.com/what/genre+D

A web page listing hyperlinks to objects related to a context can be further enhanced by providing links to related contexts. Such related contexts allow users to navigate the multidimensional data space by exploring contexts that contain values that are nearby a root context query along each axis of the W4 data space.

There are several methodologies by which closely related contexts can be generated. Most simply, if a data dimension represents a spectrum of values that vary in a regular and predictable way, context queries can be empirically generated by modifying one element of the root query by a predetermined increment. For example, suppose a user enters the root query:

| |
|---|
| http://w4.yahoo.com/who/Joe.D/what/restaurants/where/San+Francisco,CA/when/2008 |

where a person wishes to retrieve data relating to restaurant's the user's friend, Joe.D, has visited or commented on.

A related context query can be generated by decrementing the "when" when dimension by one. For example:

| |
|---|
| http://w4.yahoo.com/who/Joe.D/what/restaurants/where/San+Francisco,CA/when/2007 |

A family of related URLs can be generated by varying different time specifications in standardized ways. For example, in one embodiment, years are incremented and decremented twice by one year, days are one day are incremented and decremented twice by one day, and so on.

In another example, in regard to the spatial dimension, a related context query can be generated by selecting nearby geographical locations, or selecting a larger geographical area within which the criteria location resides:

| |
|---|
| http://w4.yahoo.com/who/Joe.D/what/restaurants/where/Oakland,CA/when/2008 |

| |
|---|
| http://w4.yahoo.com/who/Joe.D/what/restaurants/where/California/when/2008 |

Where spatial dimensions are expressed by numeric bounds, the bounds can be varied by, for example, doubling the width or radius of the bounded area. Such context queries can be created without regard to actual data that may or may not exist, and may retrieve no data at all.

In another example, in regard to the "who" dimension, a related context query can be generated by selecting larger groups that encompass the "who" criteria or by selecting similar groups:

http://w4.yahoo.com/who/friendswhat/restaurants/where/Oakland,CA/when/2008
http://w4.yahoo.com/who/family/what/restaurants/where/California/when/2008

All of the examples above are intended to be illustrative, and not limiting, and illustrate the basic principle that related context queries can be generated by varying single context criteria in a predetermined manner appropriate to the criteria domain. In other embodiment, two or more criteria can be varied to produce a large set of multiple permutations of various nearby criteria. Such context criteria can be performed without regard to actual data that may or may not exist. URLs generated by incrementing and decrementing criteria values may, in fact, retrieve no data.

A more sophisticated, and precise way of generating related URLs to take advantage of the system's ability to identify data clusters in the multidimensional W4 data space. Such URLs can be automatically generated by the system based on the density of known objects in W4 space and the predefined set of logical operators that can connect them. For example, the set of logical operators for linking objects in the "where" and "when" dimensions include: containing, contained in, overlapping (with temporal specializations for overlapping the beginning and overlapping the end), adjacent (with temporal specializations for adjacent to the beginning and adjacent to the end), and proximal. "When" can also the logical operator of a "period" which accounts for periodic links such as "afternoon", "Wednesdays", "weekends" "Spring", etc.

W4 objects have varying density in W4 space-some events will generate more objects, some locations will be more densely populated than others, some topics will be more popular, etc. By clustering or segmenting the W4 objects in the W4 dataspace, manifold boundaries can be defined/estimated and corresponding human-readable URLs can be generated. Once these clusters have been generated, links between W4 URLs can be automatically generated.

For example, consider the relative W4 URL:

http://w4.yahoo.com/where/home/when/yesterday/afternoon/who/me.

If data clusters are located along the "where" axis, the system may provide URL context queries to nearby locations "next_door" and "across_the_street" (relative to the current location of "home"). Additionally the system may, based on data clustering density, provide a link up to a containing entity (e.g. "my_street") or down to a contained entity (e.g. "my_kitchen"). Similarly the When dimension could be expanded to "this_week", contracted to "yesterday_afternoon" and related at the same level to "today" and "2_days_ago" based on data clustering and density.

In the above example the "who" dimension could be expanded to "my_family" or "my_coworkers", could relate laterally to "my_friend" and "my_other contact", but cannot be contracted to a smaller entity than "me". As an example of navigation in the "what" dimension, "dog" may relate laterally to "cat" and "wolf", may expand to "carnivore", and could contract to "golden retriever" and "labradoodle", again, based on data based on data clustering and density.

Restricting navigation between URLs to the few directions parallel to each W4 axis can fail to identify some nearby events that are not easily reachable. For example, an event somewhat similar along several dimensions but not especially close on any one dimension will not be easy to navigate to. To remedy this, in one embodiment, the system can provided a catch-all "Related" URLs category containing URLs that are proximate in W4 space, though not necessarily closest along any single axis. The Related category may also show events that are similar in other ways: e.g. similar size, or containing a similar number of media objects, or similar view counts, or other popularity metrics such as "interestingness".

Additionally, due to the human-readable format of W4 URLs a user can navigate to nearby or related URLs simply by directly modifying the URL, though in this case they are not guaranteed to find any media objects. The system can provide links from empty user-supplied URLs to "nearby" URLs known to contain data. All URLs generated from data clusters will contain media objects or presence information (for people or objects) since they were generated based on the clustering of those objects. However not all automatically-generated URLs will be visible to all users, if for instance the data associated with a W4 URL is not visible to a given user.

Data Privacy in URL Based Context Queries

The W4 data space is populated with at least some data that is potentially sensitive. For any number of reasons, a user may not wish to allow some, or all potential observers from viewing the user's data including: data such as phone numbers, home addresses, bank accounts, credit card accounts, retail transactions, and so forth. Through the services of a W4 privacy system, a user may choose to restrict access to a data object or class of data objects by restricting access to a class of individuals (e.g. friends), specific persons, or to all other users, or by specifically denying access to a class of individuals (e.g. friends), specific persons, or to all other users In such a case, if an unauthorized user has a valid hyperlink to the object, the unauthorized user will be unable to display the object.

In one embodiment, objects and relationships in a W4 COMN can, from a privacy standpoint, can be classified as RWE controlled objects relationships and shared network objects. Shared network objects and relationships are objects and relationships that are created by the network, and do not relate to a specific RWE, such as, for example, topical IOs relationships between topical IOs, data IOs created by the network which contain public domain data and IOs created by RWEs that RWEs place in the public domain under the control of the network.

RWE controlled objects are objects created by, or on behalf of, a specific RWE and which the RWE has a right to control. RWE controlled objects can include, for example, a user profile, a business profile, a user playlist, user interaction data or user presence data. RWE controlled relationships are relationships created by, or on behalf of, a specific RWE and which the RWE has a right to control. RWE controlled relationships can include, for example, a relationship to another user RWE, to an IO for social circle, to an IO for a topic, and so forth.

The types of RWE controlled objects and relationships a user may wish to control access to can include:

(1.) Data objects themselves.

(2.) Location history—where the user has been, where they have created media or other types of data objects.

(3.) Times of activity—when the user has created media or actively engaged with a tracking system. This information is, of course, much more sensitive when coupled with location data; for example a teen may not want to expose to their parents how late they were awake last night, but it's far worse to expose how late they were out of the house.

(4.) Topics of interest—some topics may be sensitive, e.g. alcoholism, cancer, mental illness.

(5.) Social information—while it should be obvious that a user may wish to restrict access to explicitly defined social relations (e.g., whom I label as "friends" or "potential employers"), the W4 system has the potential to also expose implicit social relations: who is often co-present with whom, or who has shared interests with whom.

In one embodiment, in addition to restricting access to data relating to a URL context query, the W4 privacy system can also, in some circumstances, hide the existence of data objects. Knowledge of the existence of a data object (or knowledge of a person's or object's presence) alone, without access to the media, can be a privacy risk. In one embodiment, the W4 system must respond identically to a URL containing no data (no associated media or presence information) and to a URL containing only data that the requesting user is unauthorized to see (e.g. respond with a "Not Found" or "No Data Available" in both instances.) For example, if a requester who is not authorized to see photos from Simon visits the W4 URL:

http://w4.yahoo.com/where/berkeley/when/12-May-2008/afternoon/who/simon and gets a response that is different in any way from the response at:

http://w4.yahoo.com/where/nowhere/when/never, the requestor knows that Simon was in Berkeley on the afternoon of May 12, even without any media being shown or linked to. A viewer must not be able to determine via the type of "Not Found" response whether a user intentionally hid their location or whether a technical or network problem resulted in the missing data. The W4 privacy system respects not only data privacy, but also presence privacy by hiding the existence of data objects from users not authorized to see it.

Metadata in data objects can also pose a privacy risk. Metadata, and in particular metadata regarding the creation of data objects, can reveal data relating to a persons location history, times of activity, topics of interest and social information. Thus, in one embodiment, the W4 privacy system can restrict access to data objects that not only have content that relates to sensitive matters, but also data objects containing metadata relating to sensitive matters. Alternatively, a data server that provides access to data objects could automatically strip metadata.

More subtly, the existence of such metadata, and in some cases, the data described by the metadata, can be revealed indirectly through data clustering. For example, if the URL:

http://w4.yahoo.com/where/berkeley/when/12-May-2008/afternoon/who/simon yields a related URL:

| |
|---|
| http://w4.yahoo.com/where/new+york/when/12-May-2008/afternoon/who/simon |

it strongly implies that a data cluster having such attributes was identified, indicating Simon was in New York, even if executing the above URL returns no data.

Furthermore, if a user allows another user to access a data object, then the existence of the metadata may be revealed as well. For example, suppose Simon allows Simone to access his photographs. Then the query:

| |
|---|
| http://w4.yahoo.com/where/berkeley/when/12-May-2008/who/simone/what/photographs |

could yield a related URL:

| |
|---|
| http://w4.yahoo.com/where/berkeley/when/12-May-2008/who/simon/what/photographs |

In one embodiment, the system remedies the above problems by determining data clustering on a user by user basis when a context query is executed. Access restrictions are checked for every data object identified in the process of agglomerating data. Objects for which the user lacks proper access are not included in the agglomeration process. In another embodiment, metadata is not used in the data agglomeration process. In another embodiment, metadata for shared objects is not used in the data agglomeration process.

Of course, data relating to a person's location history, times of activity, topics of interest and social information may be revealed in data controlled by other users. For example, Simon may not wish anyone to know who his friends are, where he goes, or what he does, but Simone may have no problem letting everyone know Simon is her friend, and that they go to a particular coffee house for latte every Tuesday afternoon. Any social networking site or data sharing service carries the same risk.

In one embodiment, a user can store permissions for RWE controlled data in a permissions IO associated with the user RWE. In one embodiment, a user can store permissions for RWE controlled data with the users profile IO. In one embodiment, a user can store permissions for RWE controlled within the data objects and relationships themselves. In one embodiment, a user can store permissions for RWE controlled data in a database available to the network that maintains permissions data for a plurality of users.

Deriving Income from URL Based Context Queries

URL based context queries are valuable tools for a variety of users to select a broad range of content that is available in a W4 COMN or similar network. A URL based context query is analogous to a keyword search using a conventional search engine such as Yahoo! or Google. In both cases, a user enters keywords which are matched to an index of available content. For example, a user who is interested in what's going on in Manhattan in the summer of 2008 can enter a simple query into a conventional search engine such as Google or Yahoo!:

manhattan summer 2008 to retrieve links to webpages that a search engine web indexing process has associated with the keywords "Manhattan", "summer" and "2008."

A user could also enter in a URL based context query, roughly to the same effect:

http://w4.yahoo.com/where/manhattan/when/Summer, 2008 to retrieve data relating to data objects related to Manhattan during the summer of 2008. Both queries are valuable to users in their in their own right, but the URL based context query is more sophisticated and provides a better match and more personalized set of matches because, among other things:

The context query can identify websites, media and other network accessible data objects related to "Manhattan" through indirect relationships and ambiguous references or conceptual associations, whereas the search engine may not identify data related to "Manhattan" unless the data or metadata related to the data explicitly contains the string "Manhattan."

The context query can bypass data with no relationship to "Manhattan" even if the metadata associated with such data contains the string "Manhattan."

The context query can use W4 data relating to the user entering the query to filter query results and tailor them to the user's interests (e.g. if the user likes Jazz, then any events relation to Jazz in Manhattan in the summer of 2008 are selected, if the user hates Jazz, then no data relating to Jazz is included in the query result set.)

The context query can detect relationships between the context criteria and data associated with persons within the social circle of the user entering the query to detect any relationships between the context and the user's social relations (e.g., two of the user's friends are traveling to Manhattan in August, 2008.)

A number of online services which provide Internet search engines generate revenue by creating a marketplace that allows web site owners to bid on placement of advertisements on search results (e.g. Yahoo! Sponsored Search, Google Adwords.) Typically, a website owner enters in a set of keywords or phrases that describe the subject matter to which their website relates and a bid for a maximum cost-per-click (CPC) for each keyword or phrase. When a user enters a search containing such a keyword or phrase, the website for which an advertiser has bid a CPC for the keyword or phrase is given preferential placement in search results. The advertiser pays a CPC only if a user actually clicks on the link. In a closely analogous model, an advertiser can pay for a cost per impression (CPM), where the advertiser pays a cost for every time their ad copy is displayed on a search result or other webpage, while some embodiments include a cost per action (CPA) model where an advertiser only pays a set or variable amount based upon a further action the user takes, e.g. purchasing, subscribing for a newsletter, joining a loyalty program, etc.

Web advertising services also generate revenue by matching ad copy to content by providing a content network composed of an unlimited number of interconnected websites that allocate space for advertisements. Advertisers can select specific websites within the network and bid for placement of ads on a CPC or CPM basis on selected websites, possibly targeted to specific hours, days, or dates of placement, as well as ad size and frequency of placement, or advertisers can select specific keywords or categories of content, websites, domains or other online advertising inventory available for display to users on personal computer or mobile devices.

A URL based context query is provides similar advertising opportunities. In one embodiment, the result of a URL based context query is a dynamic webpage that contains a list of hyperlinks to content that relates to the context query. This list can be ordered in a number of different ways. For example, the hyperlinks can be ordered by relevance or closeness to the context query, where content that is closest to the context query is higher in the list than content that is distantly related. In one embodiment, advertisers are allowed to bid to influence their position in the list of content in a dynamic webpage generated in response to a context query.

In one embodiment, web pages generated in response to URL context queries can also reserve space for advertisements that is separate from the list of hyperlinks to content that relates to the context query (e.g. a banner or a sidebar.) In one embodiment, advertisers are allowed to bid to place advertisements in this reserved space (e.g. analogous to a content network.)

In one embodiment, users can bid on key words and key phases within context queries in a manner similar to that used by existing CPC web searches. Thus, an advertiser could bid for a set of keywords "Manhattan", "Summer" and "2008." In a model implementing keyword based bidding, any URL context query having such tokens would meet the criteria, for example:

| |
|---|
| http://w4.yahoo.com/where/manhattan/when/Summer,2008 |
| http://w4.yahoo.com/who/friends/who-where/manhattan/who-when/Summer,2008/who-what/restaurants |
| http://w4.yahoo.com/what/songs/what-subject/manhattan/when-recorded/Summer,2008 |

Such an implementation has the advantage that it can embrace many disparate contexts.

In one embodiment, if an advertiser's keywords are matched in the context query and the results of the query include the advertiser's content (other query operands may exclude advertiser content), then advertiser content receives preferential placement in the list of hyperlinks to content on the dynamic webpage. In one embodiment, if an advertisers keywords are matched in the context query, the advertiser's content always appears in the list of hyperlinks to content on the dynamic webpage and receives preferential placement in the list of hyperlinks. In one embodiment, if an advertiser's keywords are matched in the context query, the advertiser's advertisements appear in an area on the dynamic web page in an area allocated for advertisements.

Simply matching bid keywords to elements within context queries, however, does not fully exploit the capabilities of a W4 COMN. As shown above, context queries containing "Manhattan" and "Summer" and "2008" can refer to entirely unrelated contexts, some of which have nothing to do with what's happening in Manhattan in the Summer of 2008. This is because a context query goes well beyond a search engine query in that context queries includes relationships and logical linkages between criteria that implicate complex data relationships.

In one embodiment, a context query can be matched to keyword based bids by using the full spectrum of data available to a W4 COMN or similar network. The network can use, without limitation, spatial, temporal, topical and social data and relationships relating to the context query, the querying user, keywords within keyword-based bids, the advertiser placing keyword bids, and the content of advertisements related to the keyword-based bids, so as to identify bids that most closely relate to the context query and are most relevant to the querying user. For example, a travel service may bid on "Manhattan", "Summer" and "2008", advertising low air fares and higher end accommodations. Only travelers who have expressed an interest in New York, fly frequently, and live out of town and have entered a query that relates to "Manhattan", "Summer" and "2008" may be selected.

Such a matching process is inherently fuzzy. There is no need, and it may even be undesirable, for matching context queries to keyword based bids where all bid keywords are literally matched. For example, "Manhattan" and "Summer" and "2008" implies "Central Park" and "August" and "2008". Thus, in one embodiment, a set of keywords can automatically encompass related contexts.

In one embodiment, the advertiser pays for placement of advertiser content in preferred positions (i.e. ranking) within the list of hyperlinks to content on the dynamic webpage. on a CPC basis or a CPM basis. In one embodiment, the advertiser pays for placement of advertiser advertisements in areas allocated for advertisements on dynamic webpages generated by URL based context queries on a CPC basis or a CPM basis.

A second revenue model can be based on advertisers licensing or bidding on complete context queries. Bids for context queries could be further subdivided into two broad categories: (1.) bids for ranking (i.e. preferred ordering) of advertiser content in the list of hyperlinks on a dynamic webpage (as in conventional keyword CPC/CPM bidding), or bids for placement of advertisements on selected areas of dynamic context query webpages (analogous to CPC/CPM bidding for placement on a content network.)

In the case of bidding for rank within content on a dynamic context query webpage, multiple advertisers could maintain concurrent bids on a given URL based context query, wherein, in one embodiment, content is then ranked on the dynamic context query webpage by bid amount, or some other formula using additional factors such as click through rate (CTR) or webpage quality.

In the case of bidding for placement, selected areas of dynamic context query webpages can, in one embodiment, support advertisements in a number of designated places on the web page. Examples include the page header, the page footer, a sidebar visible on the initial display of the page, overlay flash ads that display on the initial display of the page and pop-up ads. In one embodiment, bids can be accepted for each position on the webpage independently of one another. In one embodiment, bids can be solicited for all display positions on the webpage as a unit.

Bids for placement of advertisements on a webpage or selected areas of a webpage can, in one embodiment, be exclusive or shared, continuous or time sliced, and global or context based. An exclusive placement allows an advertiser to place an advertisement in a predetermined position on a webpage (which may vary dynamically) to the exclusion of all other advertisements. Exclusivity could be page wide, or limited to a specific advertising area on the page. A shared placement allows two of more ads to obtain rights to a webpage or to a specific advertising area on the page, wherein, for example, advertisements for one advertiser are displayed at a time, but every time the webpage is displayed, the advertisement that is displayed is randomly selected.

Exclusive placement and shared placement may be continuous or time sliced. In one embodiment, a continuous placement is in effect so long as the advertiser's bid qualifies the advertiser for placement on a context based query webpage. In one embodiment, a placement is time sliced where advertisers bid on recurring time slices, e.g., Monday through Friday between 9:00 AM and 5:00 PM or specific time slices, e.g. Dec. 24, 2008 between 6:00 AM and 11:00 PM. Bids for continuous placement and various forms of time slices can coexist without contradiction, and enables advertisers to achieve very fine grained bidding for placement of advertisements.

Any bid for combinations of exclusive, shared, continuous or time sliced can be global or context based. Global bids are bids for placement on a context query webpage no matter who (or what) enters the URL context based query associated with the webpage. A context based bid, on the other hand, is a context that can be used to select a specific subset of users in which the advertiser is interested. For example, a music download service and a travel agency who targets mature professionals living in Manhattan may both be interested in displaying ads on a "where/manhattan/when/Summer, 2008" context based web page, but have very different target audiences. Such targeted audiences may be targeted using contexts who-age/15-30/who-where/anywhere and
who-age/40-60/who-where/manhattan/who-interest:travel respectively. The contexts obviously do not overlap, and bidding for each could proceed independently.

On the other hand, bid contexts could overlap. For example:

who-age/25-55/who-where/anywhere/who-interest:music and
who-age/40-60/who-where/manhattan/who-interest:travel The first context targets anyone 22-55 who has an interest in music, whereas the second context targets anyone 40 to 60 who lives in Manhattan and who is interested in travel. The contexts overlap in a manner that can be expressed as an intersection context:

who-age/40-55/who-where/manhattan/who-interest:travel/who-interest:music

Thus, within the intersection context represents a context where the music download service and the travel agency are competing with one another for advertising placement. In one embodiment, where the highest bidder wins placement, where a given execution of a URL based context query implicates multiple bid contexts, the highest bid within the set of overlapping bid contexts prevails.

In one embodiment, a context query bidding system or process could facilitate competition in a system having overlapping bid contexts by displaying the bid contexts for all bidders for a given URL based context query. In one embodiment, the system could further aid bidders by highlighting contexts that overlap the bidder's context and displaying an intersection context that shows the bounds of the overlap. In one embodiment, the system could capture statistics to show the total number of hits in the intersection context over time. In one embodiment, the system could allow a bidder to place separate bids on the intersection contexts.

Much like bid contexts, URL based context queries can also overlap. The set of all possible context queries is immense, perhaps numbering in the billions. Nevertheless, each query within this set defines a conceptual space that can be very large, and multiple queries can have conceptual spaces that overlap, or are contained within, each other. In a simple example:

(1.) http://w4.yahoo.com/where/new+york+ny/when/Summer,2008
(2.) http://w4.yahoo.com/where/new+york+ny/when/August,2008/what/concerts
(3.) http://w4.yahoo.com/where/manhattan/when/Summer,2008
(4.) http://w4.yahoo.com/where/manhattan/when/August,2008
(5). http://w4.yahoo.com/where/central+park/when/this-month/what/concerts It is readily seen that some contexts completely contain other contexts, e.g. where/new+york+ny/when/Summer, 2008 completely contains the conceptual space of where/ manhattan/when/Summer,2008 and where/manhattan/when/Summer, 2008 completely contains the conceptual space of where/manhattan/when/August, 2008. It is also apparent that the conceptual space of some queries overlap. For example, new+york+ny/when/August,2008/what/concerts and where/manhattan/when/Summer,2008 overlap, and have an intersection context where/manhattan/when/August, 2008/what/concerts. Overlap or containment can be dynamic, for example, where/manhattan/when/August,2008 only contains where/central+park/when/this-month/what/concerts when the query is executed in August Unlike bid contexts, however, where for a given URL based context query, advertisers compete for specific demographic subgroups within the set of all query users, competition between URL based context queries is more subjective. The simple fact that queries have overlapping conceptual spaces does not mean they truly compete. This may be true because there is no data in the conceptual space defined by the intersection of the two queries, i.e. the two queries return completely different data, e.g. where/manhattan/what/tibetian+music/when/jan-july,2008 and where/new+york+ny/what/tibet/when/summer,2008 conceptually overlap, but the overlap may have no data if there is no data relating to Tibetan music for June and July of 2008.

Furthermore, a context query may encompass a very large conceptual space and yet the query has no real commercial value because it is never likely to be used. Examples include nonsensical queries like:

http://w4.yahoo.com/where/athens/when/500+BC/what/rap+music

Such examples also include queries that anyone would expect to return a set of results so large that it is essentially unusable:

http://w4.yahoo.com/who/anyone/where/California/

Such examples also include queries that may have a great deal of interest to a very small group of individuals, but essentially none to most people.

--- http://w4.yahoo.com/who/anyone/who-interest:non+abelian+gauge+theory/who-what/restaurants/

---

In the absence of actual usage data, the advertiser engages in a calculated guess as to what kind of context query a typical user is likely to enter at any given time. For example if a user is interested in concerts in Manhattan in the Summer of 2008, they can enter

---

(1.) http://w4.yahoo.com/where/new+york+ny/when/Summer, 2008/what/concerts
(2.) http://w4.yahoo.com/where/manhattan/when/Summer, 2008/what/concerts
(3). http://w4.yahoo.com/where/manhattan/when/June, 2008/what/music
http://w4.yahoo.com/where/manhattan/when/July,2008/what/music
http://w4.yahoo.com/where/manhattan/when/August, 2008/what/music

---

Query (2.) is arguably the most properly scoped single query, yet in a user's mind, it may be more intuitive to enter new+york+ny instead of manhattan, or it may be more intuitive or useful to look at all data relating to music and Manhattan month by month.

In the absence of actual data statistics, it is also not clear when a result set from a query will be too small, too large or contain too much data of marginal interest. A URL context query that produces an interesting set of data, reasonably focused on the topic, but also finding interesting side lights will produce more return traffic.

A context query bidding system can assist bidders with such issues in at least three ways. First, a context query bidding system can use unseeded URL generation as described above in GENERATION OF URL BASED CONTEXT QUERIES to generate a list of URLs that have show a threshold level of clustering on a threshold number of data axes. For example, at least 100 data objects clustered on at least 3 data axes. Such a process can be considered to be, in effect, mining the W4 dataspace for interesting data clusters. Such "interesting" clusters can then be presented to advertisers in an ordered or indexed list with cluster statistics.

Second, context query bidding system could allow an advertiser to enter in a seed context query that presents the user's basic idea in one embodiment, such as in the example above, where/manhattan/when/Summer, 2008/what/concerts, and the system generates related queries as described above in GENERATION OF URL BASED CONTEXT QUERIES and presents the related queries to the end user as a list from which the advertiser can select from. The list can also include clustering statistics to guide selection of specific queries.

Third, the system could track statistics for all context queries actually entered. The system could periodically, or on demand, generate a list of those queries and usage statistics ordered or indexed by subject matter and number of clicks. Such usage statistics could also be used by a system displaying URL based context queries based on data clustering or could a allow an advertiser to enter a specific context query and get usage and clustering statistics for that URL.

In one embodiment, a context query bidding system allows advertisers to bid for ad placement on individual context query URLs on a CPC or CPM basis. In one embodiment, the system additionally allows bids to be qualified by target context criteria, and can additionally provide the capability to bid on target intersection contexts.

Once an advertiser has bid on a selected URL based context query, the system can automatically provide a view of related URLs generated, in one embodiment, using the methods described in GENERATION OF URL BASED CONTEXT QUERIES to generate a list of related URLs, where related URLs can be generated empirically, based on data clustering or both. The system can present useful statistics regarding related URLs, such as clustering and usage statistics and bids placed by other advertisers on such URLs.

In one embodiment, a context query bidding system could incentivize a bidder to bid on related contexts. For example, if a bidder bids a high traffic URL based context query such as where/manhattan/when/Summer, 2008 for, say, $0.20 CPM, the system could offer the advertiser a $0.05 CPM incentive on where/manhattan/when/July, 2008. The incentive could, in one embodiment, increase as the number of related URLs are selected and bid. In one embodiment, related URLs are bid in an open marketplace, regardless of incentives. Another type of incentive could be allowing a cluster of related URLs to be bid as a package with a single CPM or CPC.

Incentives in general are designed to both reward heavy advertisers who make extensive use of the system, and to increase the total number of URL based context queries in actual use. Over the long run, a properly designed incentive program can increase the overall revenue generated by the system.

Illustrative Embodiments of Concepts Described Above

The above principles can be further clarified with reference to an illustrative examples of data, processes and systems within a W4 COMN or similar network that can be used to support URL based context queries, URL based context query generation, URL based context query linking and navigation and deriving income from URL based context queries.

Figure 8:
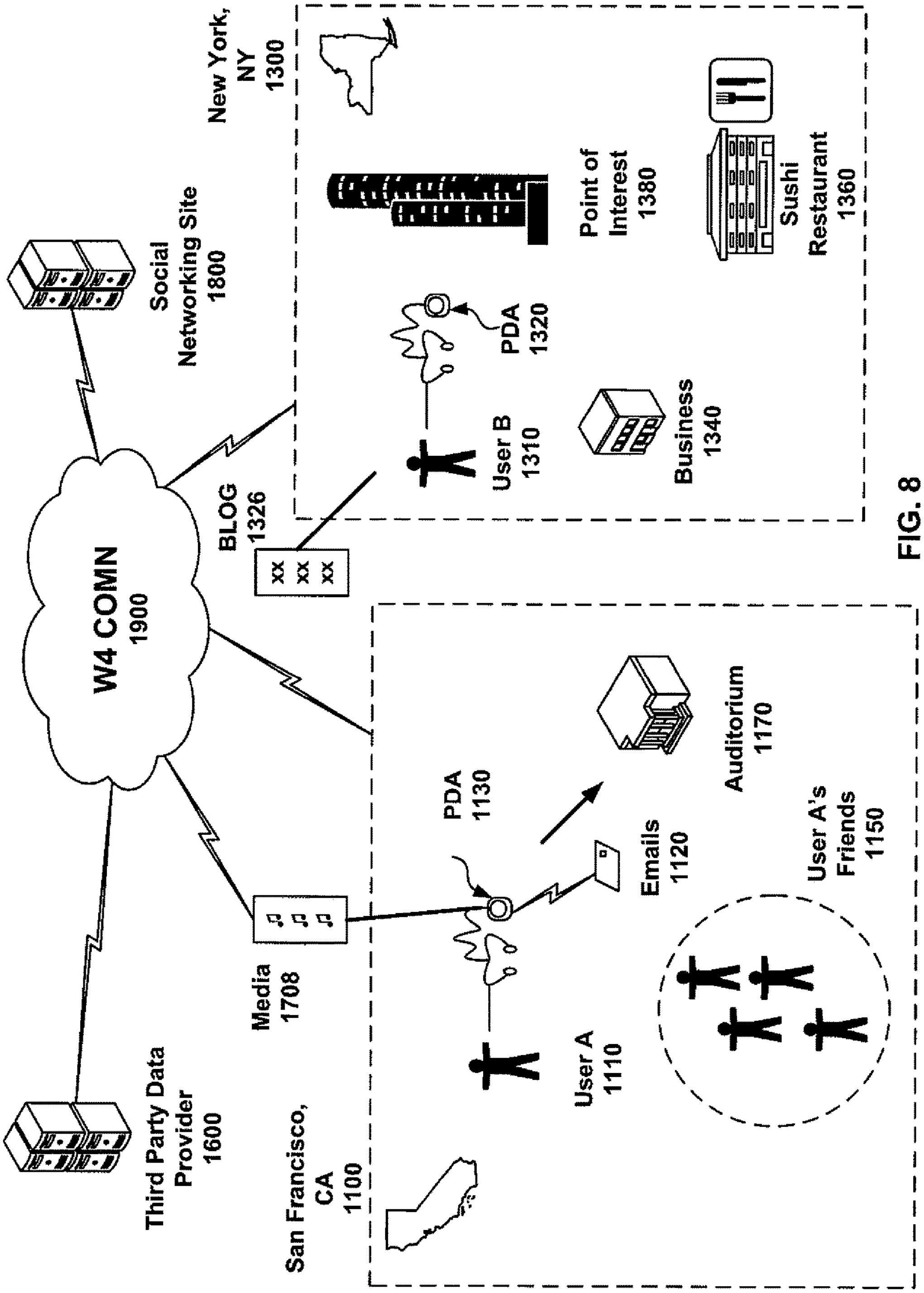
FIG. 8 illustrates one embodiment of the use of a W4 COMN for URL based context query.

FIG. 8 illustrates one embodiment of the use of a W4 COMN for URL based context query.

In the illustrated embodiment, there are two users 1110 and 1310 who have PDAs 1130 and 1320 respectively. Each of these users can enter in a URL context based query using their respective PDA 1130 and 1320. User A 1110 is currently located in San Francisco 1100. The user's presence in San Francisco may have been detected via the user's PDA 1130 by, for example, an embedded GPS device, triangulation of cellular signals, or identification of a servicing cell tower.

User A 1110 is currently listening to media 1708 reflecting a song by musical group C using his or her PDA 1130. User A 1110 periodically sends emails 1120 to other users using the PDA 1130. Recently, User A has sent another user several emails expressing an interest in sushi restaurants in New York. Within San Francisco, User A is currently at an auditorium 1170 to purchase tickets for a future event at the auditorium User A 1110 has a group of friends 1150 in San Francisco 1100.

User B 1310 is currently located in New York 1300. The user's presence in New York may have been detected via the user's PDA 1320 by, for example, an embedded GPS device, triangulation of cellular signals, or identification of a servicing cell tower. User B has recently visited point of interest 1380, a tourist attraction (e.g. the observation deck of the Empire State Building), and is a customer of a business 1340. Both the point of interest 1380 and the business 1340 are also located in New York. User B has written entries in his or her BLOG 1326 praising the point of interest 1380 and the business 1340. Next month, unknown to User A 1110 and User B 1310, the business 1340 will be sponsoring an event at the auditorium 1170 in San Francisco 1100.

There is at least one sushi restaurant 1360 in New York 1300 known to the network. User A 1110 has never heard of the restaurant 1360. User B 1310 doesn't like sushi. The restaurant 1360 has been reviewed and rated as excellent by at least two local publications. There are third party data providers 1600 connected to the W4 COMN 1900 that can provide additional data relating to objects within the W4 COMN. For example, third party providers can supply news and commentary relating to RWEs. In the case of media objects, third party providers can supply an extensive set of descriptive metadata relating to specific songs, videos and other types of media. For example, the Allmusic database (formerly the All Music Guide, owned by All Media Guide) provides metadata which includes:

- Basic metadata such as names, genres, credits, copyright information, product numbers.
- Descriptive content such as styles, tones, moods, themes, nationalities, etc.
- Relational content such as similar artists and albums, influences, etc.
- Editorial content such as biographies, reviews, rankings, etc.

One or more social networking sites 1800, such as, for example, Facebook and LinkedIn connected to the W4 COMN 1900. User B 1310 is a member of one of such social networking sites.

All of the objects and entities shown in FIG. 8 are known to the W4 COMN 1900. Networked devices such as, for example, the user's PDA's 1130 and 1320 are connected to the W4 COMN 1900 in real-time. Non-networked entities such as, for example users, 1110, 1310 and 1150 can be known to the network indirectly through proxy devices, or directly through, for example, memberships in online services, including those provided by the W4 COMN, or through emails, BLOGs and media consumption.

Figure 9:
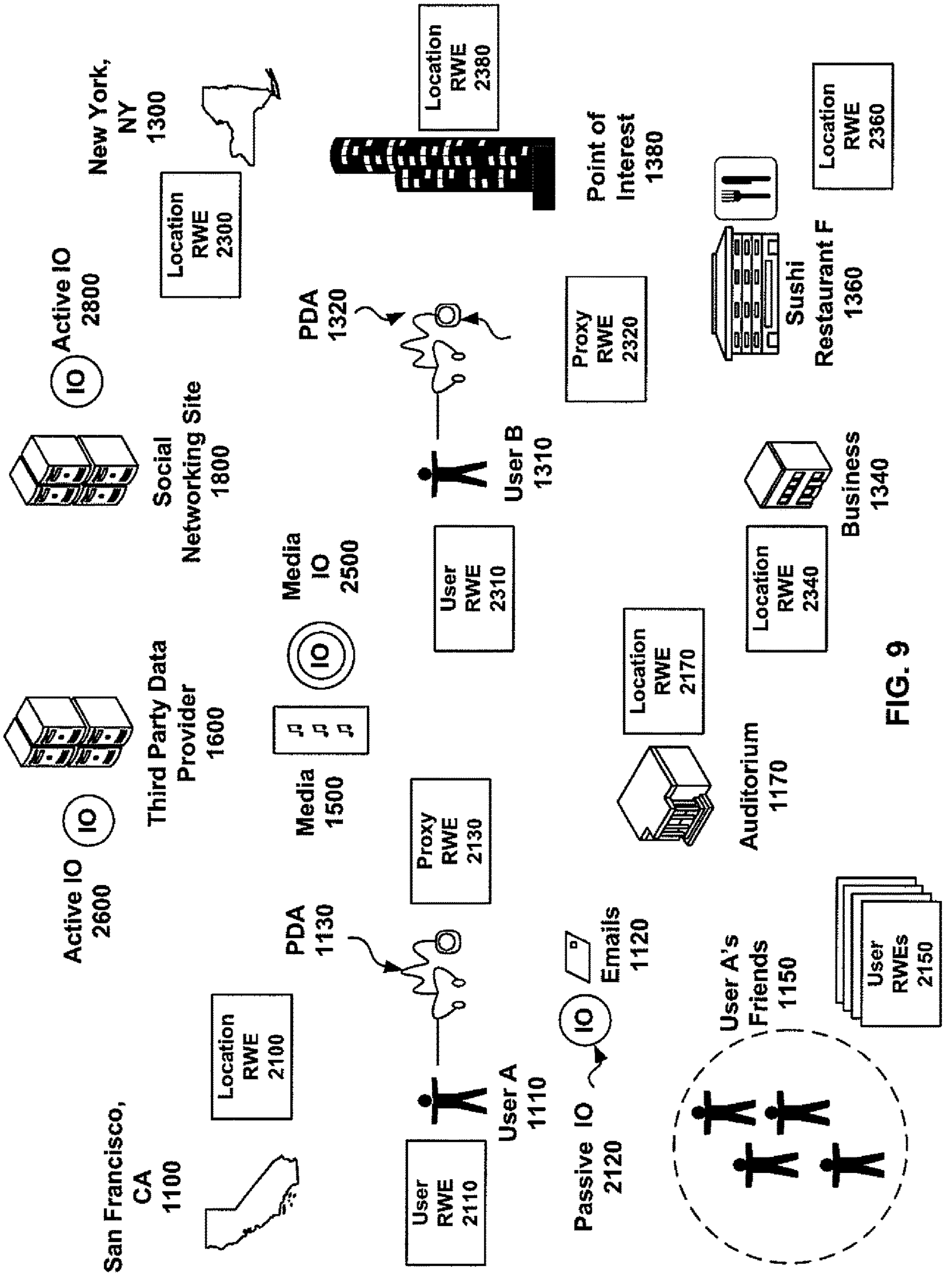
FIG. 9 illustrates one embodiment of how the users and devices shown in FIG. 8 can be defined to a W4 COMN.

FIG. 9 illustrates one embodiment of how the users and devices shown in FIG. 8 can be defined to a W4 COMN.

Individuals 1110, 1310 and 1150 are represented as user RWEs, 2110, 2310 and 2150 respectively. Each individual's devices 1130 and 1320 are represented as proxy RWEs 2130 and 2320 respectively. The user's emails 1120 are represented as one or more passive IOs 2120. Media 1500 is represented as a media IO 2500, a type of passive IO that contains media content (e.g. an audio file) and can contain embedded metadata. The locations 1170, 1340 1360 and 1380 are represented as location RWEs 2170, 2340, 2360 and 2380 respectively. The cities of San Francisco 1100 and New York 1300 are represented as location RWEs 2100 and 2300 respectively (they could also be represented as topical IOs.) External data providers 1600 and social networking sites 1800 are represented as active IOs 2600 and 2800 respectively.

The W4 COMN collects spatial data, temporal data, RWE interaction data, IO content data (e.g., media data), and user data including explicitly-provided and deduced social and relationship data for all of the RWEs shown in FIG. 9. Such data can include all of the electronic and interaction data as described in detail above.

Figure 10:
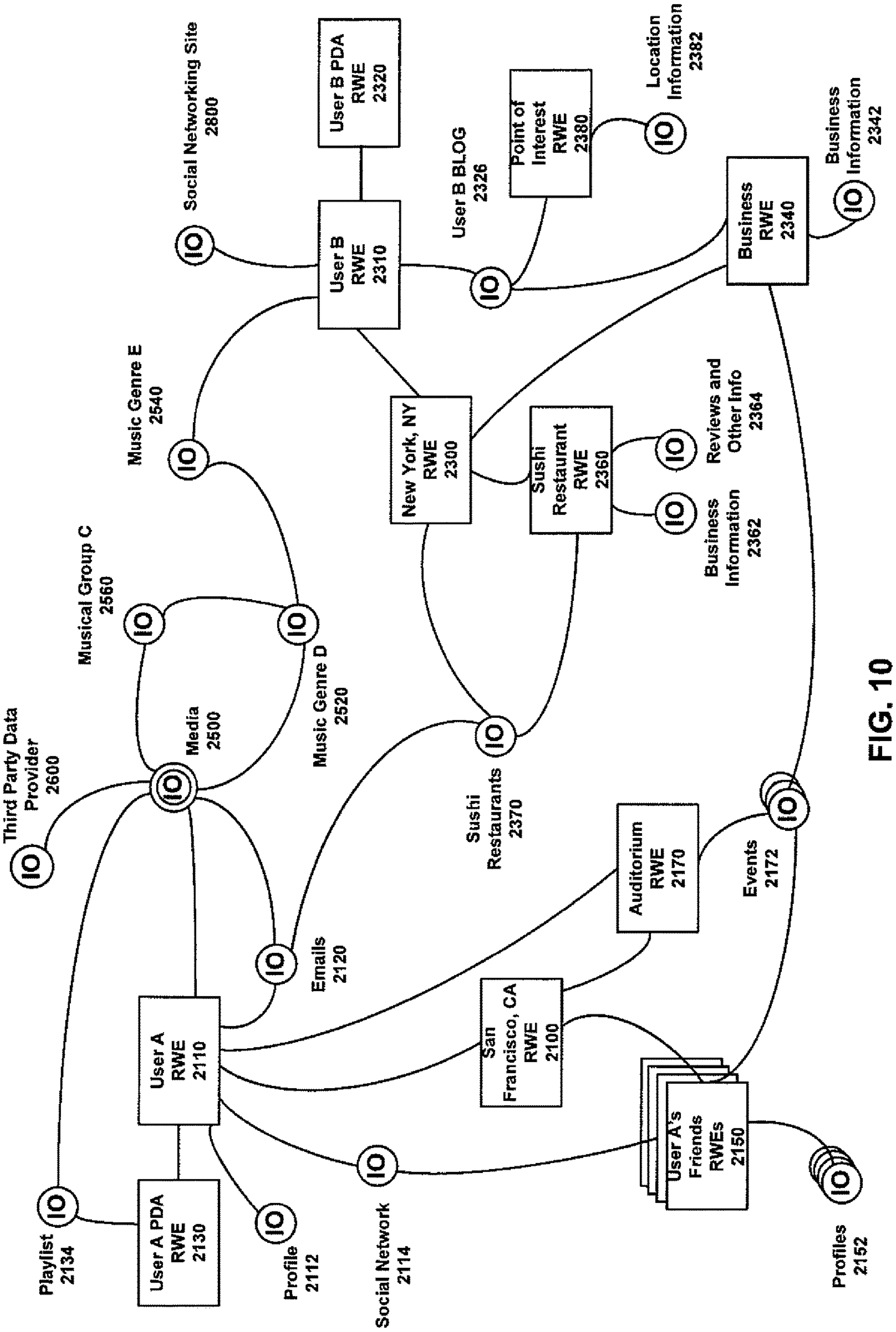
FIG. 10 illustrates one embodiment of a data model showing how the RWEs shown in FIG. 9 can be related to entities and objects within a W4 COMN.

FIG. 10 illustrates one embodiment of a data model showing how the RWEs shown in FIG. 9 can be related to entities and objects within a W4 COMN.

The RWEs for User A 2110 and User B 2310 are each associated with proxy RWEs, 2130 and 2320 respectively, representing devices used by users. In the illustrated embodiment, the proxy RWEs 2130 and 2320 represent PDAs, however any network connectable device, such as cell phones, media players, laptop computers and so forth, can be represented as proxy RWEs within a W4 COMN.

The RWEs for User A 2110 and the RWEs for User's A's friends 2150 are currently associated with a location RWE for San Francisco 2100. The RWE for User B 2310 is associated with a location RWE for New York 2300. In the illustrated embodiment, users' association with location RWEs is a dynamic relationship based on the user's real-time geo-location. For example, if User A flies to New York, User A's RWE 2110 would then be associated with the RWE for New York 2300. A user RWE can also be associated with a location RWE through any other kind of relationship known to the W4 COMN between a user and a location, for example, the user's residence or place of birth.

User RWEs and Proxy RWEs can be directly or indirectly associated with one or more IOs which can contain or reflect, without limitation, user demographic data, user interests, user media libraries and published content such as blogs, photos or videos, user's ecommerce sites, user social networks, user associations, transactions, surfing history, search history, communication events and communications content data.

In one embodiment, the W4 COMN builds profiles of a user over time by collecting data from the user or from information sources available to the network to gain an understanding of where they were born, where they have lived, and where they live today. Using social data, the W4 COMN can also create an overlapping social network profile that places the user in a temporal, geographic and social graph, thus determining where a user lived when and with whom. User RWEs can be also be associated with other RWEs through interaction data. Users who are interested in the same time/place can declare their interests and be connected to a topic based social network through, for example, an IO relating to a topic.

In the illustrated embodiment, user RWEs 2110 and 2150 are directly associated with profile IOs 2112 and 2152, respectively, that contains demographic information about the users and can additionally contain additional user data such as hobbies, interests, and the like. The RWE for User A 2110 is further directly associated with an IO representing one or more emails 2120 which User A has sent over a period of time. The W4 COMN can track, archive and analyze the user's emails to extract interaction data that can be used to identify data relationships.

The RWE for User A 2110 is directly associated with an IO for a social network 2114. The IO for User A's social network 2114 can be populated using any methodology that enables the network to identify persons with whom User A has some form of relationship. In one embodiment, User A can specifically identify persons within his or her social network, and can further tag individuals as business contacts, friends or family. In one embodiment, the system automatically identifies User A's friends and family by parsing and analyzing the content of emails or other interaction data created by User A and directed to other persons. In the illustrated embodiment, the IO representing User A's social circle 2114 is associated with a plurality of RWEs for individuals 2150 identified as User A's friends.

RWE for User A 2110 is associated with the RWE for an auditorium 2170 located in San Francisco. The association between the RWE for User A and the RWE for the auditorium 2170 exists because User A's current geo-location indicates User A is in the auditorium. The relationship is dynamic and transient, since User A will only remain in the auditorium for a brief period. The RWE for the auditorium 2170 is additionally associated with the RWE for San Francisco 2100 because the auditorium is physically located in San Francisco. In this case, since the auditorium is a fixed location, the association between the RWE for the auditorium 2170 and the RWE for San Francisco 2100 is relatively static, and can be determined by static information, such as the auditorium's mailing address.

The RWE for the auditorium 2170 is further associated with one or more IOs for events 2172 occurring at the auditorium. The IOs for events 2172 contains sufficient information to determine what event, if any, event is taking place at the auditorium at any given time. In the example, no event is taking place at the auditorium at the moment User A is located in the auditorium. If, on the other hand, if User A was located in the auditorium at the same time an event was occurring, it could create a relationship between the RWE for User A 2110 and the IO for a scheduled event 2172. The RWEs for some of User A's friends 2150 are associated with IOs for one or more events 2172 at the auditorium. The RWEs for one or more of User A's friends 2150 may be associated with an IO for an event 2172, for example, because they purchased tickets online and received a confirmation email detected by the system.

The RWE for User B 2310 is associated with an IO User B's BLOG 2326. The IO for the BLOG is directly associated with an RWE for a point of interest 2380 and an RWE for a business 2340. In the example, the IO for the BLOG is directly associated with RWE 2380 and RWE 2340 because the content of the BLOG that User B enjoyed a visit to the point of interest and also indicates that User B is a patron of business 2340. The RWEs for the point of interest 2380 and the business 2340 are both associated with the RWE for New York 2300 because both have mailing addresses located in New York. The RWEs for the point of interest 2380 and the business 2340 are both associated with passive IOs containing location information 2382 and business information 2342 respectively. The RWE for User B 2310 is further associated with an active IO for a social networking site 2800. The relationship between the RWE 2310 and the IO 2800 may have been detected, for example, because User B listed the site on his or her profile or referred to it in interaction data. Alternatively, the network may have automatically matched users on the social networking site to users known to the W4 COMN.

The RWE for the sushi restaurant 2360 is associated with the RWE for New York 2300 the restaurant is physically located in New York. The RWE for the sushi restaurant 2360 is associated with a passive IO relating to business information 2362 regarding the restaurant, such as business hours and menus. The RWE for the sushi restaurant 2360 also is associated with a passive IO relating to reviews and other third party information 2364 regarding the restaurant. Note such data may be stored in the IO or could be linked from a third party data source available to, but external to the W4 COMN, such as a website for a local newspaper. The RWE for the sushi restaurant is associated with a topical IO 2370 for sushi restaurants in New York. The relationship was determined in this case since the RWE for the restaurant 2360 is associated with the RWE for New York 2300 and the IO for business information 2362 indicates the restaurant serves sushi.

The media User A is currently listening to is contained within a media IO 2500. The media IO 2500 is associated with an IO for a playlist 2174 associated with a proxy RWE for User A's PDA because the media contained within the IO 2500 is listed on a playlist on the PDA. The media IO 2500 is also directly associated with the RWE for User A 2110. The association could have been determined, for example, by the fact that the media IO 2500 is associated with an IO for a playlist 2174 which is indirectly related to User A's RWE 2110 through proxy RWE 2130. Alternatively, the relationship could have been determined by other data relating to User A, for example, User A may have listed the subject of IO 2500 as one of his or her favorite songs in User A's profile IO 2112.

The media IO 2500 is further directly associated with associated with a topical IOs relating to musical group C that performed the song 2560 and a topical IO 2520 for the genre of music D that the music can be classed under. The associations may have been determined through metadata in the IO 2500 itself, or through any other data available to the network that indicates that such associations exist (e.g. newspaper articles, billboard listings or the like.) The IO for music genre D 2520 is further associated with a topical IO for a larger musical genre E 2540 that encompasses genre D. The relationship could have been determined by the content of the IOs 2540 and 2560, or alternatively, could have been derived from other sources available to the network.

The RWE for User B 2130 is indirectly associated with the media object 2500. The User B listens to music generally falling under music genre E, but never listens to music in genre D, and has never even heard of the song relating to media IO 2500. Nevertheless, User B 2130 is indirectly associated with the media object 2500 because the topical IO for genre E is associated with the topical IO for genre D 2520 because genre E 2560 is a larger genre that encompasses genre D, and the media object 2500 is associated with genre B, for example, through metadata in the media object.

RWE for User B 2310 is associated with the topical IO for music genre E 2540 because User B listens to music that can be generally categorized under genre E. The system may have detected User B's interest in genre E based on, for example, User B's profile on the social networking site related to active IO 2800, or on User B's interaction data on the network. Genre E 2540 represents a broad category (e.g. rock music). User B 2320 has never expressed an interest in the small genre encompassed by genre D 2520 (e.g. grunge), nor in musical group C 2560, however, User B 2310 is indirectly associated with the media object 2500 because the media object is associated with the IO for genre D 2520, which is associated with the IO for genre E 2540 which is associated with the RWE for User B 2320.

The RWE for User A 2130 is indirectly associated with the topical IO for sushi restaurants 2370 in New York through the IO relating to User A's emails 2120. In the illustrated embodiment, the association was formed because User A has expressed an interest in sushi restaurants located in New York in an email 2120. Through the topical IO 2370, User A 2130 is indirectly associated with the RWE for the sushi restaurant 2360, and though a chain of associations, all of the RWEs directly or indirectly associated with the RWE for New York 2300. User B, meanwhile, hates sushi and the RWE for User B 2310 has no direct association with the IOs or RWEs relating to the sushi restaurant 2360.

In one embodiment, the strength or "interestingness" of the association between any two RWEs or IOs can be measured by number of intervening objects, which can also be stated as degrees of separation (i.e. a direct association is one degree of separation, one intervening object two, and so forth.) The strength of the association between any two RWEs or IOs can additionally or alternatively measured by the number of parallel chains of association that connect two RWEs or IOs. For example, the RWE for User A is indirectly related to the RWE for User B through three parallel chains of association, one through the media IO 2500, one through the topical IO for sushi restaurants in New York 2370 and one through the IO for an event 2172 at the auditorium 2170 in San Francisco.

The RWE for the business 2340 is directly associated with the IO for events 2172 at the auditorium in San Francisco. The association was formed because the business associated with RWE 2340 is sponsoring an event at the auditorium. The association may have been detected, for example, using the content of the events IO 2172, or though another source such as advertisements published the business associated with RWE 2340 that are available to the network. Through the event IO 2172, the RWE for the business 2340 is indirectly relate to the RWE for the auditorium 2170, the RWE for San Francisco, and all IOs and RWEs associated, directly or indirectly, with the RWE for San Francisco 2100.

This illustration provides a good example of how a W4 can find relationships between people where, at first glance, none exist. User A and User B are in different cities, User A has listened to the song associated with media IO 2500 and likes music group A, User B has not listened to the song, and, in fact, doesn't listen to music in genre D. User A likes sushi, User B hates sushi. User B patronizes the business associated with RWE 2340, User A has never heard of the business. Yet, after all the data is considered, User A and User B are indirectly related though at least three parallel data paths.

In one embodiment, within a W4 COMN, the relationships shown in FIG. 10 are built and maintained by one or more correlation engines within a W4 engine that services the W4 COMN at regular intervals to refresh user and transaction databases from the constantly accruing data stream created by users, devices, proxies and in the real world. Using social, spatial, temporal and topical data available about a specific user, topic or logical data object, every entity known to the W4 COMN can be mapped and represented against all other known entities and data objects in order to create both a micro graph for every entity as well as a global graph that relates all known entities with one another. In one embodiment, such relationships between entities and data objects are stored in a global index within the W4 COMN. The creation of such relationships may be automatic and part of the normal operation of the W4 COMN. Alternatively, some or all of the relationships may be created on demand when, for example, a context query is executed.

Figure 11:
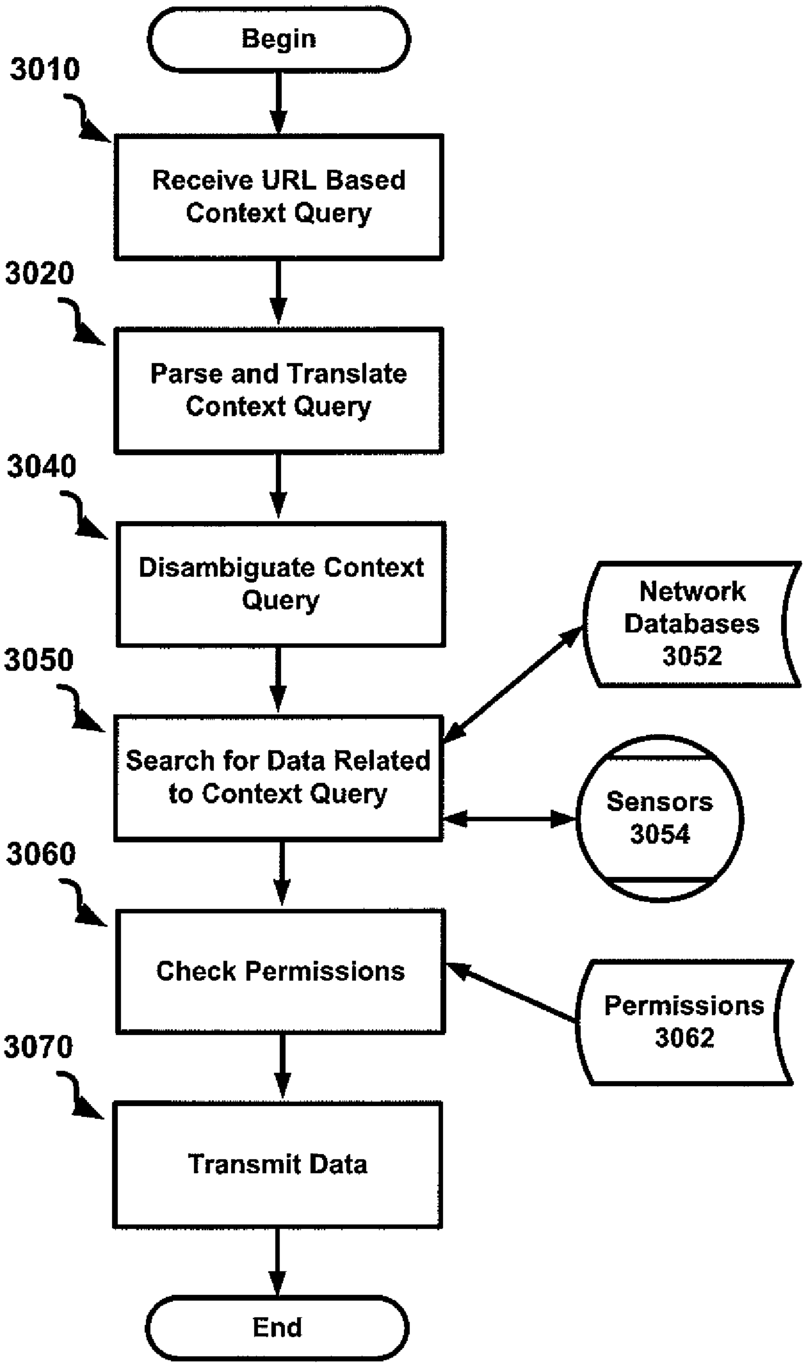
FIG. 11 illustrates one embodiment of a process 3000 of how a network containing temporal, spatial, and social network and topical data for a plurality of users, devices, and media (such as a W4 COMN), can be used to support URL based context queries.

FIG. 11 illustrates one embodiment of a process 3000 of how a network containing temporal, spatial, and social network and topical data for a plurality of users, devices, and media (such as a W4 COMN), can be used to support URL based context queries.

The process begins when a URL containing a context query 3010 containing at least one context criteria is received from a user. The URL can be entered using a user proxy device such as, for example, a portable media player, PDA, computer, or cell phone. The context query within the URL can include any combination of any who, what, when, or where criteria. In one embodiment, the criteria can be related to one another using standard relational or set operators. In one embodiment, the query can be stated as a natural language query. In one embodiment, the criteria are formatted as a string of criteria-attribute/value pairs as described above under the heading URL BASED QUERY FOR RETRIEVING DATA RELATED TO A CONTEXT and in the general format http://<query server>/[<criteria-attribute>/<value>/]

where, in one embodiment, the relationship between the criteria can be determined by the selection of criteria attributes and the order of criteria within the query. The URL can be entered by the user in any manner known to the art. For example, the URL could have been directly entered by the user, could have been a link on a webpage or could have been generated by a software application.

The context query is then parsed and translated 3020 to place context criteria into a standard format. For example, the "where" criteria value strings "701+first+avenue,sunnyvale,ca" "701+first+avenue,94089" refer to the same location, and are both translated to the same format. Criteria values can, in general, be translated to any standard format based on the data type of the criteria attribute, for example, the strings above could be translated to Geotudes. Where the criteria value does not match the domain of the context criteria, the criteria value is checked to determine if it is a valid relational or symbolic reference.

Where a query points to an identifier for a context query stored on the network, for example:

http://w4.yahoo.com/djktlec the context query is imported from its source and is parsed and translated like any other context query.

Context criteria are then disambiguated 3040 to absolute (i.e. canonical) values. In one embodiment, there are at least related types of disambiguation that can occur relating to relational references, aliased references, and ambiguous references. Relational references are symbolic references to the user's context or to the context of an entity referred to in the query. For example "who/me" is disambiguated to the user entering the query, whereas "who/User+A/who-where/there" is disambiguated to User A's current location. Aliased references are references where the criteria value is essentially "shorthand" for entities within the user's context. For example, the term "Joe" will mean different things to different people and is determined based on the social context of the user that is accessing the URL (e.g. two persons may each have a friend with the first name of "Joe", but different last names.)

Ambiguous references are references that, while intended to identify a specific who, what, when or where, contain incomplete information. For example, suppose a user wanted to retrieve data for art galleries selling Chinook (a pacific northwestern Indian tribe) art in Portland, Oreg.

http://w4.yahoo.com/who/gallery/what/chinook+art/where/portland

There are at least two major cities named Portland (Oregon and Maine). Nevertheless, since the Chinook tribe is located close to Portland, Oreg. and very far from anywhere in Maine, the reference could be disambiguated to "portland+oregon." A similar result could also be obtained in the user was geo-located in Portland, Oreg.

The parsed, translated and disambiguated context criteria are the used to formulate a database query based on the context criteria so as to search 3050, via the network, for user profile data, social network data, spatial data, temporal data and topical data that is available via the network, including network databases 3052 and sensors 3054, that relates to the context. In one embodiment, the criteria are interpreted to take advantage the best available data within the network. A context may be defined in general terms, but the proper data and access paths may not be apparent to an end user. For example, assume a user wants to enter a query to retrieve the favorite music of surfers in Hawaii in 1974. A URL based context query could read:

http://w4.yahoo.com/who-interest:surfing/who-where:hawaii/who-what:favorite+music/who-when:1974

One interpretation of such a query would be to retrieve songs in the genre "surf music", released in 1974 whose lyrics reference Hawaii. Such an interpretation may be appropriate if the network has data limited to music metadata, but does not fully address the query—surfers in Hawaii 1974 might have liked blues or jazz. The requesting user may, be unaware of, or may not fully appreciate that, the network stores data for a large number of other users. A subset of such users may be users whose hobby is surfing and who lived in Hawaii in 1974.

The query could search for users known to the network whose profile or interaction data indicate have surfing as a hobby or interest and who lived in Hawaii in 1974. The musical preferences of such users, such as musical genre, favorite artists, or favorite songs could then be used to search for media objects for songs relating to such genre, artists, or songs and which were released in 1974.

In one embodiment, queries automatically use data relating the user entering the query, such as user profile data, user interaction data, user media data and user interest data to identify data relating to the context that is of the most interest to querying users. For example, if a user who likes Jazz entering a context query of "where/manhattan/when/next-week/what/music", the system could identify data objects relating to Jazz as of most interest. Less interesting objects could be filtered out, ranked lower in a result set of a context query. Additionally less "interesting" data, such as data distantly related to the explicit context entered could become more "interesting." Thus, a hotel may only be distantly related to music, but may have been the favorite hotel of a Jazz musician.

The format of the database query may be human readable or may be expressed in a format that reflects the internal operations of the W4 COMN at the time the query is formulated. Data available to W4 COMN can be distributed across multiple points of storage within the W4 COMN, some of which may be relatively transient, including user devices such as media players and so forth. Data available to the network may also originate from sensors known to the network or third party websites external to the W4 COMN. As technology evolves, and the global architecture of the Internet changes, more network addressable data sources may become available, and are within the scope of this disclosure, As such, the database query may involve multiple retrieval steps, sorting, merging and translating retrieved data, and so forth. In one embodiment, the system uses a global index of data available to the network to retrieve data. The results of the query can, in one embodiment, initially comprise a set of data objects or a set of network references to data objects and W4 objects. Since as is obvious from the FIG. 10, substantially all objects in a W4 COMN can be related directly or indirectly to a virtually unbounded set of W4 objects, it may be necessary to use various techniques to narrow the result set. In one embodiment, only those objects within a threshold number of degrees of separation from query criteria are included in a narrowed result set. In one embodiment, only those objects that show a minimum number of parallel paths of associations to the context criteria are included in the narrowed result set. In one embodiment both degrees of separation and parallel association paths are included. In one embodiment, different techniques are used for different classes of objects.

The permissions associated with each RWE owned object and relationship in the result set are then checked 3060. In one embodiment, permissions 3062 for RWE owned objects are stored on a computer readable medium. In one embodiment, the step for checking permissions is the process illustrated in FIG. 17, which is described in detail below. If the user executing the context query does not have permission to access RWE control data, the data is removed from the result set. In an unsecured system, or where no RWE controlled data exists in the result set, this step can be optional The result set is then transmitted to the end user 3070. The data may be transmitted to the user in any suitable electronic format. In one embodiment, the result set is presented to the end user as a dynamic web page, that can additionally include related URLs. In one embodiment, the process for transmitting the result set to the end user is the process illustrated in FIG. 15, which is described in detail below.

Figure 12:
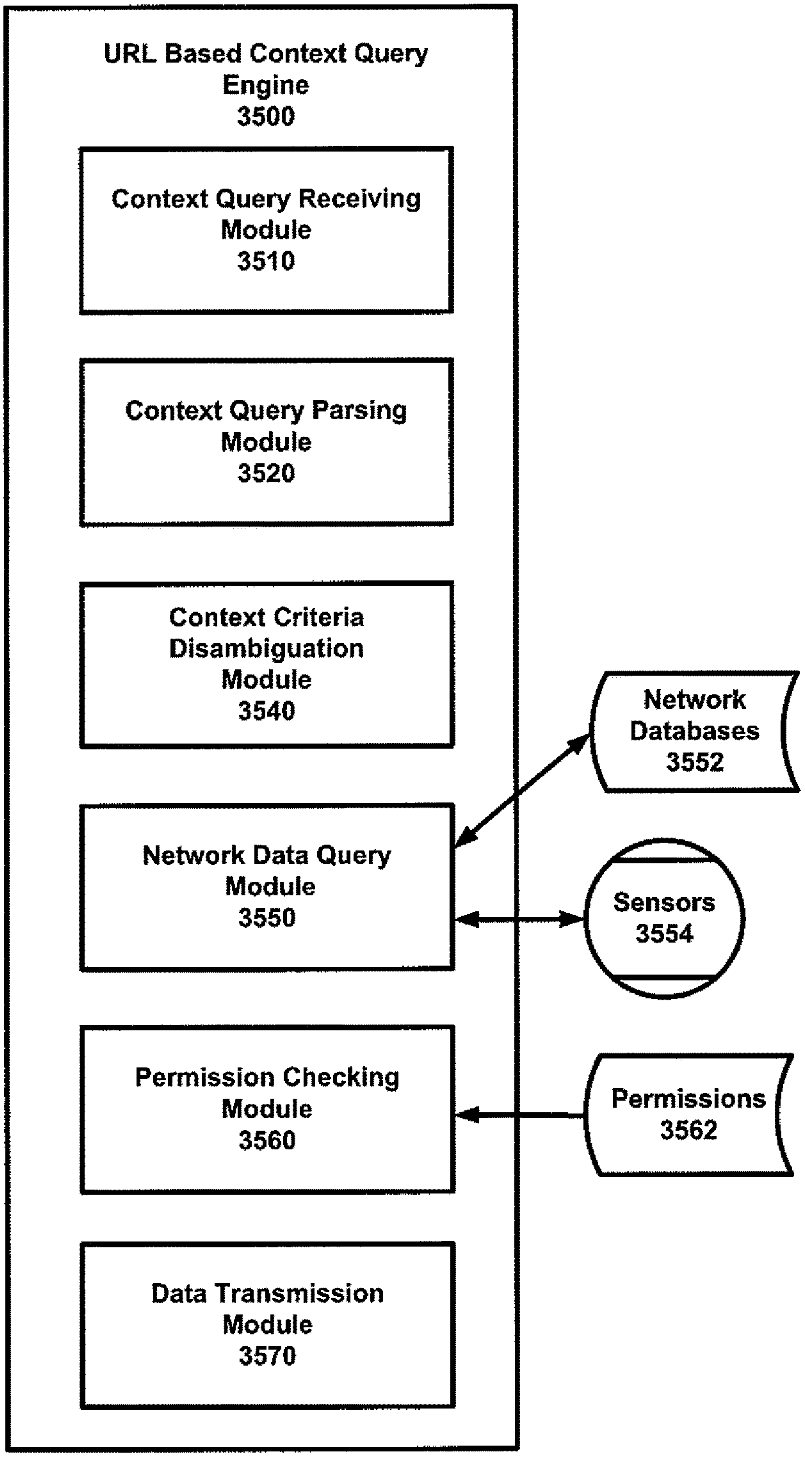
FIG. 12 illustrates one embodiment of a URL based context query engine 3000 that is capable of providing processing URL based context within a W4 COMN or other network providing similar data and processing capabilities.

FIG. 12 illustrates one embodiment of a URL based context query engine 3500 that is capable of providing processing URL based context within a W4 COMN or other network providing similar data and processing capabilities.

A URL based context query engine 3500 resides on a server within the W4 COMN. The context query engine 3500 can be a component of a W4 engine, or, alternatively, may use services provided by components of a W4 engine or any of its constituent engines. The context query engine 3500 comprises a context query receiving module, 3510, a context query parsing module 3520, a context criteria disambiguation module 3540, a network data query module 3550, a permission checking module 3560 and a data transmission module 3570.

The context query receiving module 3510 is configured to receive URL based context queries containing at least one context criteria. Such URL based context queries are generally in the format:

http://<query server>/<context query> where the <context query> is a query that can contain any who, what, when and where criteria. In one embodiment, the context query receiving module is capable of receiving context queries substantially similar to those describe above in greater detail.

In one embodiment, at least some of such URL based context queries are composed by a users and entered in directly, for example, in the address bar of web browsers and at least some of such URL based context queries are embedded as hyperlinks in a webpage that users click on. In one embodiment, at least some of such URL based context queries are entered in using an interface provided by context query receiving module 3510. The interface may be a graphical user interface displayable on computers or PDAs, including HTTP documents accessible over the Internet.

The context query within the URL can include any combination be any who, what, when, or where criteria. In one embodiment, the criteria can be related to one another using standard relational or set operators. In one embodiment, the query can be stated as a natural language query. In one embodiment, the criteria are formatted as a string of criteria-attribute/value pairs as described above and in the general format http://<query server>/[<criteria-attribute>/<value>/]

where, in one embodiment, the relationship between the criteria can be determined by the selection of criteria attributes and their order within the query.

The context query parsing module 3520 is configured to parse and translate context criteria to place the criteria into a standard format. The context query parsing module 3520 can be further configured to check criteria values to insure criteria values match the domain of the context criteria or are valid relational or symbolic references. The context query parsing module 3520 can be further enabled to import and parse queries associated with an an identifier for a context query stored on the network, for example:

http://w4.yahoo.com/djktlec can be the context query is imported from the server and is then parsed like any other query.

The context criteria disambiguation module 3540 is configured to disambiguate parsed context queries to a context query containing, in one embodiment, absolute (i.e. canonical) values. In one embodiment, the context criteria disambiguation module 3540 can disambiguate relational references, aliased references, and ambiguous references. Relational references are symbolic references to the user's context or to the context of an entity referred to in the query.

The network data query module 3550 is configured to use disambiguated context queries to formulate database queries based on the context criteria so as to search via the network, for user profile data, social network data, spatial data, temporal data and topical data that is available via the network, including network databases 3552 and sensors 3354, and relates to the context. In one embodiment, the network database query module 3550 is configured to automatically use data relating to querying users, such as user profile data, user interaction data, user media data and user interest data to identify data relating to the context that is of the most interest to querying users. In one embodiment, the network database query module 3550 is configured to take advantage the best available data within the network. In one embodiment, the network data query module 3550 is configured to use a global index of data available to the network to retrieve data.

The format of the database query formulated by the network database query module 3550 may be human readable or may be expressed in a format that reflects the internal operations of the W4 COMN at the time the query is formulated. The network database query module 3550 is, in one embodiment, further configured to narrow the result set from the query by filtering out data that is not closely related to content criteria. In one embodiment, only those objects within a threshold number of degrees of separation from query criteria are included in a narrowed result set. In one embodiment, only those objects that show a minimum number of parallel paths of associations to the context criteria are included in the narrowed result set. In one embodiment, both degrees of separation and parallel association paths are included. In one embodiment, different techniques are used for different classes of objects.

The permission checking module 3560 is configured to check permissions associated with each object and relationship in result sets returned by the network database query module 3550 and to remove RWE controlled data from the result set that the querying user does not have permission to view. In one embodiment, permissions for RWE owned objects are stored on a computer readable medium 3562. In one embodiment, the permission checking module 3560 is the context data permission engine shown in FIG. 18, which is described in greater detail below. In an unsecured system, or where no RWE controlled data exists in the result set, this module can be optional The data transmission module 3570 is configured to transmit result sets produced by the network data query module 3550 and the permission checking module 3560 to querying users. In a fully secured system, in one embodiment, the data transmission module 3570 is configured to receive result sets solely from the permission checking module 3560. In an unsecured system, in one embodiment, the data transmission module 3570 is configured to receive result sets solely from the network data query module 3550. In one embodiment, data transmission module 3570 is configured to present the result set to the end user as a dynamic web page, that can additionally include related URLs. In one embodiment, the data transmission module 3570 is the context webpage generation engine 5500 shown in FIG. 16, which described in greater detail below.

Relating the above principles to the real world and data models presented in in FIG. 8-FIG. 10, suppose on June $21^{st}$, User A (FIG. 8-9, 1130) is in San Francisco and wants to know what his/her friends in San Francisco are up to next week and enters the URL based context query:

| |
|---|
| http://w4.yahoo.com/who/friends/who-where/San+Francisco+CA/who-when/next-week |

The parameters "friends", and "next-week" are parsed and recognized as relational parameters. The parameter "San+Francisco+CA" is, first parsed, in one embodiment, to the tokens for "San" "Francisco" "CA". Since the "where" is not qualified as the "where" of another time (e.g. San Francisco in 1908), "San" "Francisco" "CA" can be translated to a standardized canonical format representing San Francisco as it is currently defined. Such standardized format could be a standardized string such as "San Francisco, Calif., U.S.A", a set of tokens, a polygon expressed by a set of coordinates, a Geotude or any other standardized format best optimized for use by succeeding query steps.

The relational parameters are the disambiguated to canonical values. The parameter "next week" is disambiguated to absolute dates reflecting the period Jun. 22-Jun. 28, 2008 and is translated to a standardized date range format such as, for example, a string, iCal format, UNIX time or any other form suitable for query processing. The relational parameter friends could be disambiguated by referring to User A's social network (FIG. 10, 2224) to obtain a detailed list of persons associated with RWEs (FIG. 10, 2250) associated with User A's social network. Alternatively, the parameter could be disambiguated to a canonical data relationship expression such as, for example "RWE 2110:IO 2224:RWE:friend", where the relationship refers to unique IDs for the RWEs and IOs which define the relationship.

The translated and disambiguated query is then used to search the entities and data relationships shown in FIG. 10 for data objects related to the context. In the illustrated example, the query also automatically uses User's A's profile (FIG. 10 2112), interaction data (FIG. 10, 2120), and media data (FIG. 10 2500) to help refine the query. The query determines that an RWE associated with one of User A's friends (FIG. 10 2250 is associated with an IO for an event (FIG. 10, 2272) associated with RWEs for an auditorium (FIG. 10 2170) and business (FIG. 10, 2340). The RWE for the business is further associated with an IO for a BLOG (FIG. 10, 2326) rating the business, which is associated with the RWE for User B (FIG. 10, 2310.)

User B's RWE (FIG. 10, 2310) is relatively distant from the explicit context of the query. However, in one embodiment, the process recognizes that User B's RWE is associated with an IO for a music genre E (FIG. 10, 2540) which is related to at least one media object (FIG. 10 2500) related to User A's playlist (FIG. 10, 2134.) The RWE for User B is also related to the RWE for New York 2300, which is related an RWE for a sushi restaurant 2360, which is related to an IO for User A's emails 2370. Thus, User B may be sufficiently "interesting" enough to be included in the result set from the query.

Figure 13:
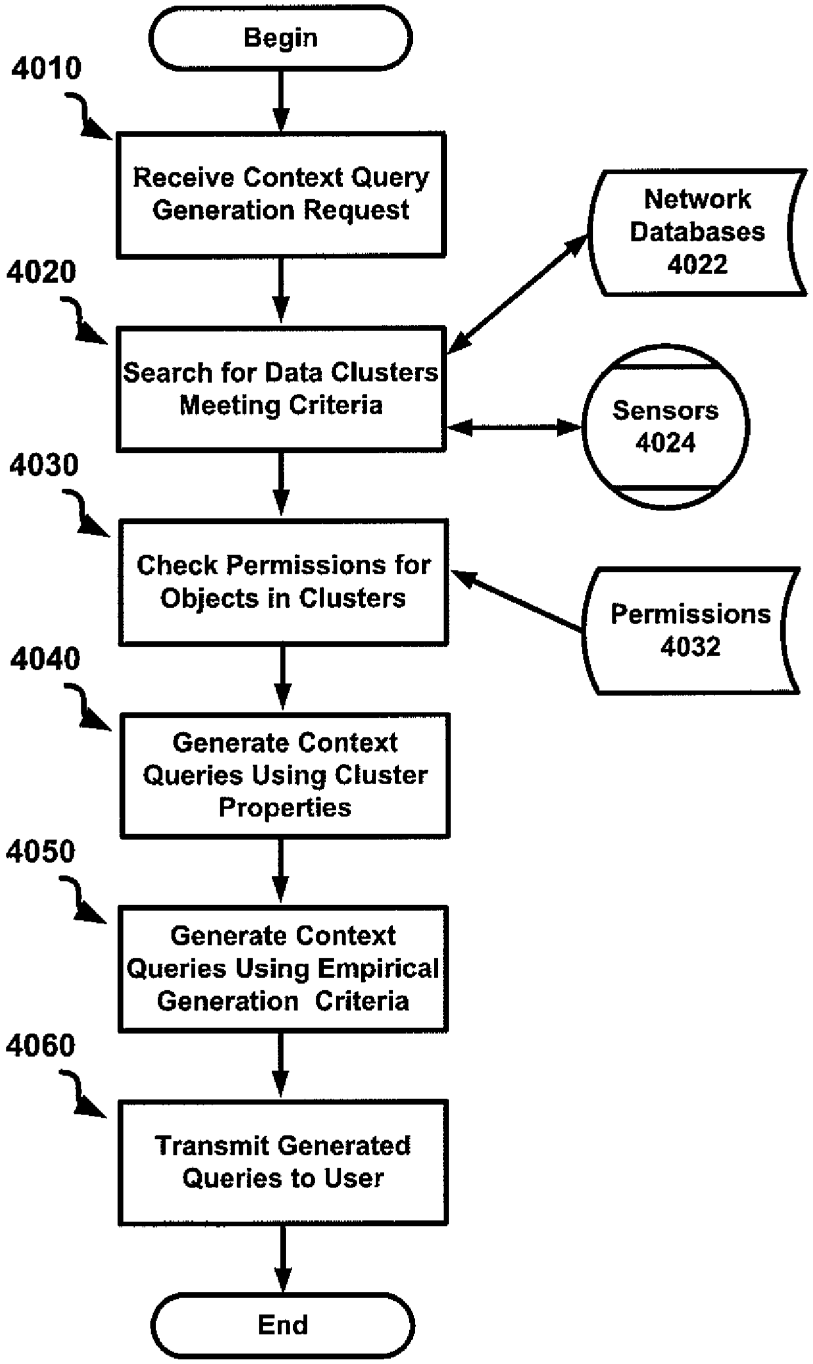
FIG. 13 illustrates one embodiment of a process 4000 of how a network containing temporal, spatial, and social network and topical data for a plurality of users, devices, and media (such as a W4 COMN), can be used to generate and publish URL based context queries.

FIG. 13 illustrates one embodiment of a process 4000 of how a network containing temporal, spatial, and social network and topical data for a plurality of users, devices, and media (such as a W4 COMN), can be used to generate and publish URL based context queries.

The process begins when a request for context query generation containing at least one query generation criteria is received 4010 from a user or process. Query generation criteria can provide any type of parameters that serve to define or limit context query content. A W4 dataspace can comprise billions or even trillion of data objects and relationships. Context queries could, in theory, be formulated for every individual objects or relationship. Hence, limitations are necessary.

In one embodiment, context query generation can be based on data clusters within a W4 dataspace or other similar multidimensional dataspace, as described in detail above under the heading GENERATION OF URL BASED CONTEXT QUERIES. With respect to data cluster based context query generation, query generation parameters can include data axis limitations, data value limitations, and clustering thresholds.

In one embodiment, a W4 dataspace can be configured to support at least four data axes: spatial, temporal, social and topical axes. As described above, data clusters can exist on one or more axes. Thus, a context generation criteria could contain a data axis limitation, for example <search-axis>,[<data-axis>],[AND/OR/XOR]/

Where <axis-name>] could be "who", "what", "when", or "where", and any number of the dimensions can be included separated by relational operators AND/OR/XOR. More complex syntaxes are possible, but the clustering paradigm is well suited to use of simple set operations. Note that the syntax of the following query generation criteria are intended to be illustrative, and not limiting, and other formats expressing similar logical relations are intended to be within the scope of the disclosure.

Such a search parameter instructs the system to search for data clusters along each included axis. Where criteria are separated by AND, only data clusters which are clustered on both axes are selected. Where criteria are separated by OR, data clusters which are clustered on either axis are selected. Where criteria are separated by XOR, data clusters which are clustered on the first axis, but not the second axis are selected. For example:

search-axis,where,AND,when instructs the process to search for clusters on the temporal and spatial axes. Such query generation parameter can be considered "unseeded" query generation, since no seed value is given for a starting point in the W4 dataspace, but, rather, the entire database is scanned and clusters are selected based only on cluster thresholds (discussed below.)

The <search> parameter could be extended by allowing the specification of axis data values. For example:

<search>,[<data-axis>:<axis-value>]

where <axis-value> can be any kind of canonical, relational, or symbolic value or range of values that is valid for the axis. For example:

search-axis,where: San+Francisco+CA,AND,when:yesterday-today instructs the process to search for clusters on the temporal and spatial axes where the spatial axis corresponds to San Francisco and the temporal axis corresponds to a 48 hour range for yesterday through today.

Such query generation parameters can be considered "seeded" query generation, since at least one seed value is given for a starting point in the W4 dataspace, and limits the properties of data clusters that are selected.

Additionally, clustering thresholds can be useful. In one embodiment, a clustering threshold could specify a minimum number of data objects within selected cluster. For example:

<threshold-cluster>,<number-of-objects>

A cluster limit could be further extended to limit clusters containing a certain number of objects of a given type. For example:

<threshold-class>,<number-of-clusters> where <threshold-class> can be any class of data objects within the W4 COMN. For example:

threshold-cluster,100, limits selections to clusters with 100 objects. Whereas threshold-cluster,100,media,10 limits selections to clusters with 100 objects and having at least 10 media objects.

Where data axes or cluster limits are not provided, the process can, in one embodiment, use default data axes and cluster limits, for example, default axes may be the "when" and "where" axes in an "AND" relationship, and default cluster limits can be 100.

Query generation criteria can, in one embodiment, be based on a URL context query, where the system searches for clusters along subsets of the data axes implied in the context query:

http://w4.yahoo.com/who/Artist+A/what/concert/where/SanFrancisco,CA/when/20080429 could be translated to context query generation parameters:

search-axis,who,Artist+A,AND,what,concert omitting "where" and when axes, finding clusters of data relating to all of Artist A's concerts.

search-axis,what,concert,AND,where/San+Francisco,CA,AND,when/20080429 omitting "who" axes, finding data clusters relating to all concerts in San Francisco on Apr. 29, 2008.

Alternatively, the query generation parameters could be the actual result set of a context query wherein the processes searches for data clusters nearby the objects in the result set along one or more dimensions of W4 space. Each object in the result set can be considered a point in W4 space, and the process searches for nearby clusters on each of the four W4 data axes. In one embodiment, clusters that are nearby on at least one data axis are selected. In one embodiment, clusters that are nearby on two or more data axes are selected.

"Nearby" is dependant on the domain of the axis, and may be further influenced by the magnitude of context query parameters. For example, in the case of:

http://w4.yahoo.com/who/Artist+A/what/concert/where/SanFrancisco,CA/when/20080429 nearby on the "when" axis could be considered +/−7 days, since a specific date was specified. If the only date that was specified was 2008, nearby could be 2009. Nearby in the "where" axis is could be surrounding addresses (for a specific address) or surrounding communities (for a specific city). Nearby in the "who" axis could be family and friends. Nearby in the "what" axis could be related topics (e.g. different types of music)

Additionally, or alternatively, in one embodiment, in one embodiment, query generation criteria could specify that context query generation be based on empirically varying the criteria of a context query in a fixed way consistent with the domain of the criteria without reference to data density in the W4 dataspace. For example:

http://w4.yahoo.com/who/me/when/today/where/San+Francisco,CA could be empirically varied to http://w4.yahoo.com/who/me/when/yesterday/where/San+ Francisco,CA
http://w4.yahoo.com/who/me/when/tomorrow/where/San+ Francisco,CA varying "when" by +/−one day, or http://w4.yahoo.com/who/friends/when/today/where/San+Francisco,CA varying "who" to refer to a standard social relationship, or http://w4.yahoo.com/who/friends/when/today/where/Berkeley,CA varying "where" to refer to a nearby community.

If related context queries are generated empirically, there is no guarantee any data objects will be returned by such queries, but query generation may be considerably faster, and may produce acceptable results.

If query generation criteria include data clustering criteria, the system searches the W4 dataspace (including network databases 4022 and sensors 4024) for clusters that meeting such criteria 4020. In one or more embodiments, the W4 dataspace is searched and relevant clusters of data are identified using methodologies and techniques discussed in detail above. In one embodiment, the process makes use of a global index of data available to the network to identify data clusters. The result set of such a search can contain an identification of one or more data clusters, or can be a null set if no clusters meet query generation criteria.

The permissions associated with each RWE-owned object and relationship contained in clusters in the result set of the search step are then checked 4030. In one embodiment, permissions for RWE owned objects are stored on a computer readable medium 4032. In one embodiment, the step for checking permissions is the process illustrated in FIG. 17, which is described in detail below. If the requesting user is not authorized to view any objects in the cluster, the cluster is deleted from the result set. If the number of objects associated with the cluster are reduced, and cluster thresholds are in effect, cluster thresholds are reapplied, and clusters not meeting thresholds are deleted from the result set (e.g. given a cluster threshold of 100, a cluster of 90 objects is not in the result set, and a cluster of a 200 objects where the user only has permission to view 80 of the objects is initially in the result set, but is removed—the user sees the same result.)

If there are data clusters remaining in the result set, context queries can be generated using the properties of the data clusters 4040 in the result set as described above in the section labeled GENERATION OF URL BASED CONTEXT QUERIES. If query generation parameters indicate that queries are to be empirically generated (i.e. without reference to data clusters), then queries are generated empirically 4050, in one embodiment, as described above in the section labeled GENERATION OF URL BASED CONTEXT QUERIES.

Finally generated context queries are transmitted 4060 to a requesting user or process. The context queries can be transmitted to the requesting to the requesting user or process in any suitable electronic format, which could include, in one embodiment, a fully formatted URL based context query.

Figure 14:
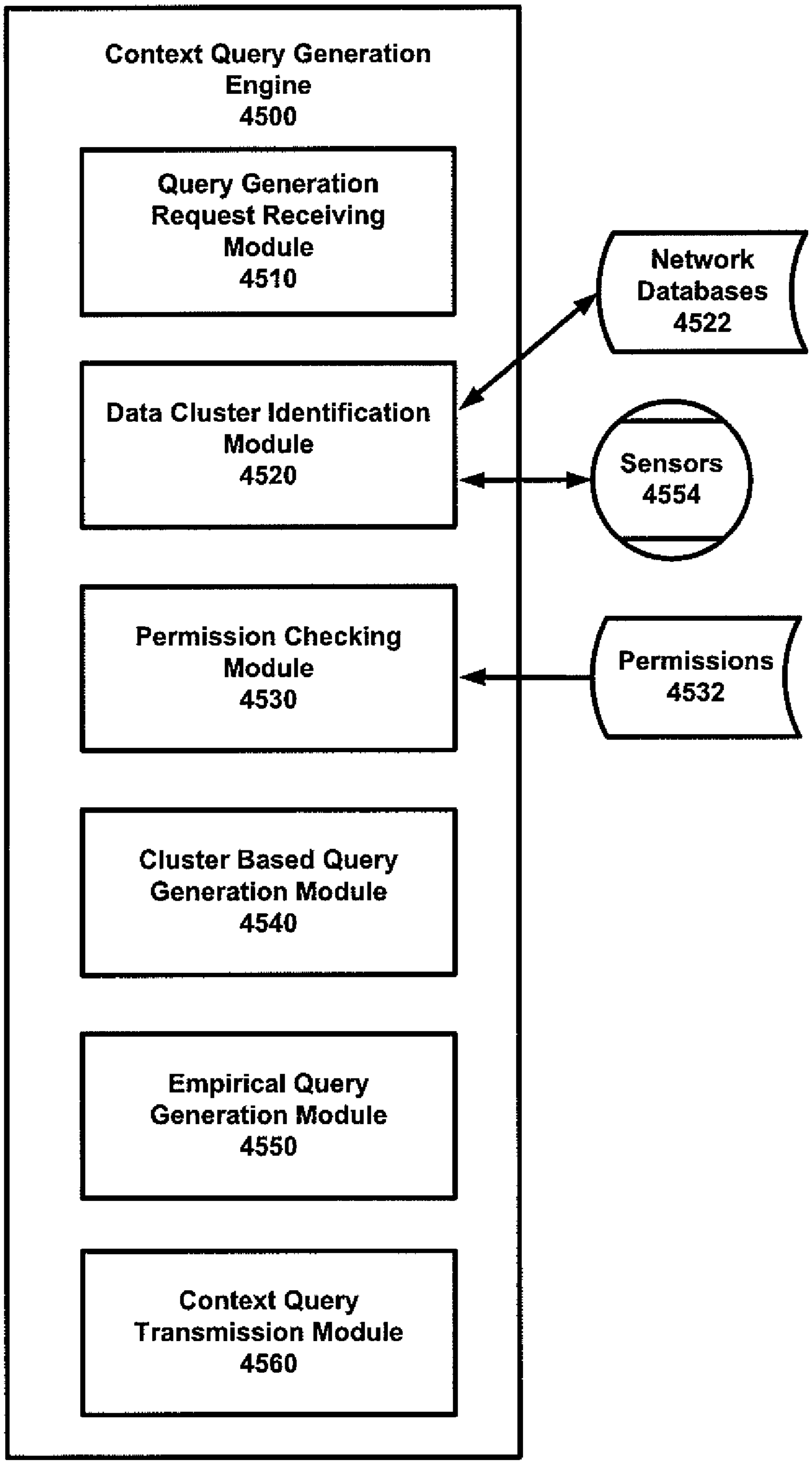
FIG. 14 illustrates one embodiment of a URL based context query generation engine 4500 that is capable of providing processing URL based context within a W4 COMN or other network providing similar data and processing capabilities.

FIG. 14 illustrates one embodiment of a URL based context query generation engine 4500 that is capable of providing processing URL based context within a W4 COMN or other network providing similar data and processing capabilities.

A context query generation engine 4500 resides on a server within the W4 COMN. The context query generation engine 4500 can be a component of a W4 engine, or, alternatively, may use services provided by components of a W4 engine or any of its constituent engines. The context query generation engine 4500 comprises query generation request receiving module 4510, a data cluster identification module 4520, permission checking module 4530, a cluster based query generation module 4540, empirical query generation module 4550 and a context query transmission module 4560.

The query generation request receiving module 4510 is configured to receive context query generation request from a users and network processes. Query generation criteria can provide any type of parameters that serve to define or limit context query content. In one embodiment, context query generation can be based on data clusters within a W4 dataspace or other multidimensional dataspace, as described in detail above. With respect to data cluster based context query generation, query generation parameters can include data axis limitations, data value limitations, and clustering thresholds.

Additionally, or alternatively, in one embodiment, the query generation request receiving module 4510 is further configured to receive generation criteria specifying context query generation based on empirically varying the criteria of a context query in a fixed way consistent with the domain of the criteria without reference to data density in the W4 dataspace.

The data cluster identification module 4520 is configured to use data clustering criteria in query generation request to search the W4 dataspace (including network databases 4522 and sensors 4524) for clusters meeting such criteria 4020. The in one or more embodiments, the W4 dataspace is searched and relevant clusters of data are identified using methodologies and techniques discussed in detail above. In one embodiment, the data cluster identification module 4520 is configured to make use of a global index of data available to the network to identify data clusters. The data cluster identification module 4520 is further configured to output result sets of such searches, where the set comprising identifications of one or more data clusters (or is a null set if no clusters meet query generation criteria.)

The permission checking module 4530 is configured to check permissions associated with each RWE-owned object and relationship contained in clusters in result sets produced by the data cluster identification module 4520. In one embodiment, permissions for RWE owned objects are stored on a computer readable medium 4532. In one embodiment, the permission checking module 3560 is the context data permission engine shown in FIG. 18, which is described in greater detail below. If the requesting user or process is not authorized to view any objects in the cluster, the cluster is deleted from the result set. In one embodiment, the permission checking module 4530 is configured to reapply cluster thresholds to data clusters where the number of objects associated with the cluster are reduced, and cluster thresholds are in effect. Clusters not meeting thresholds are deleted from the result set.

The cluster based query generation module 4540 is configured to generate context queries using result sets produced by the data cluster identification module 4520 and checked by the permission checking module 4530. In one embodiment, context queries are generated by the cluster based query generation module 4540 using the properties of the data clusters in the result set as described above in the section labeled GENERATION OF URL BASED CONTEXT QUERIES.

The empirical query generation module 4550 is configured to empirically generate queries (i.e. without reference to data clusters), where query generation criteria specify that queries are to be generated empirically In one embodiment, queries are empirically generated as described above in the section labeled GENERATION OF URL BASED CONTEXT QUERIES.

The context query transmission module 4560 is configured to transmit context queries generated by the cluster based query generation module 4540 and the empirical query generation module 4550 to requesting users and processes. The context queries can be transmitted to the requesting to the requesting user or process in any suitable electronic format, which could include, in one embodiment, a fully formatted URL based context query.

Figure 15:
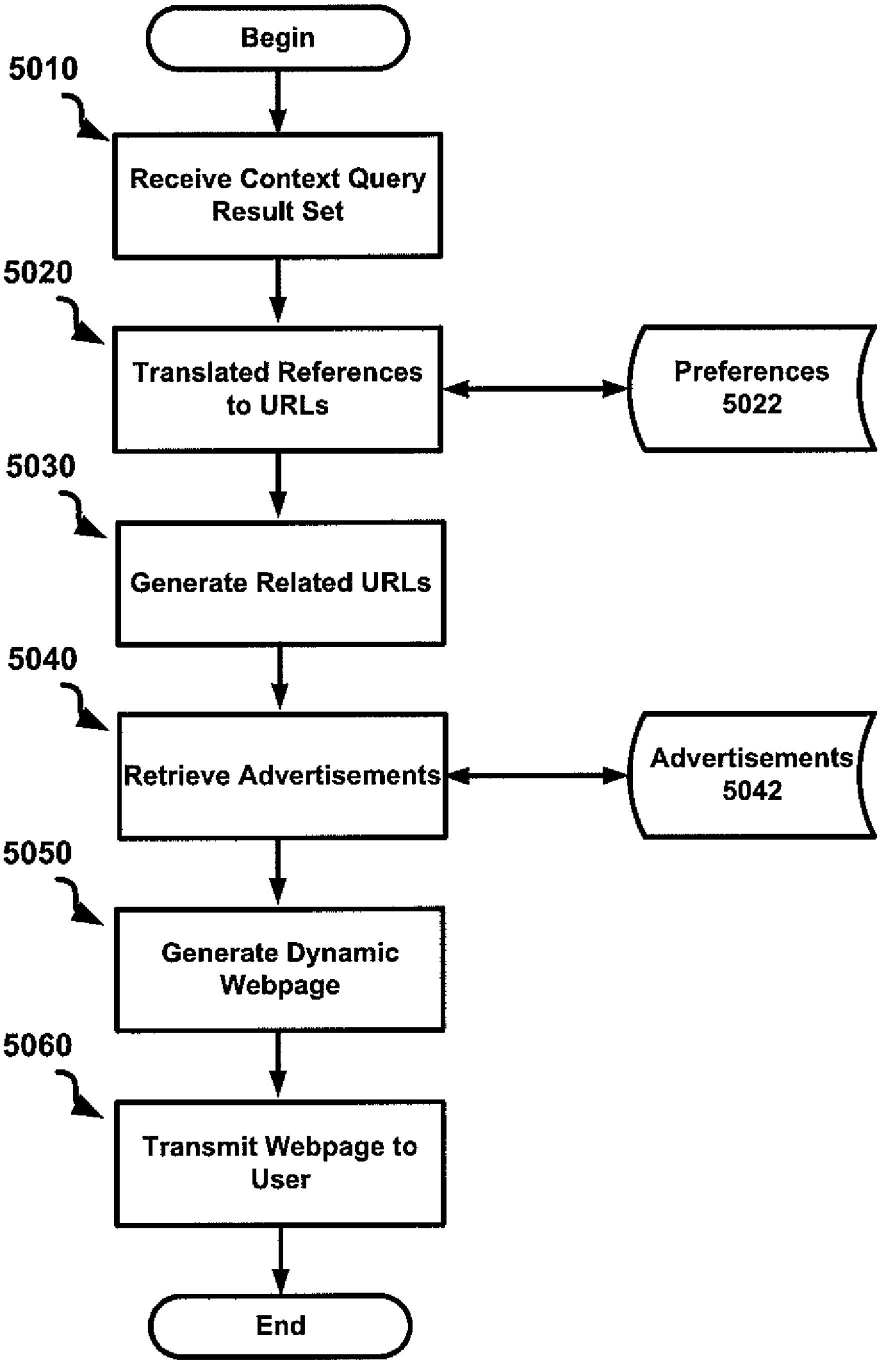
FIG. 15 illustrates one embodiment of a process 5000 of how a network containing temporal, spatial, and social network and topical data for a plurality of users, devices, and media (such as a W4 COMN), can be used support the building and transmission of dynamic web pages which can include links to W4 data objects, related URLs and advertisements.

FIG. 15 illustrates one embodiment of a process 5000 of how a network containing temporal, spatial, and social network and topical data for a plurality of users, devices, and media (such as a W4 COMN), can be used support the building and transmission of dynamic web pages which can include links to W4 data objects, related URLs and advertisements.

The process begins when result set from a context query is received 5010. As discussed in greater detail above under the heading of AUTOHYPERLINKING AND NAVIGATION IN URL BASED CONTEXT QUERIES, the result set may contain references to a set of containing one to many RWEs and IOs relating to the context. The result set may additionally comprise the context query that was originally entered.

The data object references in the result set are then translated to 5020 to URLs that can be used to retrieve data relating to each data object. A URL can be constructed that allows retrieval of data relating to the objects. Where a reference within the result set resolves directly to a an IO representing a data object, such as a video of the concert, images from the concert, or a news story about the concert, the hyperlinks points to the data object, such as a JPEG, WAV, HTML or text file that a user can access directly from a browser. Where multiple data objects exist relating to the same content, links can be presented to all objects, or a single instance can be select using user or default preferences 5022, such as preferred sources or the highest quality available.

There may also be references, however, that do not directly resolve to a data object. For example, references within a result set may refer to RWEs, which are typically represented in a W4 COMN by multiple data objects. In one embodiment, the system could generate a URL pointing to a data object representing a default object for the RWE (such as a profile), or to all data objects associated with the RWE. Alternatively, a URL could be generated containing a URL context query for the RWE:

The result set from the context query or the original context query (or both) is then used as a seed for generation of related URL based context queries 5030 using, in one embodiment, a process similar to that illustrated in FIG. 13 and described in detail above. Based on user or process needs, the process can create query generation criteria that specify cluster based or empirical query generation and limit the scope of related URL based context query generation.

Advertisements that are associated with the original context query (if any) are then retrieved 5040 from a database containing advertisements keyed by context query criteria. In one embodiment, all advertisements associated with a context query are sold, leased, or assigned to advertisers on a flat fee basis or unpaid basis. In one embodiment, the webpage output in step 5060 is input to a bid based advertising system and process described under the heading DERIVING INCOME FROM URL BASED CONTEXT QUERIES and illustrated in FIGS. 19 and 20 and accompanying text below. The bid based advertising system and process can insert additional advertisements in the webpage output in step 5060 of this process. In one embodiment, all advertisements are bid based and all advertisements are inserted by the bid based system, and step 5040 is omitted.

A dynamic webpage is then assembled 5050. The URLs created in step 5020 and 5030 are inserted into the webpage as hyperlinks. The advertisements are inserted into the dynamic web page and may comprise, among other things, text images, videos and so forth. The dynamic webpage is then transmitted 5060 to the user that entered the original context query.

Figure 16:
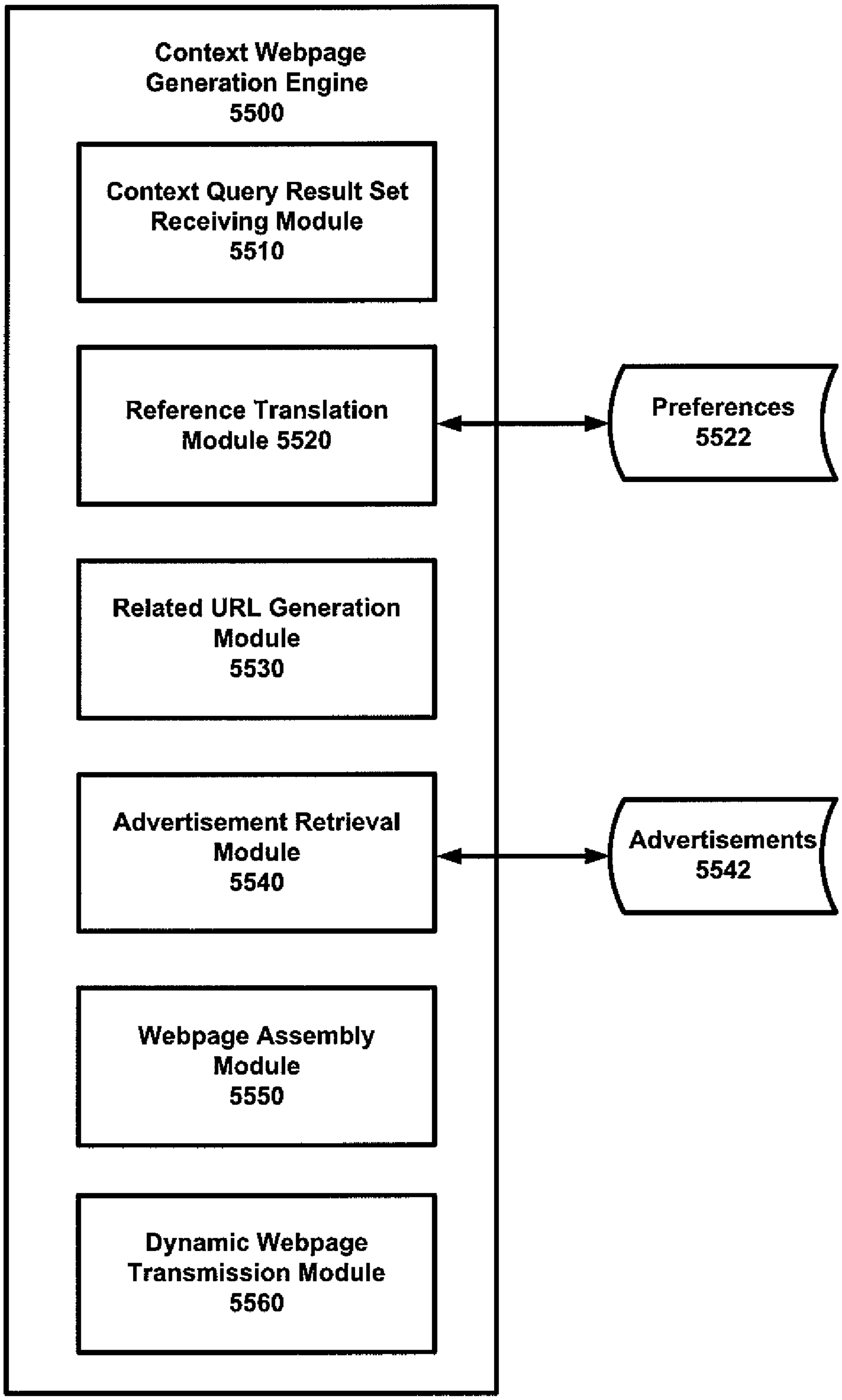
FIG. 16 illustrates one embodiment of a URL based context webpage generation engine 5500 that is capable of dynamically generating webpages 5500 within a W4 COMN or other network providing similar data and processing capabilities.

FIG. 16 illustrates one embodiment of a URL based context webpage generation engine 5500 that is capable of dynamically generating webpages 5500 within a W4 COMN or other network providing similar data and processing capabilities.

A context webpage generation engine 5500 resides on a server within the W4 COMN. The context webpage generation engine 5500 can be a component of a W4 engine, or, alternatively, may use services provided by components of a W4 engine or any of its constituent engines. The context webpage generation engine 5500 comprises a context query result set receiving module 5510, a reference translation module 5520, a related URL generation module 5530, an advertisement retrieval module 5540, a webpage assembly module 5550, and a dynamic webpage transmission module 5560.

The result set receiving module 5510 is configured to receive result sets from context queries. As discussed in greater detail above under the heading of AUTOHYPERLINKING AND NAVIGATION IN URL BASED CONTEXT QUERIES, result sets may contain references to a set of containing one to many RWEs and IOs relating to the context. Result set may additionally comprise the context query that was originally entered to obtain the result set.

The reference translation module 5520 translates references in context query result sets to URLs that can be used to retrieve data relating to each data object. A URL can be constructed that allows retrieval of data relating to the objects. Where a reference within the result set resolves directly to an IO representing a data object, the URL points to a data object that a user can access directly from a browser. Where multiple data objects exist relating to the same content, links can be presented to all objects, the reference translation module 5520 can select a single instance using user or default preferences 5522, such as preferred sources or the highest quality available. Where references do not directly resolve to a data object, such as a RWE, the reference translation module 5520 can, in one embodiment, generate URLs pointing to default objects for the RWE (such as a profile) to all data objects associated with the RWE, or a URL context query for the RWE:

The related URL generation module 5530 is configured to use the result sets from the context queries or original context queries (or both) as seeds for generation of related URL based context queries. In one embodiment, the related generation module 5530 is the URL based context query generation engine 4500 illustrated in FIG. 14 and described in detail above. Based on user or process needs, the related URL generation module 5530 can create query generation criteria that specify cluster based or empirical query generation and limit the scope of related URL based context query generation.

The advertisement retrieval module 5540 retrieves advertisements that are associated with original context queries (if any) from a database containing advertisements keyed by context query criteria. In one embodiment, all advertisements associated with a context query are sold, leased, or assigned to advertisers on a flat fee basis or unpaid basis. In one embodiment, webpages output by the dynamic webpage transmission module 5560 are input to the context query advertising revenue engine 7500 illustrated in FIGS. 19 and 20 and described in accompanying text below that can insert additional advertisements in output webpages. In one embodiment, all advertisements are bid based and all advertisements are inserted by the context query advertising revenue engine 7500 and advertisement retrieval module 5540 is optional.

The webpage assembly module 5550 is configured to assemble webpages by inserting URLs created by the reference translation module 5520 and related URL generation module 5530 as hyperlinks into dynamically generated webpages and inserting advertisements into dynamically generated webpages. The advertisements so inserted may comprise, among other things, text images, videos and so forth. The dynamic webpage transmission module 5560 is configured to transmit dynamic webpages generated by the webpage assembly module 5550 to users that originally entered the context queries.

Figure 17:
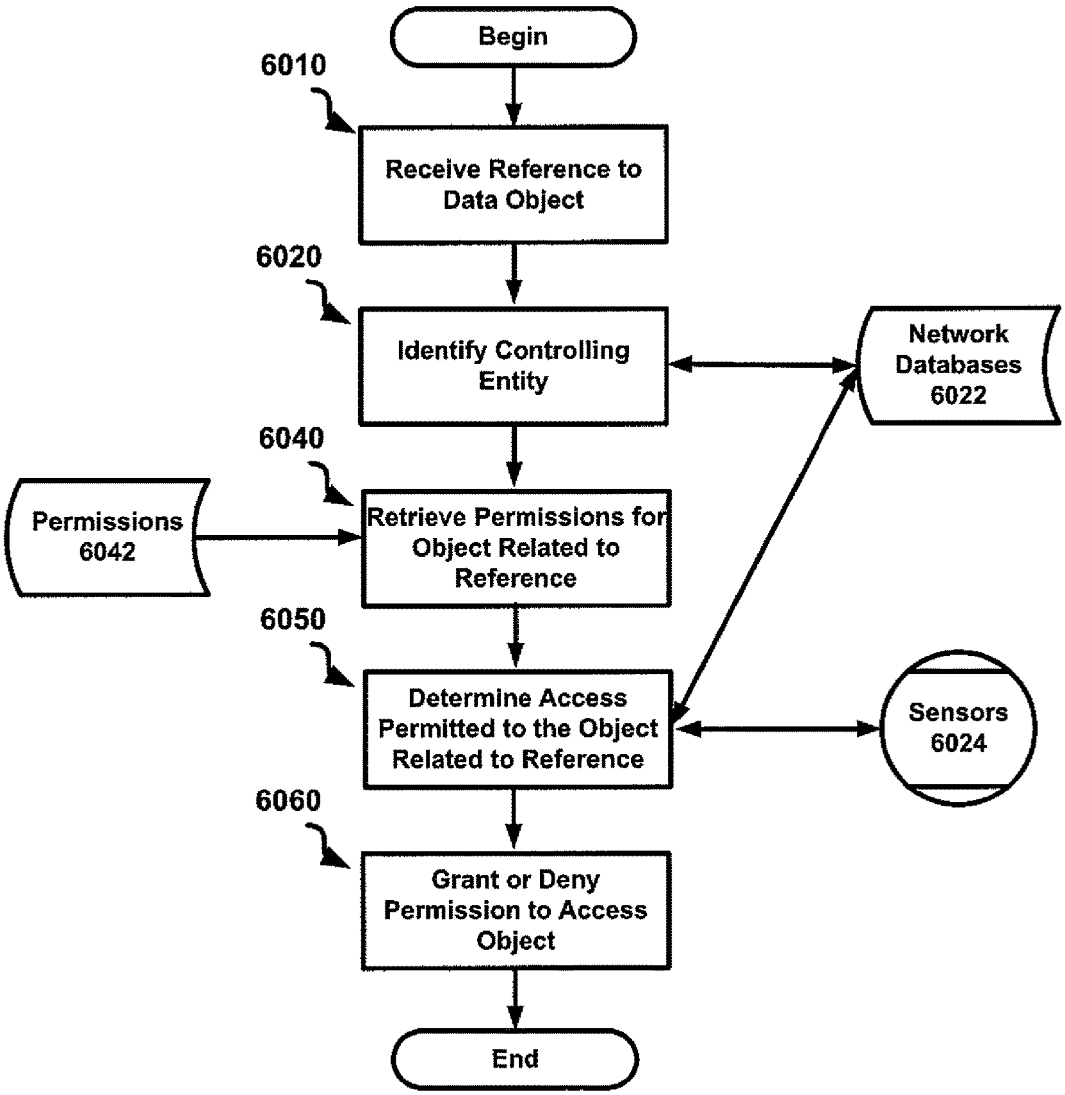
FIG. 17 illustrates one embodiment of a process 6000 of how a data objects within a network containing temporal, spatial, and social network and topical data for a plurality of users, devices, and media (such as a W4 COMN), can be protected using a permission based data security system.

FIG. 17 illustrates one embodiment of a process 6000 of how a data objects within a network containing temporal, spatial, and social network and topical data for a plurality of users, devices, and media (such as a W4 COMN), can be protected using a permission based data security system.

The process begins when a reference to a W4 object is received 6010 from, or on behalf of, a user. The reference can one of a plurality of references in result set from a context query. As discussed in greater detail above under the heading of URL BASED QUERY FOR RETRIEVING DATA RELATED TO A CONTEXT, such result sets may contain references to a set of references referring to one to many RWEs and IOs relating to the context.

The RWE controlling the W4 object to which the reference refers is then identified 6020. In one embodiment, a second reference to a controlling RWE can be embedded in metadata in the object to which the reference relates. In one embodiment, the process can retrieve spatial, temporal, social and topical data related to the object to which the reference refers to identify the controlling RWE for an object. In one embodiment, the process retrieves the spatial, temporal, social and topical data related to the object using a global index available to the network.

If the reference relates to an object which has no controlling RWE (such as a shared network object, access is granted to the object and the process ends. If a controlling RWE is identified, the permissions for objects controlled by that RWE are retrieved 6040. In one embodiment, object permissions for an RWE are stored on a computer-readable medium available to the network 6042. In one embodiment, permissions are stored within an IO associated with the RWE, for example, as a component of a profile IO, or, alternatively as a separate IO comprising permissions data.

In one embodiment, permissions can be stated as spatial, temporal, social and topical permissions. One conceptual format for such permissions could be:

<context>,<permit>($who_1$,$who_2$, . . . ),<deny>($who_a$, $who_b$, . . . )

where context is can be any kind of W4 context definition that defines a context that can contains object controlled by the RWE. ($who_1$,$who_2$, . . . ) is a list of one to many persons, entities, or groups of persons or entities that are permitted to view data objects that meet the permission definition, and ($who_a$,$who_b$, . . . ) is a list of one to many persons, entities, or groups of persons or entities that are not permitted to view data objects that meet the permission definition. The scope of the two lists can overlap. In one embodiment, the context could be stated as a context query that has the same format as a URL based context query.

In one embodiment, the context could be defined as a set of associations of data axes and values, for example:

([<data-axis>,<data-value>])

where <data-axis> can be "who", "what", "when" or "where" or "all", <data-value> can be any valid canonical, relational or symbolic value that is valid for a specific data axis and where the context may contain one to many data axis/value pairs.

For example, consider a set of permissions for objects controlled by a user RWE associated with User A. A set of permissions could read:

(a.) (all,any),deny(all)
(b.) (who,any),permit(friends)
(c.) (where,any,when,any),permit(User B, UserC)
(d.) (what, music),permit(friends)
(e.) (what,blog),permit(any), deny(family)
(e.) (what,drug+abuse),deny(all)

where permissions are evaluated in the order shown and later rules override earlier rules.

In the example, User A begins with a default rule (a.) that denies permission to all of his or her data to the rest of the world. Rule (b.) permits friends to view all of User A's social data. Rule (c.) permits only User B and C to view User A's spatial and temporal data. Rule (d.) permits only User B and C to view User A's data relating to music. Rule (e.) permits anyone to view User A's BLOG, except family members. Rule (e.) denies permission to anyone to view User A's data related to drug abuse.

In the embodiment above, permissions are simply stated as "permit" and "deny". In one embodiment, "permit" could mean that any entities in the permit list are allowed to view and link through the object to associated objects, and, "deny" could mean that any entities in the deny list are not allowed to view the object or link through the object to associated objects. Other schemes are possible. For example, a user may choose to allow other users to link through a object, but not to view it. For example, a may have paid for a copy of a media object like a hit song, and may not mind that a context query reveals the user listens to music by the composer of the song, but does not want anyone to be able to download the song.

Once permissions have been retrieved for the RWE controlling the object of the reference, the level of access permitted to the object is determined 6050. Where context based permission criteria are used, in one embodiment, the process retrieves spatial, temporal, social and topical data related to the context in the permission rule and the object to which the reference refers to determine if the object falls within the permission context. In one embodiment, the process retrieves spatial, temporal, social and topical data related to the object using a global index available to the network.

If the user is permitted to view the object, permission to view the object is granted 6060, otherwise permission is denied. In one embodiment, if an object is controlled by two or more RWEs, permissions for all controlling RWEs are evaluated and the most restrictive is applied. In one embodiment, if an object is controlled by two or more RWEs, permissions for all controlling RWEs are evaluated and the least restrictive is applied. In one embodiment, objects can only be controlled by one RWE.

Figure 18:
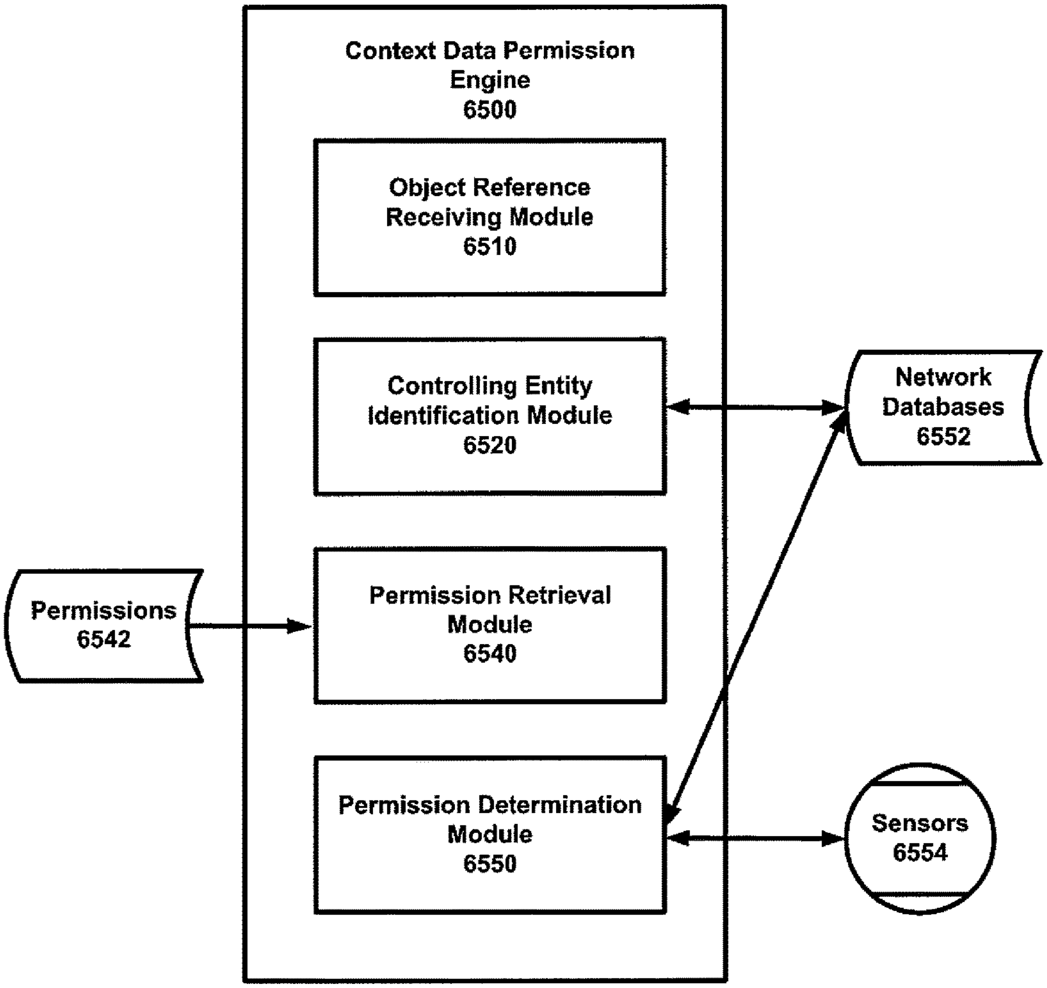
FIG. 18 illustrates one embodiment of a context data permission engine 6500 that is capable of providing a permission based data security system within a W4 COMN or other network providing similar data and processing capabilities.

FIG. 18 illustrates one embodiment of a context data permission engine 6500 that is capable of providing a permission based data security system within a W4 COMN or other network providing similar data and processing capabilities.

A context data permission engine 5400 resides on a server within the W4 COMN. The context data permission engine 5400 can be a component of a W4 engine, or, alternatively, may use services provided by components of a W4 engine or any of its constituent engines. The context data permission engine 5400 comprises an object reference receiving module 5410, a controlling entity identification module 5420, a permission retrieval module 5440, and a permission determination module 5450.

The object reference receiving module 5410 is configured to receive references to W4 objects from or on behalf of a user or process. In one embodiment, the module receives references individually. In one embodiment, the module is configured to accept sets of references comprising one to many individual object references. The reference can one of a plurality of references in result set from a context query. As discussed in greater detail above under the heading of URL BASED QUERY FOR RETRIEVING DATA RELATED TO A CONTEXT, such result sets may contain references to a set of references referring to one to many RWEs and IOs relating to a context.

The controlling entity identification module 5420 is configured to identify RWEs that control the objects to which references relate. In one embodiment, at least some objects to which references refer contain second references to controlling RWE embedded in metadata in the object. In one embodiment, the module is configured to retrieve spatial, temporal, social and topical data related to the objects to which references refer to in order to identify controlling RWEs for the objects. In one embodiment, the module is configured to retrieve spatial, temporal, social and topical data related to the object using a global index available to a network.

The permission retrieval module 5440 is configured to the permissions for objects controlled by that RWEs are identified by the controlling entity identification module 5420. In one embodiment, object permissions for an RWE are stored on a computer-readable medium available to the network 5442. In one embodiment, permissions are stored within an IO associated with the RWE, for example, as a component of a profile IO, or, alternatively as a separate IO comprising permissions data. In one embodiment, permissions can be stated as spatial, temporal, social and topical permissions.

The permission determination module 5450 is configured to determine the level of access users are permitted to objects for references received by the object reference receiving module 5410 using permissions retrieved by the permission retrieval module 5440. Where context based permission criteria are used, in one embodiment, the permission determination module 5450 is configured to retrieves spatial, temporal, social and topical data related to the context in the permission rule and the object to which the reference refers to determine if the object falls within the permission context. In one embodiment, the permission determination module 5450 is configured to retrieve spatial, temporal, social and topical data related to the object using a global index available to the network.

Figure 19:
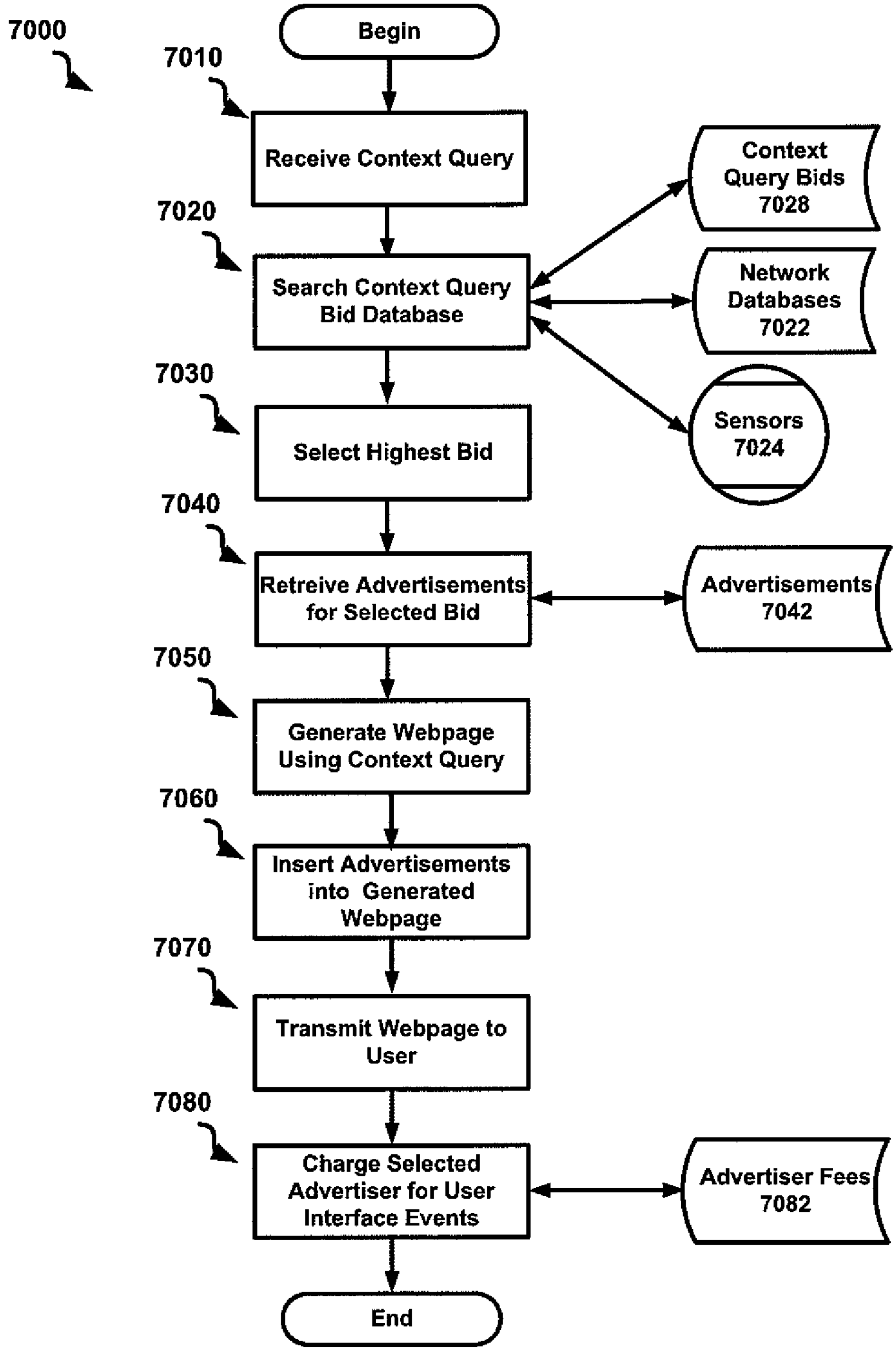
FIG. 19 illustrates one embodiment of a process 7000 of how URL based context queries can be used to generate revenue for a service provider.

FIG. 19 illustrates one embodiment of a process 7000 of how URL based context queries can be used to generate revenue for a service provider.

At the core of such a process are at least two databases available over a network: (1.) a context query bid database and (2.) an advertisement database. The context query bid database contains entries for a plurality of bids for placement of advertisements on webpages generated in response to specific context queries. In one embodiment, each entry comprises entry comprises a bid context query having at least one bid context criteria, a bid amount, an identification of an advertiser, and an identification of at least one advertisement.

The bid context query can include any combination be any who, what, when, or where criteria. In one embodiment, the criteria can be related to one another using standard relational or set operators. In one embodiment, the query can be stated as a natural language query. In one embodiment, the criteria are formatted as a string of criteria-attribute/value pairs as described above under the heading URL BASED QUERY FOR RETRIEVING DATA RELATED TO A CONTEXT.

The bid amount comprises a maximum amount the advertiser is willing to pay for advertisement placement or ranking on webpages generated in response to the bid context query. In one embodiment, the bid amount is a CPC or a CPM bid. The identification of an advertiser is a unique identifier assigned to bidding advertisers by the provider of the context query bid database. The identification of an advertisement is a unique identifier associated with a specific advertisement that the advertiser wishes to place on webpages generated in response to the bid context query. Each entry on the context query bid database can additionally, in one embodiment, include a targeting context that is used to identify a specific set of users the advertiser wishes to target. In one embodiment, targeting contexts can contain any number of spatial, temporal, social and topical contexts as described above in more detail in the section titled DERIVING INCOME FROM URL BASED CONTEXT QUERIES.

The advertisement database contains entries for a plurality of advertisements that an advertiser wishes to place on webpages generated in response to specific user context queries. In one embodiment, each entry comprises entry comprises an identification of an advertiser, an identification of an advertisement, and at least one advertisement data object. The identification of an advertiser is a unique identifier assigned to bidding advertisers by the provider of the context query bid database. The identification of an advertisement is a unique identifier associated with a specific advertisement. The advertisement data objects are objects suitable for presentation on or in association with a webpage that embody a component of an advertisement, such as an image, a video, an audio file or a flash overlay.

In one embodiment, the context query bid database is created by advertisers using facilities provided by the database provider. Such facilities can comprise one or more user interfaces accessible over the Internet which support entry and bidding on context queries. In one embodiment, the user interfaces enable a bidding process substantially as described above under the section titled DERIVING INCOME FROM URL BASED CONTEXT QUERIES.

The process 7000 begins when a context query containing at least one user context query is received 7010 over a network. The URL can be entered using a user proxy device such as, for example, a portable media player, PDA, computer, or cell phone. The context query within the URL can include any combination be any who, what, when, or where criteria. In one embodiment, the criteria can be related to one another using standard relational or set operators. In one embodiment, the query can be stated as a natural language query. In one embodiment, the criteria are formatted as a string of criteria-attribute/value pairs as described above under the heading URL BASED QUERY FOR RETRIEVING DATA RELATED TO A CONTEXT and in the general format http://<query server>/[<criteria-attribute>/<value>/]

where, in one embodiment, the relationship between the criteria can be determined by the selection of criteria attributes and the order of criteria within the query. The URL can be entered by the user in any manner known to the art. For example, the URL could have been directly entered by the user, could have been a link on a webpage or could have been generated by a software application.

The context query bid database 7022 is then searched 7020 to locate any bids on the user context query bid database where the user context query matches the bid context query. In one embodiment, a network data query is formulated based on the user context criteria so as to search, via the network, for user profile data, social network data, spatial data, temporal data, topical data and context query bid data that is available via the network and relates to the context so as to identify at least one entry in the context query bid database that relates to the user context criteria.

In one embodiment, only entries in the context query bid database are identified where the bid context criteria on the identified entries on the context query bid database is an exact match to the context criteria on the user context query. In another embodiment, entries in the context query bid database are identified where the bid context criteria on the identified entries on the context query bid database and the context criteria on the user context query both relate to at least a single entity or topic (such as, for example, a specific RWE or a specific IO.) In another embodiment, entries in the context query bid database are identified where the at bid context criteria on the identified entries on the context query bid database relate to at least one entity or topic that is closely related to a second entity that relates to context criteria on the user context query.

In one embodiment, if the context query bid database additionally includes a targeting context, the targeting context for each matching entry is evaluated to determine if the user falls within the context. In one embodiment, profile data, spatial data, temporal data, social data and topical data available to the network relating to the user and the targeting context is searched to determine if the user falls within the targeting context. If the user does not fall within the targeting content, the bid is not applicable to this user. If the search finds no bids relating to the user context query applicable to the user, no advertisements will be placed on a webpage generated in response to the user context query.

If more than one bid has been placed on the user context query that is applicable to the user submitting the query, in one embodiment, the bid having the highest bid amount is selected 7030. Any entries on the advertising database 7042 are retrieved 7040 where the advertiser identification and advertisement identification on the entries match the advertiser identification and advertisement identification on the selected bid. A bid can specify, in one embodiment, more than one advertisement. Each retrieved advertising database entry specifies one or more data objects to be placed on a webpage generated in response to the user context query A dynamic webpage is then generated 7050 using the context query. In one embodiment, the process used to generate the dynamic webpage is the process described in the section under the heading AUTOHYPERLINKING AND NAVIGATION IN URL BASED CONTEXT QUERIES. The data objects referenced in any entries on the advertising database retrieved in step 7030 are inserted into the dynamically generated webpage 7060. In one embodiment the data objects are actual data files such as JPEG or AVI files. In one embodiment the data objects network references to data files such as JPEG or AVI files.

The modified webpage is then transmitted 7070 to the user. The advertiser associated with the selected bid on the context bid database is charged a fee 7080 when a user interface event occurs on the dynamic webpage. The user interface event could be an action the user takes on a displayed advertisement data object, such a click or a mouseover (i.e. a CPC event) or could be when an advertisement is displayed (i.e. a CPM event.) The fee the advertiser is charged can be based on any formula the service provider implements for CPC or CPM charges, which, in one embodiment, would not exceed the advertiser's bid amount, but could be less based on other factors, such as CTR, overall advertiser outlays, and so forth. In one embodiment, advertiser fees are stored on a fee database available to the network for processing by the service provider's billing system.

Figure 20:
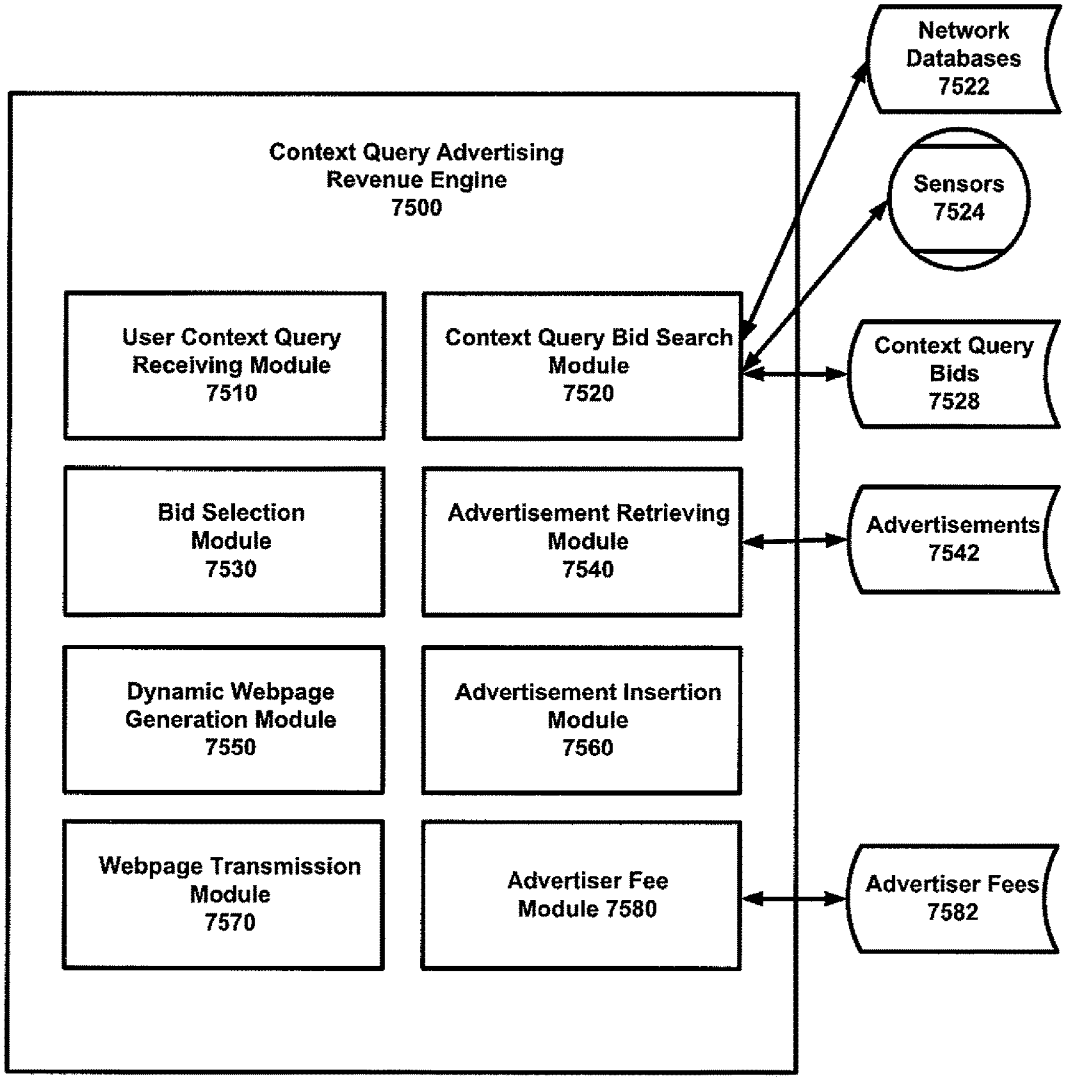
FIG. 20 illustrates one embodiment of a context query advertising revenue engine 7500 that is capable of providing a context query advertising system within a W4 COMN or other network providing similar data and processing capabilities.

FIG. 20 illustrates one embodiment of a context query advertising revenue engine 7500 that is capable of providing a context query advertising system within a W4 COMN or other network providing similar data and processing capabilities.

A context query advertising revenue engine 7500 resides on a server within the W4 COMN. The context query advertising revenue engine 7500 can be a component of a W4 engine, or, alternatively, may use services provided by components of a W4 engine or any of its constituent engines. The context query advertising revenue engine 7500 comprises a user context query receiving module 7510, a context query bid search module 7520, a bid selection module 7530, an advertisement retrieving module 7540, a dynamic webpage generation module 7550, an advertisement insertion module 7560 a webpage transmission module 7570 and an advertiser fee module 7580.

The user context query receiving module 7510 is configured to receive user context queries from users, wherein the user context queries contain at least one user context criteria. In one embodiment, the criteria can be related to one another using standard relational or set operators. In one embodiment, the query can be stated as a natural language query. In one embodiment, the criteria are formatted as a string of criteria-attribute/value pairs as described above under the heading URL BASED QUERY FOR RETRIEVING DATA RELATED TO A CONTEXT.

The context query bid search module 7520 is configured to formulate, for each user context query received by the user context query receiving module, a network data query based on user context criteria so as to search, via the network, for user profile data, social network data, spatial data, temporal data, topical data and context query bid data that is available via the network and relates to the context so as to identify at least one entry in a context query bid database 7528 that relates to the at least one context criteria.

In one embodiment, each entry on the context query bid comprises a bid context query having at least one bid context criteria, a bid amount, an identification of an advertiser, and an identification of at least one advertisement. The bid context query can include any combination be any who, what, when, or where criteria. In one embodiment, the criteria can be related to one another using standard relational or set operators. In one embodiment, the query can be stated as a natural language query. In one embodiment, the criteria are formatted as a string of criteria-attribute/value pairs as described above under the heading URL BASED QUERY FOR RETRIEVING DATA RELATED TO A CONTEXT.

In one embodiment, the context query bid search module formulates at least some queries such that only entries in the context query bid database are identified where the bid context criteria on the identified entries on the context query bid database are an exact match to context criteria on the user context query. In one embodiment, the context query bid search module formulates at least some queries such that the at least one bid context criteria on the identified entries on the context query bid database and the context criteria on the user context query both relate to a single entity or topic (such as an RWE or a topical IO.) In one embodiment, the context query bid search module formulates at least some queries such that entries in the context query bid database are identified where the bid context criteria on the identified entries on the context query bid database relate to at least one entity or topic that is closely related to a second entity or topic that relates to the at least one context criteria on the user context query.

In one embodiment, each entry on the context query bid database additionally includes a targeting context that is used to identify a specific set of users the advertiser wishes to target for that entry. The context query bid module 7520 is further configured to determine if users submitting user context queries fall within the targeting context of context query bids. In one embodiment, the context query bid search module 7520 searches profile data, spatial data, temporal data, social data and topical data available to the network relating users and the targeting contexts to determine if users fall within the targeting context. Bids do not apply to users that do not fall within targeting contents.

The bid selection module 7530 is configured to select one bid for every context query received by the user context query receiving module 7510 where more than one bid applies to the user context query. In one embodiment, bids having the highest bid amount are selected.

The advertisement retrieving module 7540 retrieves any entries on the advertising database relating to bids selected by the bid selection module 7530. In one embodiment, entries on the advertising database are retrieved where the advertiser identification and advertisement identification on the advertising database entries match the advertiser identification and advertisement identification on selected bids. A bid can specify, in one embodiment, more than one advertisement. Each retrieved advertising database entry specifies one or more data objects to be placed on a webpage generated in response to the user context query.

The dynamic webpage generation module 7550 is configured to generate dynamic webpages using user context queries. In one embodiment, the process used to generate the dynamic webpage is the process described in the section under the heading AUTOHYPERLINKING AND NAVIGATION IN URL BASED CONTEXT QUERIES. In one embodiment, the dynamic webpage generation module 7550 is the Context Webpage Generation Engine shown in FIG. 16 and described in detail above.

The advertisement insertion module 7560 is configured to insert data objects referenced in entries in the advertising database retrieved by the advertisement retrieving module 7540 into webpages generated by the dynamic webpage generation module 7550. In one embodiment the data objects are actual data files such as JPEG or AVI files. In one embodiment the data objects network references to data files such as JPEG or AVI files. The webpage transmission module 7570 is configured to transmit web pages modified by the advertisement insertion module 7560 to users who entered context queries received by the user context query receiving module 7510.

The advertiser fee module 7580 is configured to charge fees to advertisers associated with selected bids when user interface events occur on dynamic webpages in which the advertisement insertion module 7560 has inserted advertisements associated with the selected bid. The user interface events could be an action users take on a displayed advertisement data object, such a click or a mouseover (i.e. a CPC event) or could be when an advertisements data object is displayed (i.e. a CPM event.) The fee the advertiser is charged can be based on any formula the service provider implements for CPC or CPM charges, which, in one embodiment, would not exceed the advertiser's bid amount, but could be less based on other factors, such as CTR, overall advertiser outlays, and so forth. In one embodiment, advertiser fee module is configured to store advertiser fees on a fee database available to the network for processing by the service provider's billing system.

Those skilled in the art will recognize that the methods and systems of the present disclosure may be implemented in many manners and as such are not to be limited by the foregoing exemplary embodiments and examples. In other words, functional elements being performed by single or multiple components, in various combinations of hardware and software or firmware, and individual functions, may be distributed among software applications at either the client level or server level or both. In this regard, any number of the features of the different embodiments described herein may be combined into single or multiple embodiments, and alternate embodiments having fewer than, or more than, all of the features described herein are possible. Functionality may also be, in whole or in part, distributed among multiple components, in manners now known or to become known. Thus, myriad software/hardware/firmware combinations are possible in achieving the functions, features, interfaces and preferences described herein. Moreover, the scope of the present disclosure covers conventionally known manners for carrying out the described features and functions and interfaces, as well as those variations and modifications that may be made to the hardware or software or firmware components described herein as would be understood by those skilled in the art now and hereafter.

Furthermore, the embodiments of methods presented and described as flowcharts in this disclosure are provided by way of example in order to provide a more complete understanding of the technology. The disclosed methods are not limited to the operations and logical flow presented herein. Alternative embodiments are contemplated in which the order of the various operations is altered and in which sub-operations described as being part of a larger operation are performed independently.

While various embodiments have been described for purposes of this disclosure, such embodiments should not be deemed to limit the teaching of this disclosure to those embodiments. Various changes and modifications may be made to the elements and operations described above to obtain a result that remains within the scope of the systems and processes described in this disclosure.

We claim:

1. A method comprising the steps of:

receiving a reference, over a network, to a data object from a user;

identifying, via the network, an entity that controls the data object, such that spatial, temporal, social and topical data available to the network that relates to the data object are retrieved and utilized for said identifying the entity that controls the data object;

retrieving, via the network, a permission for the data object, the permission being associated with the entity that controls the data object, said permission comprising a permission context having permission context criteria comprising spatial, temporal, social and topical criteria, and further comprising a set of associations, data axes and data values between each of the spatial, temporal, social and topical criteria, the set of associations are ordered in an order such that each of the associations of the set of associations are evaluated in the order, such that associations that are lower in the order override associations that are higher in the order where the respective associations relate to a same respective data axes and respective data values;

retrieving, via the network, spatial data, temporal data, social data and topical data available to the network that relates to the user and to the permission context;

determining, via the network, using the spatial data, temporal data, social data and topical data, that the user matches the permission context criteria;

in response to determining the user matches the permission context criteria, determining, via the network, using the permission for the data object, the user is one of: permitted to access to the data object and not permitted to access to the data object, such that where the user is permitted access to the data object, access is granted to the data object, and where the user is not permitted access to the data object, access is denied to the data object.

2. The method of claim 1 wherein the reference to a data object is one of a of a plurality of references in result set of a context query, the context query comprising a URL-based query comprising spatial, temporal, social and topical criteria.

3. The method of claim 1 wherein a reference to the entity that controls the data object is embedded in metadata in the data object.

4. The method of claim 1 wherein, the spatial, temporal, social and topical data that relates to the data object is retrieved using a global index available to the network, the global index comprising a global graph that relates entities known to the network with one another.

5. The method of claim 1 such that where an object is controlled by two or more entities, permissions for all controlling entities are evaluated and the most restrictive is applied.

6. The method of claim 1 such that where an object is controlled by two or more entities, permissions for all controlling entities are evaluated and the least restrictive is applied.

7. The method of claim 1 such that where an object is not controlled by any entity, access is granted to the data object.

8. A system comprising:

a processor;

a non-transitory storage medium for tangibly storing thereon program logic for execution by the processor, the program logic comprising:

object reference receiving logic executed by the processor for receiving a reference, over a network, to a data object from a user;

controlling entity identification logic executed by the processor for identifying, via the network, an entity that controls the data object, such that spatial, temporal, social and topical data available to the network that relates to the data object are retrieved and utilized for said identifying the entity that controls the data object;

permission retrieval logic executed by the processor for retrieving, via the network, a permission for the data object, the permission being associated with the entity that controls the data object, said permission comprising a permission context having permission context criteria comprising spatial, temporal, social and topical criteria, and further comprising a set of associations, data axes and data values between each of the spatial, temporal, social and topical criteria, the set of associations are ordered in an order such that each of the associations of the set of associations are evaluated in the order, such that associations that are lower in the order override associations that are higher in the order where the respective associations relate to a same respective data axes and respective data values;

user data retrieval logic executed by the processor for retrieving, via the network, spatial data, temporal data, social data and topical data available to the network that relates to the user and to the permission context;

user matching logic executed by the processor for determining, via the network, using the spatial data, temporal data, social data and topical data, that the user matches the permission context criteria;

permission determination logic executed by the processor for, in response to determining the user matches the permission context criteria, determining, via the network, using the permission for the data object, the user is one of: permitted to access to the data object and not permitted to access to the data object, such that where the user is permitted access to the data object, access is granted to the data object, and where the user is not permitted access to the data object, access is denied to the data object.

9. The system of claim 8 wherein the references to a data object is one of a plurality of references in result set of a context query, the context query comprising a URL-based query comprising spatial, temporal, social and topical criteria.

10. The system of claim 8 wherein a reference to the entity that controls the data object is embedded in metadata in the data object.

11. The system of claim 8 wherein, the object reference receiving logic retrieves the spatial, temporal, social and topical data that relates to the data object using a global index available to the network, the global index comprising a global graph that relates entities known to the network with one another.

12. The system of claim 8 such that where an object is controlled by two or more entities, permissions for all controlling entities are evaluated by the permission determination logic and the most restrictive is applied.

13. The system of claim 8 such that where an object is controlled by two or more entities, permissions for all controlling entities are evaluated by the permission determination logic and the least restrictive is applied.

14. The system of claim 8 such that where an object is not controlled by any entity, permission determination logic grants access to the data object.

15. A non-transitory computer-readable storage medium for tangibly storing thereon computer readable instructions for a method comprising:

receiving a reference, over a network, to a data object from a user;

identifying, via the network, an entity that controls the data object, such that spatial, temporal, social and topical data available to the network that relates to the data object are retrieved and utilized for said identifying the entity that controls the data object;

retrieving, via the network, a permission for the data object, the permission being associated with the entity that controls the data object, said permission comprising a permission context having permission context criteria comprising spatial, temporal, social and topical criteria, and further comprising a set of association, data axes and data values between each of the spatial, temporal, social and topical criteria, the set of associations are ordered in an order such that each of the associations of the set of associations are evaluated in the order, such that associations that are lower in the order override associations that are higher in the order where the respective associations relate to a same respective data axes and respective data values;

retrieving, via the network, spatial data, temporal data, social data and topical data available to the network that relates to the user and to the permission context;

retrieving, via the network, spatial data, temporal data, social data and topical data available to the network that relates to the user and to the permission context;

determining, via the network, using the spatial data, temporal data, social data and topical data, that the user matches the permission context criteria;

in response to determining the user matches the permission context criteria, determining, via the network, using the permission for the data object, the user is one of: permitted to access to the data object and not permitted to access to the data object, such that where the user is permitted access to the data object, access is granted to the data object, and where the user is not permitted access to the data object, access is denied to the data object.

16. The non-transitory computer-readable storage medium of claim 15 wherein the reference to a data object is one of a of a plurality of references in result set of a context query, the context query comprising a URL-based query comprising spatial, temporal, social and topical criteria.

17. The non-transitory computer-readable storage medium of claim 15 wherein a reference to the entity that controls the data object is embedded in metadata in the data object.

18. The non-transitory computer-readable storage medium of claim 15 the spatial, temporal, social and topical data that relates to the data object is retrieved using a global index available to the network, the global index comprising a global graph that relates entities known to the network with one another.

19. The non-transitory computer-readable storage medium of claim 15 such that where an object is controlled by two or more entities, permissions for all controlling entities are evaluated and the most restrictive is applied.

20. The non-transitory computer-readable storage medium of claim 15 such that where an object is controlled by two or more entities, permissions for all controlling entities are evaluated and the least restrictive is applied.

21. The non-transitory computer-readable storage medium of claim 15 such that where an object is not controlled by any entity, access is granted to the data object.

* * * * *